(12) United States Patent
Hatakeyama et al.

(10) Patent No.: US 8,742,344 B2
(45) Date of Patent: Jun. 3, 2014

(54) INSPECTION APPARATUS

(71) Applicant: Ebara Corporation, Tokyo (JP)

(72) Inventors: Masahiro Hatakeyama, Tokyo (JP);
Yasushi Toma, Tokyo (JP); Shoji Yoshikawa, Tokyo (JP); Kiwamu Tsukamoto, Tokyo (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 14/026,385

(22) Filed: Sep. 13, 2013

(65) Prior Publication Data

US 2014/0077078 A1  Mar. 20, 2014

(30) Foreign Application Priority Data

Sep. 14, 2012 (JP) ................................. 2012-203375
Sep. 14, 2012 (JP) ................................. 2012-203379

(51) Int. Cl.
*G01N 23/00* (2006.01)
*G21K 7/00* (2006.01)

(52) U.S. Cl.
USPC ........... 250/310; 250/306; 250/307; 250/397; 250/492.2; 250/492.3

(58) Field of Classification Search
USPC ............ 250/306, 307, 310, 397, 492.2, 492.3
See application file for complete search history.

(56) References Cited

U.S. PATENT DOCUMENTS

| | | | |
|---|---|---|---|
| 6,265,719 B1* | 7/2001 | Yamazaki et al. | ............ 250/310 |
| 6,724,002 B2* | 4/2004 | Mankos et al. | ......... 250/492.24 |
| 2002/0028399 A1* | 3/2002 | Nakasuji et al. | ................ 430/30 |
| 2011/0024623 A1 | 2/2011 | Hatakeyama et al. | |

FOREIGN PATENT DOCUMENTS

| | | |
|---|---|---|
| JP | 11-132975 A | 5/1999 |
| JP | 2007-48686 A | 2/2007 |
| WO | 02/01596 A1 | 3/2002 |

* cited by examiner

*Primary Examiner* — Jack Berman
*Assistant Examiner* — Meenakshi Sahu
(74) *Attorney, Agent, or Firm* — Pearne & Gordon LLP

(57) ABSTRACT

An inspection apparatus includes: beam generation means for generating any of charged particles and electromagnetic waves as a beam; a primary optical system that guides the beam into an inspection object held in a working chamber and irradiates the inspection object with the beam; a secondary optical system that detects secondary charged particles occurring from the inspection object; and an image processing system that forms an image on the basis of the detected secondary charged particles. The primary optical system includes a photoelectron generator having a photoelectronic surface. The base material of the photoelectronic surface is made of material having a higher thermal conductivity than the thermal conductivity of quartz. A central portion of the inspection object is provided with a central flat portion 390. The periphery of the central flat portion 390 is provided with peripheral flat portion 392 via a step 391. The periphery of the step 391 is provided with an electric field correction plate 400. A surface voltage equivalent to a surface voltage applied to the inspection object is applied to an electrode 401 on the electric field correction plate 400.

9 Claims, 42 Drawing Sheets

FIG.10
(a)
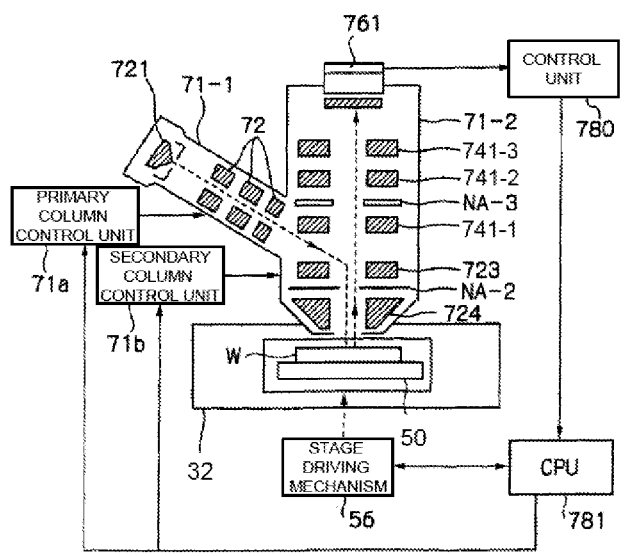
(b)
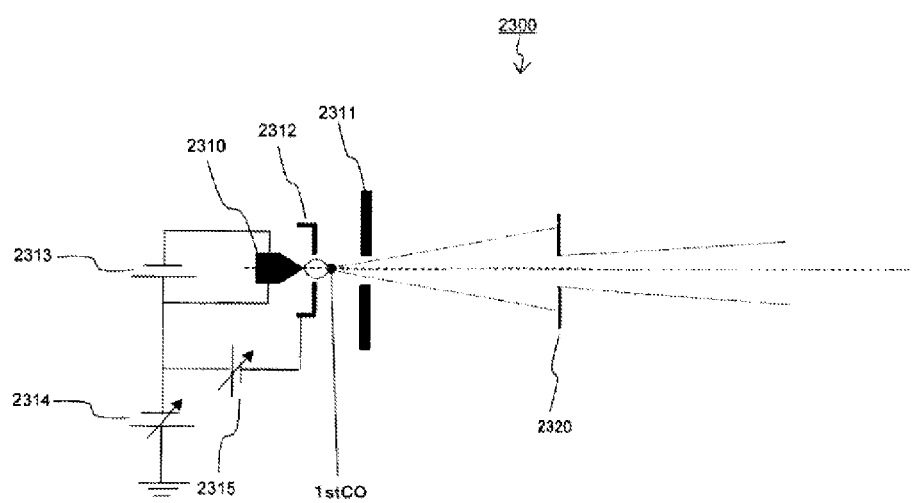

FIG.11
(a)
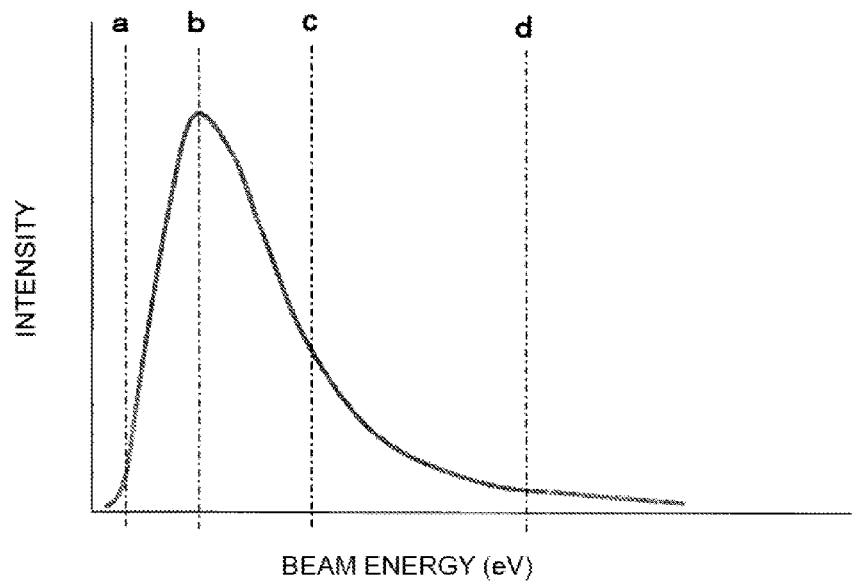
(b)
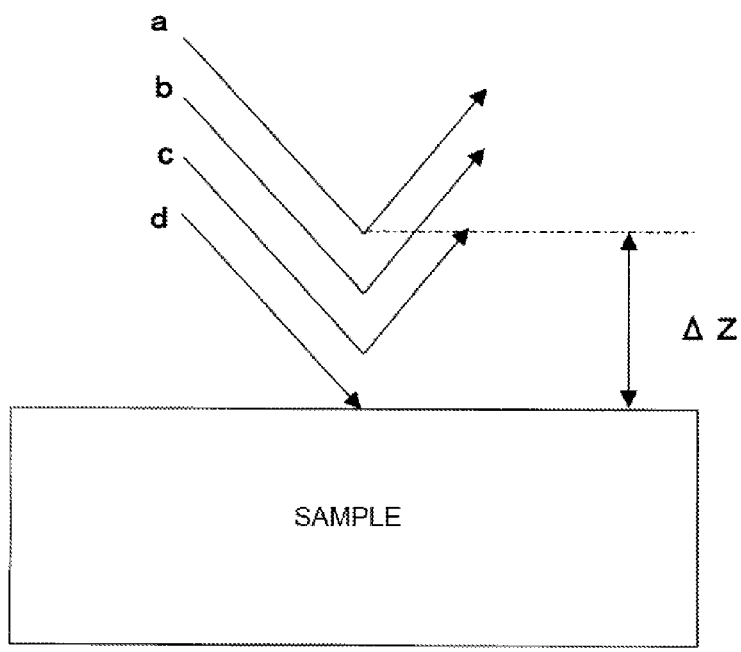

FIG.32
(a)
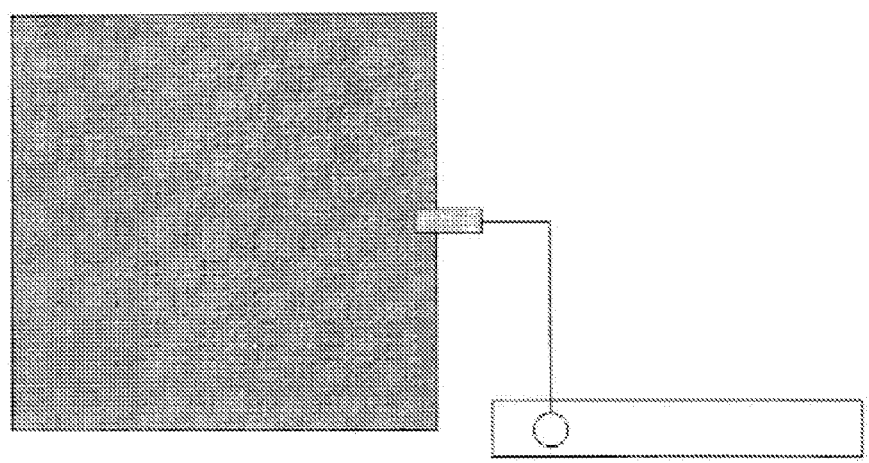
(b)
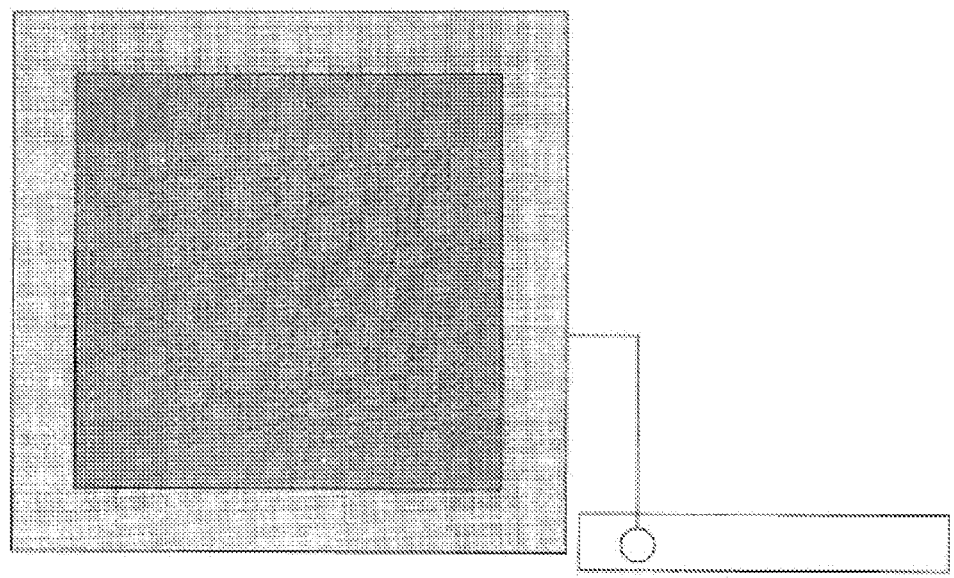

FIG.34
(a)
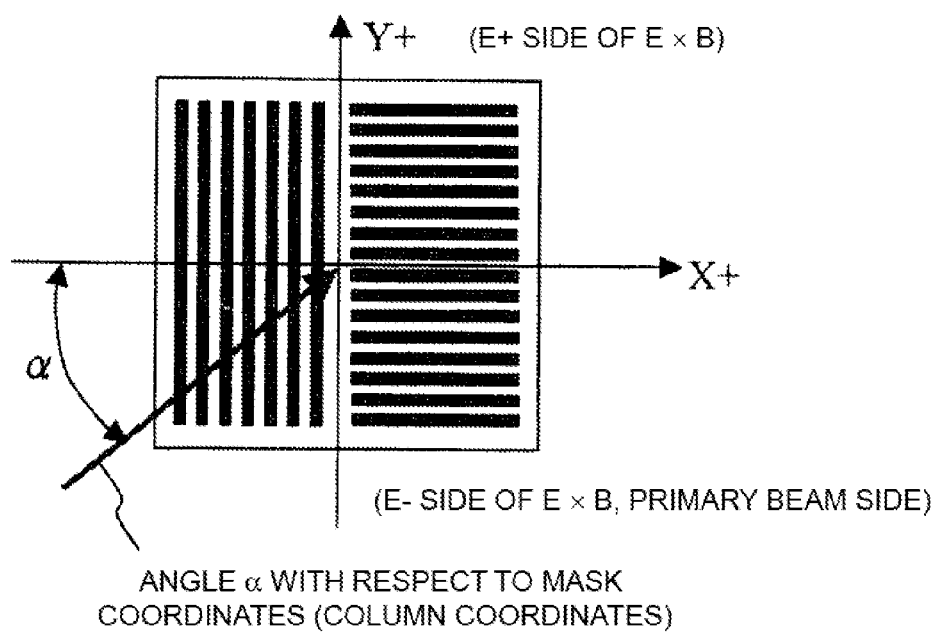
ANGLE α WITH RESPECT TO MASK
COORDINATES (COLUMN COORDINATES)
(b)
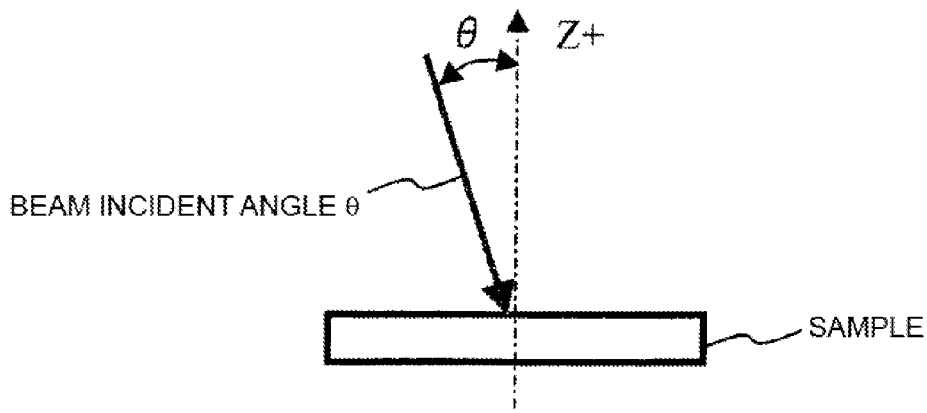

INSPECTION APPARATUS

BACKGROUND OF THE INVENTION

1. Field of the Invention

The present invention relates to an inspection apparatus that inspects defects of a pattern formed on a surface of an inspection object, and specifically, to an inspection apparatus that captures secondary charged particles varying properties of a surface of an inspection object, forms image data, and inspects a pattern and the like formed on the surface of the inspection object on the basis of the image data at a high throughput, and an inspection method.

2. Description of the Related Art

A conventional semiconductor inspection apparatus supports a 100 nm design rule and technologies. Samples as inspection objects are wafers, exposure masks, EUV masks, NIL (nanoimprint lithography) masks, and substrates; the samples have thus been varying. At present, apparatuses and technologies that support a design rule for samples with 5 to 30 nm are required. That is, it is required to support L/S (line/space) or hp (half pitch) nodes of 5 to 30 nm in a pattern. In the case where an inspection apparatus inspects such samples, it is required to achieve a high resolution.

Here, "samples" are exposure masks, EUV masks, nanoimprint mask (and templates), semiconductor wafers, substrates for optical elements, substrates for optical circuits and the like. The samples include samples with patterns and samples without patterns. The samples with patterns include samples with asperities and samples without asperities. Patterns are formed of different materials on the samples without asperities. The samples without patterns include samples coated with an oxide film and samples with no oxide film.

Problems of the conventional inspection apparatuses are summarized as follows.

A first problem is insufficient resolution and throughput. In a conventional art of a mapping optical system, the pixel size is about 50 nm, and the aberration is about 200 nm. Achievement of further high resolution and improvement of the throughput require reduction in aberration, reduction in energy width of irradiation current, a small pixel size, and increase in current intensity.

A second problem is that, in the case of SEM inspection, the finer the structure to be inspected, the more serious the throughput problem is. This problem occurs because the resolution of an image is insufficient if a smaller pixel size is not used. These points are caused because the SEM forms an image and inspects defects on the basis of edge contrast. For instance, in the case of a pixel size of 5 nm and 200 MPPS, the throughput is approximately 6 hr/cm$^2$. This example takes a time 20 to 50 times as long as the time of mapping projection. The time is unrealistic for inspection.

Patent Document 1: International Publication No. WO2002/001596
Patent Document 2: Japanese Patent Laid-Open No. 2007-48686
Patent Document 3: Japanese Patent Laid-Open No. H11-132975

SUMMARY OF THE INVENTION

The conventional inspection apparatuses adopt quartz and synthetic quartz as base materials for the photoelectronic surfaces of photoelectron generators. Quartz and synthetic quartz have a low thermal conductivity. Accordingly, heat at a portion subjected to electronic irradiation cannot be quickly dispersed. There is thus a problem in that, if the power density of laser with which the photoelectronic surface is irradiated is increased to improve the resolution of the inspection apparatus and improve the throughput, the photoelectronic surface is damaged by electronic irradiation, quantum efficiency is reduced, and inconsistencies occur in quantum efficiency with respect to positions.

The present invention has been made in view of the problems. It is an object of the present invention to provide an inspection apparatus that can reduce damage to photoelectronic surface caused by electronic irradiation.

There is another problem in that, when the conventional inspection apparatus inspects a sample having what is referred to as a "mesa structure", the electric field is nonuniform at ends of the mesa structure (in proximity to a step) and it is thus difficult to acquire an image having high contrast and a high S/N ratio.

The present invention has been made in view of the problem. It is an object to provide an inspection apparatus that can acquire an image having high contrast and a high S/N ratio at the ends of the mesa structure.

An inspection apparatus of the present invention includes: beam generation means for generating any of charged particles and electromagnetic waves as a beam; a primary optical system that guides the beam into an inspection object held in a working chamber and irradiates the inspection object with the beam; a secondary optical system that detects secondary charged particles occurring from the inspection object; and an image processing system that forms an image on the basis of the detected secondary charged particles, wherein the primary optical system includes a photoelectron generator having a photoelectronic surface, and a base material of the photoelectronic surface is made of material with a higher thermal conductivity than a thermal conductivity of quartz.

In the inspection apparatus of the present invention, the base material of the photoelectronic surface may be made of sapphire or diamond. The photoelectronic surface may have a circular shape having a diameter of 10 to 200 μm or a rectangular shape having a side of 10 to 200 μm.

In the inspection apparatus of the present invention, photoelectronic material may be coated on the photoelectronic surface, and the photoelectronic material may be ruthenium or gold. The photoelectronic material may have a thickness of 5 to 100 nm.

The present invention can provide the inspection apparatus that can reduce damage to the photoelectronic surface caused by electronic irradiation.

An inspection apparatus of the present invention includes: beam generation means for generating any of charged particles and electromagnetic waves as a beam; a primary optical system that guides the beam into an inspection object held in a working chamber and irradiates the inspection object with the beam; a secondary optical system that detects secondary charged particles occurring from the inspection object; and an image processing system that forms an image on the basis of the detected secondary charged particles, wherein a central portion of the inspection object is provided with a central flat portion, a periphery of the central flat portion is provided with a peripheral flat portion via a step, and an electric field correction plate is arranged around the step, and a surface voltage equivalent to a surface voltage applied to the inspection object is applied to an electrode on a surface of the electric field correction plate.

In the inspection apparatus of the present invention, the electric field correction plate comprises an insulation layer provided below the electrode, and an electrode that is for an electrostatic chuck and is provided below the insulating layer, and the electric field correction plate may be in close contact with the inspection object by applying a voltage to the electrode for the electrostatic chuck.

An inspection apparatus of the present invention includes: beam generation means for generating any of charged particles and electromagnetic waves as a beam; a primary optical system that guides the beam into an inspection object held in a working chamber and irradiates the inspection object with the beam; control means for controlling an incident angle of the beam with which the inspection object is irradiated; a secondary optical system that detects secondary charged particles occurring from the inspection object; and an image processing system that forms an image on the basis of the detected secondary charged particles, wherein a central portion of the inspection object is provided with a central flat portion, a periphery of the central flat portion is provided with a peripheral flat portion via a step, relationship between a detection position of the secondary charged particles in proximity to the step and the incident angle of the beam is stored as mapping data in a storage, and when proximity to the step is inspected, the control means controls the incident angle of the beam so as to correct deviation of the detection position of the secondary charged particles on the basis of the mapping data.

In the inspection apparatus of the present invention, wherein the control means is a movable numerical aperture, and a movement mechanism for the numerical aperture, the mapping data is data that maps a relationship between a plurality of mirror electron positions in proximity to the step and a position of the numerical aperture, and when proximity to the step is inspected, the numerical aperture is moved by the movement mechanism on the basis of the mapping data, and the incident angle of the beam may be controlled to correct a deviation of the mirror electron position.

The present invention can provide an inspection apparatus capable of acquiring an image having high contrast and a high S/N ratio at ends of a mesa structure.

BRIEF DESCRIPTION OF THE DRAWINGS

FIG. 5A is a side view. FIG. 5B is a sectional view taken along line E-E of FIG. 5A;

FIGS. 10A and 10B are diagrams showing an example of an inspection apparatus including an electron gun according to this embodiment of the present invention;

FIGS. 11A and 11B are diagrams showing the intensity (amount) of irradiation current of an electron beam with which a surface of a sample is to be irradiated, and a state of energy and a state of the beam with which the surface of the sample is irradiated, according to an embodiment of the present invention;

FIGS. 32A and 32B are diagrams showing uniform and stable supply of sample surface potential, according to an embodiment of the present invention;

FIGS. 34A and 34B are diagrams showing an incident angle of a primary beam onto a sample in an inspection method according to an embodiment of the present invention;

DETAILED DESCRIPTION OF THE PREFERRED EMBODIMENTS

Figure 1:
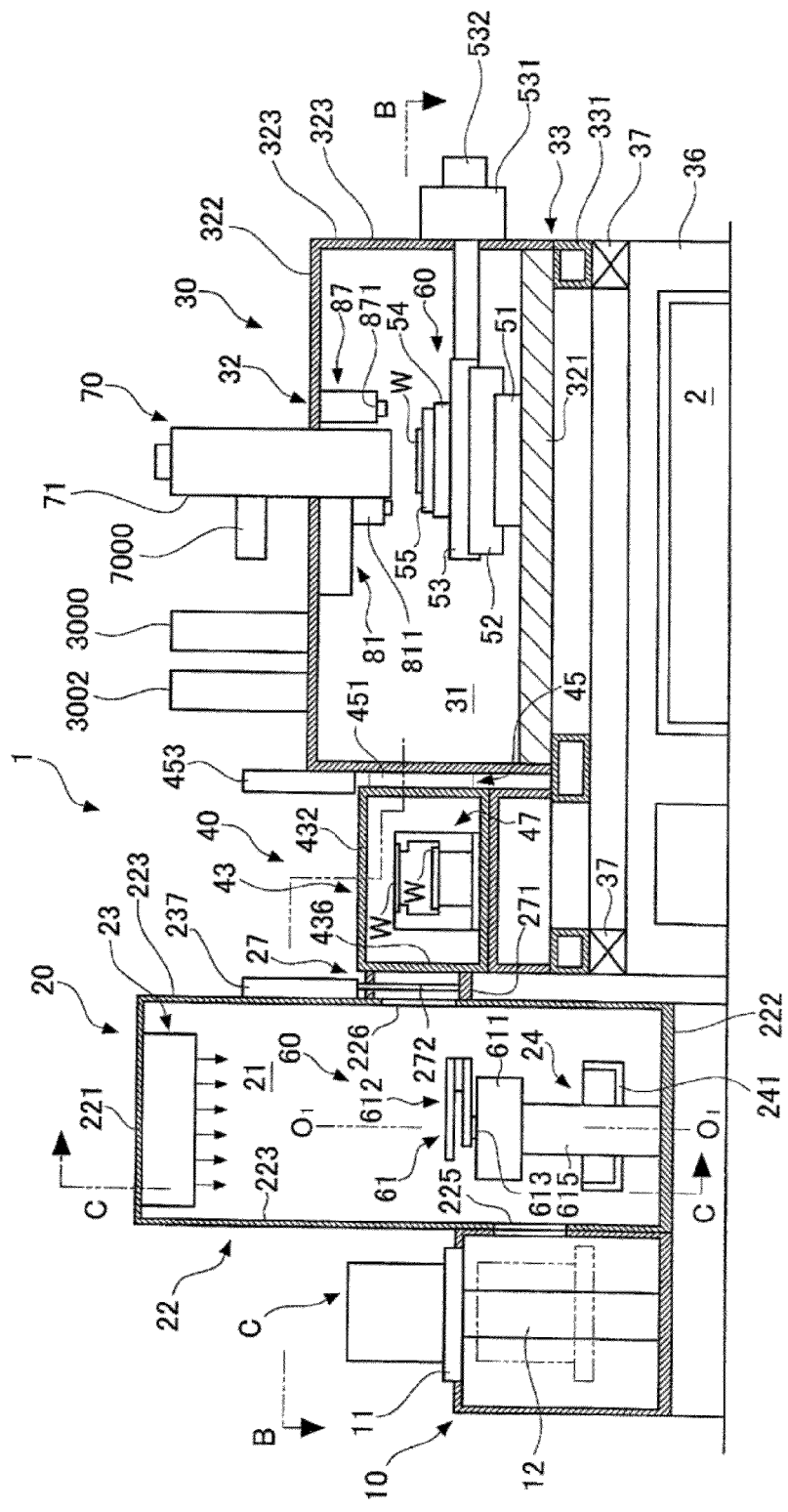
FIG. 1 is an elevational view showing main configuration components in an inspection apparatus according to an embodiment of the present invention taken along line A-A of FIG. 2.

Referring to the drawings, embodiments of the present invention will hereinafter be described on a semiconductor inspection apparatus that inspects a substrate, or a wafer, on which a pattern is formed, as an inspection object. Note that the following embodiments are examples of an inspection apparatus and an inspection method of the present invention. This invention is not limited to the examples.

Figure 2A:
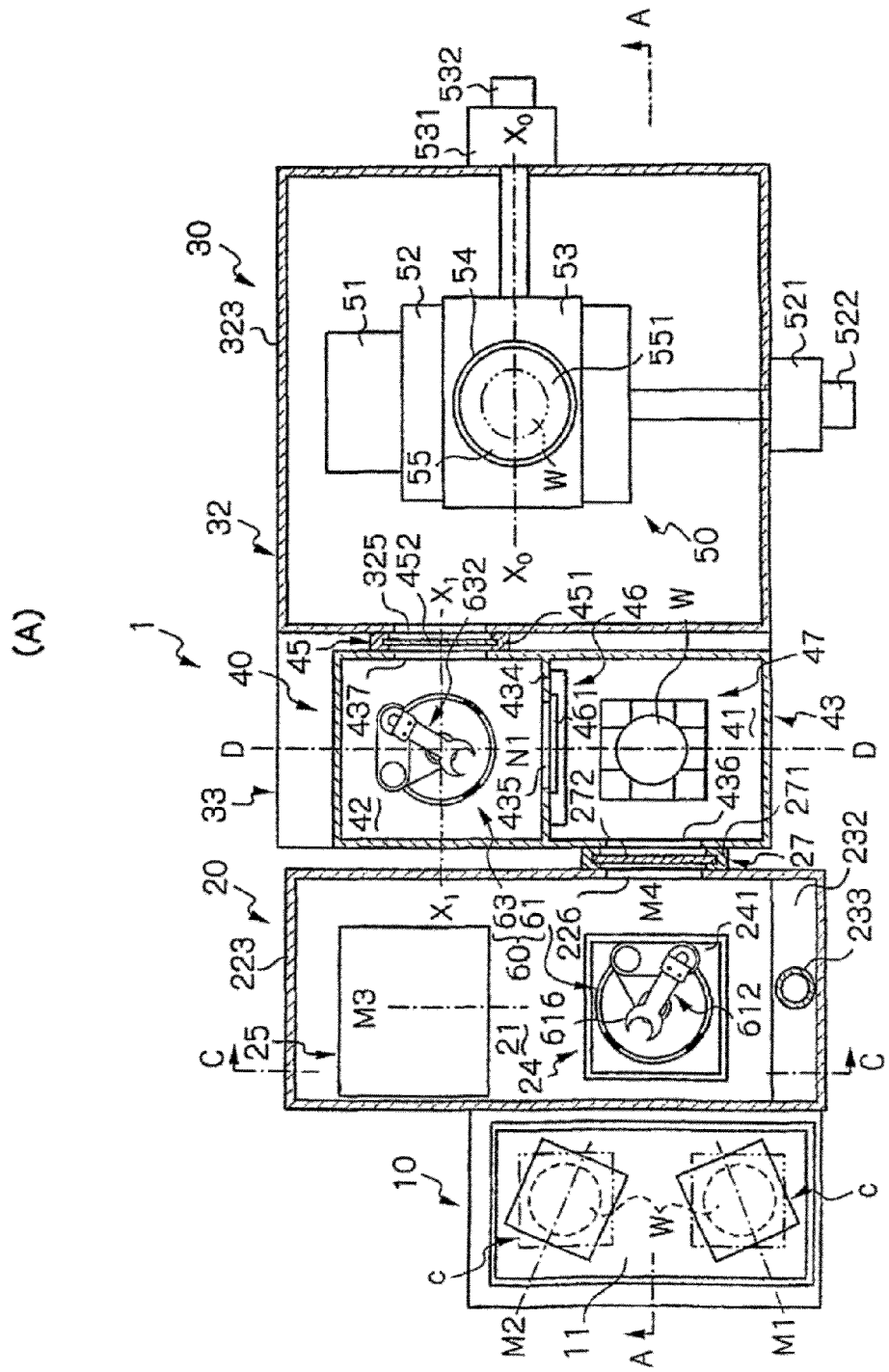
FIG. 2A is a plan view of the main configuration components of the inspection apparatus shown in FIG. 1 taken along line B-B of FIG. 1.

FIGS. 1 and 2A respectively show an elevational view and a plan view of main configuration components of a semiconductor inspection apparatus 1 of this embodiment.

The semiconductor inspection apparatus 1 of this embodiment includes: a cassette holder 10 that holds a cassette storing multiple wafers; a mini-environment device 20; a main housing 30 that defines a working chamber; a loader housing 40 that is disposed between the mini-environment device 20 and the main housing 30 to define two loading chambers; a loader 60 that loads a wafer from the cassette holder 10 onto a stage device 50 disposed in the main housing 30; an electronic optical device 70 attached to a vacuum housing; an optical microscope 3000; and a scanning electron microscope (SEM) 3002. These components are disposed in a positional relationship as shown in FIGS. 1 and 2A. The semiconductor inspection apparatus 1 further includes: a precharge unit 81 disposed in the vacuum main housing 30; a potential application mechanism 83 (shown in FIG. 14) that applies a potential to a wafer; an electron beam calibration mechanism 85; and an optical microscope 871 that configures an alignment controller 87 for positioning the wafer on the stage device. The electronic optical device 70 includes a lens tube 71 and a light source tube 7000. The internal configuration of the electronic optical device 70 will be described later.

Cassette Holder

The cassette holder 10 holds a plurality of (two in this embodiment) cassettes c (e.g., closed cassettes, such as SMIF and FOUP, made by Asyst technologies Inc.) each of which stores a plurality of (e.g., 25) wafers in a state of being arranged in the vertical direction in horizontal orientation. In the case of conveying the cassette by a robot or the like and automatically loading the cassette to the cassette holder 10, a cassette holder suitable to this loading manner is adopted. In the case of manual loading, a cassette holder that has an open cassette structure suitable to this loading manner is adopted. Any of the holders can be selected and installed. In this embodiment, the cassette holder 10 is in conformity with a system of automatically loading the cassette c, and includes, for instance, a lifting table 11, and a lifting mechanism 12 that vertically lifts and lowers the lifting table 11. The cassette c can be automatically set onto the lifting table in a state indicated by a chain line in FIG. 2A. After the setting, the cassette is automatically turned to a state indicated by a solid line in FIG. 2A to be aligned with the turning axis of a first conveyance unit in the mini-environment device. The lifting table 11 is lowered to a state indicated by a chain line in FIG. 1. Thus, the cassette holder used in the case of automatic loading or the cassette holder used in the case of manual loading may be appropriately selected among cassettes having publicly known structures. Accordingly, detailed description on the structure and functions of the cassette holder is omitted.

Figure 2B:
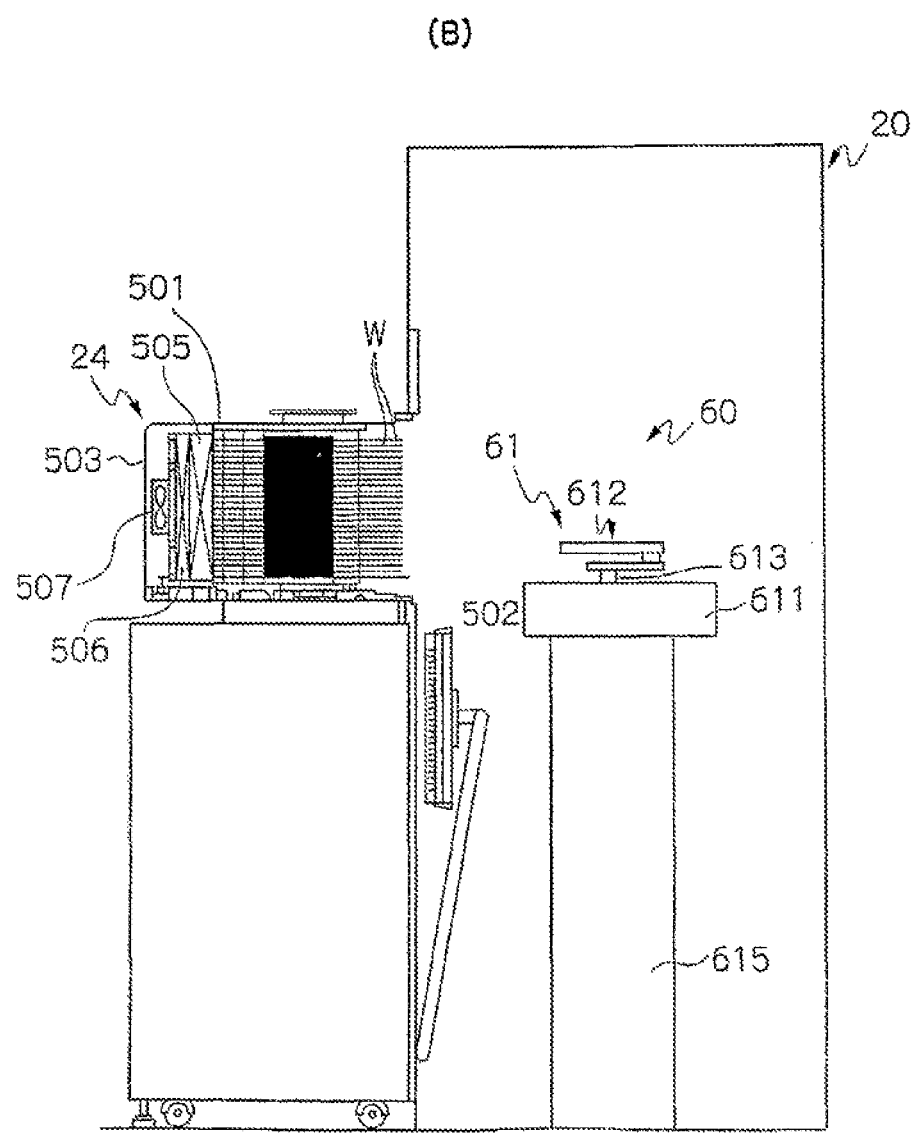
FIG. 2B is a schematic sectional view showing another embodiment of a substrate installation device of the inspection apparatus of the embodiment of the present invention.

In another embodiment, as shown in FIG. 2B, a plurality of 300 mm substrates are stored in groove pockets (not shown) fixed in a box main body 501 in a state of being accommodated, and then conveyed or stored. The substrate conveyance box 24 includes: a box main body 501 having a shape of a rectangular cylinder; a substrate conveyance door 502 that is connected to the box main body 501 and a device of automatically opening and closing the substrate conveyance door and can mechanically open and close an opening on a side of the box main body 501; a cover 503 that is disposed opposite to the opening and covers the opening through which filters and a fan motor is attached and detached; groove pockets (not shown) for storing substrates W; an ULPA filter 505; a chemical filter 506; and a fan motor 507. In this embodiment, the substrate is carried in and out by a robotic first conveyance unit 612 of the loader 60.

The substrates, or wafers, stored in the cassette c are to be inspected. The inspection is performed after or in a process on a wafer, in semiconductor manufacturing processes. More specifically, substrates, which are wafers, subjected to a film forming process, CMP, ion injection, etc., wafers on which wiring patterns are formed, or wafers on which wiring patterns have not been formed yet, are stored in the cassette. The wafers stored in the cassette c are arranged vertically separated and in parallel with each other. Accordingly, an arm of the after-mentioned first conveyance unit is configured to be vertically moved so as to hold the wafer at any position by the first conveyance unit.

Mini-Environment Apparatus

Figure 3:
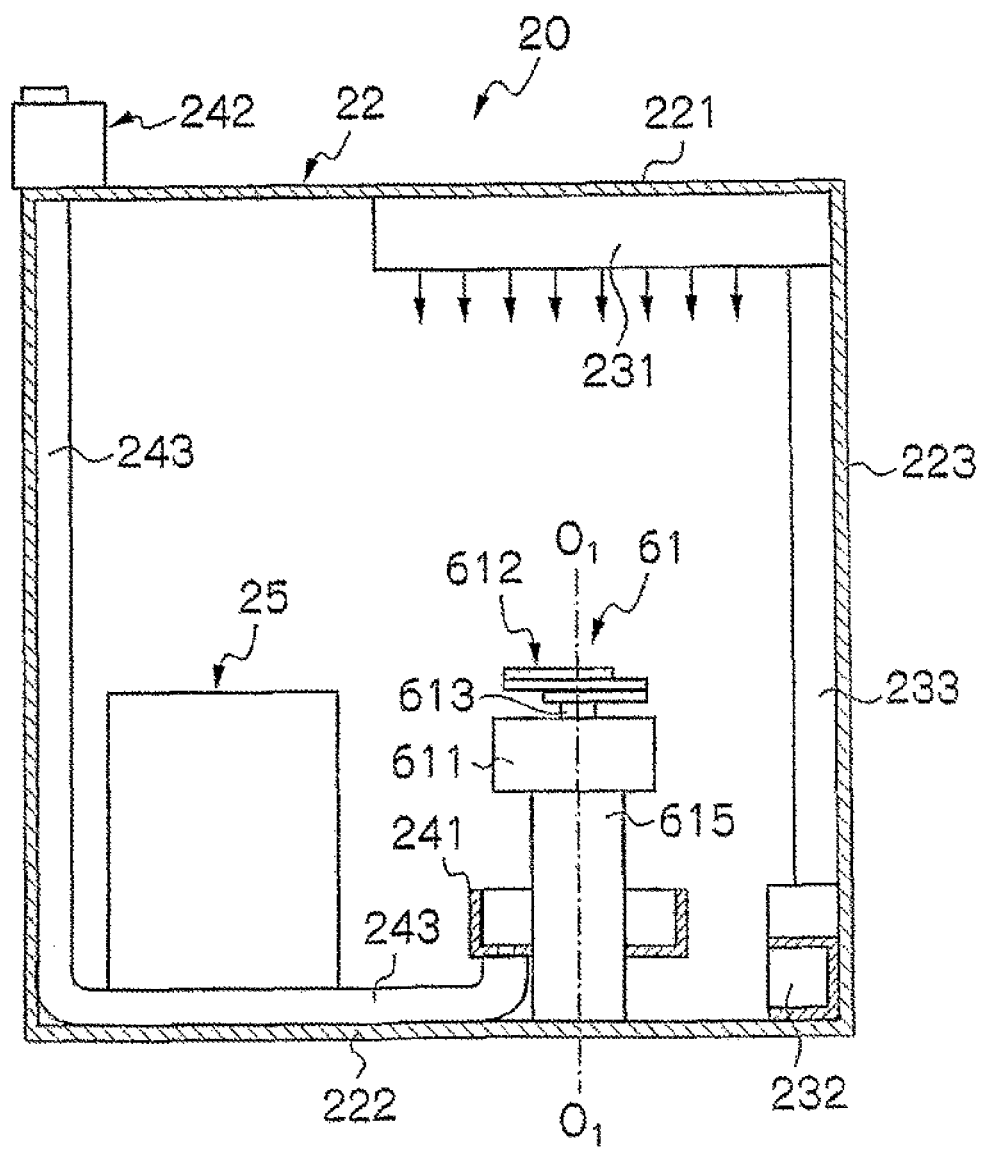
FIG. 3 is a sectional view showing a mini-environment device of FIG. 1 taken along line C-C.

In FIGS. 1 to 3, the mini-environment device 20 includes: a housing 22 that defines an atmosphere-controlled mini-environment space 21; a gas circulator 23 that circulates gas, such as cleaned air, to control an atmosphere in the mini-environment space 21; an evacuator 24 that collects and evacuates a part of air supplied in the mini-environment space 21; and a prealigner 25 that is disposed in the mini-environment space 21 and roughly positions a substrate as an inspection object, i.e., a wafer.

The housing 22 includes a top wall 221, a bottom wall 222, and surrounding walls 223 that surround the periphery, and thus has a structure that isolates the mini-environment space 21 from the outside. As shown in FIG. 3, in order to control the atmosphere in the mini-environment space, the gas circulator 23 includes: a gas supply unit 231 that is attached to the top wall 221 in the mini-environment space 21, cleans the gas (air in this embodiment), and flows the cleaned air as a laminar flow directly downward through one or more gas outlet (not shown); a collection duct 232 that is disposed on the bottom wall 222 in the mini-environment space, and collects the air having flown down toward the bottom; and a pipe 233 that communicates with the collection duct 232 and the gas supply unit 231, and returns the collected air to the gas supply unit 231. In this embodiment, the gas supply unit 231 captures about 20% of the air to be supplied, from the outside of the housing 22 and cleans the captured air. However, the ratio of the air captured from the outside is arbitrarily selected. The gas supply unit 231 includes a HEPA or ULPA filter that has a publicly known structure for creating cleaned air. The downward laminar flow of the cleaned air, i.e., the downflow, is supplied mainly so as to flow over a conveyance surface of the after-mentioned first conveyance unit disposed in the mini-environment space 21. The flow prevents dust that may possibly be caused by the conveyance unit from adhering to the wafer. Accordingly, the downflow nozzle is not necessarily disposed at a position near the top wall as shown in the figure. The nozzle may be disposed at any position above the conveyance surface of the conveyance unit. The air is not necessarily flown over the entire surface of the mini-environment space. In some cases, an ion wind is used as the cleaned air to secure cleanness. A sensor for observing the cleanness may be provided in the mini-environment space, and the apparatus can be shut down when the cleanness is degraded. A gateway 225 is formed at a portion of the surrounding wall 223 of the housing 22 that is adjacent to the cassette holder 10. A shutter device having a publicly known structure may be provided adjacent to the gateway 225 to shut the gateway 225 from a side of the mini-environment device. The downflow of the laminar flow formed adjacent to the wafer may have, for instance, a flow rate of 0.3 to 0.4 m/sec. The gas supply unit may be provided outside of the mini-environment space, instead of the inside of this space.

The evacuator 24 includes: an intake duct 241 disposed at a position below a wafer conveyance surface of the conveyance unit, at a lower part of the conveyance unit; a blower 242 disposed outside of the housing 22; and a pipe 243 that communicates with the intake duct 241 and the blower 242. The evacuator 24 sucks, into intake duct 241, the gas that flows around the conveyance unit and may contain dust that may possibly be caused by the conveyance unit, and evacuates the gas out of the housing 22 through the pipes 243 and 244 and the blower 242. In this case, the gas may be evacuated into an exhaust pipe (not shown) drawn adjacent to the housing 22.

The aligner 25 disposed in the mini-environment space 21 optically or mechanically detects an orientation flat (a flat part formed at the circumference of the circular wafer) formed at the wafer or one or more V-shaped notches formed at the circumference of the wafer, and preliminarily positions the wafer in the turning direction about the axis O-O of the wafer at an accuracy of about ±1 degree. The prealigner configures a part of a mechanism of determining the coordinates of an inspection object according to the invention described in claims, and functions to roughly position the inspection object. The prealigner itself may be a prealigner having a publicly known structure. Accordingly, description on the structure and operations is omitted.

Although not shown, a collection duct for the evacuator may be provided also at the lower part of the prealigner to evacuate air including dust ejected from the prealigner to the outside.

Main Housing

In FIGS. 1 and 2A, the main housing 30, which defines a working chamber 31, includes a housing main body 32. The housing main body 32 is supported by a housing supporter 33 mounted on a vibration isolating device, or a vibration isolator 37, disposed on a base frame 36. The housing supporter 33 includes a frame structure 331 configured into a rectangular shape. The housing main body 32, which is disposed and fixed onto the frame structure 331, includes a bottom wall 321 mounted on the frame structure, a top wall 322, surrounding walls 323 that are connected to the bottom wall 321 and the top wall 322 and surround the periphery, and isolates the working chamber 31 from the outside. In this embodiment, the bottom wall 321 is made of steel plates having a relatively large thickness not to cause distortion due to the weight of a device, such as a stage device, mounted on this wall. However, the bottom wall may have another structure. In this embodiment, the housing main body and the housing supporter 33 are configured to have rigid structures. The configuration allows the vibration isolator 37 to prevent vibrations of a floor on which the base frame 36 is installed from being transferred to the rigid structures. A gateway 325 through which a wafer is carried in and out is formed at a surrounding wall adjacent to the after-mentioned loader housing among the surrounding walls 323 of the housing main body 32.

The vibration isolator may be an active isolator having an air spring, a magnetic bearing or the like, or a passive isolator including these components. Each of the isolators may be an isolator having a publicly known structure. Accordingly, description on the structure and operations is omitted. The atmosphere in the working chamber 31 is kept in a vacuum atmosphere by a vacuum device (not shown) having a publicly known structure. A controller 2 that controls the operations of the entire apparatus is disposed at the bottom of the base frame 36.

Loader Housing

Figure 4:
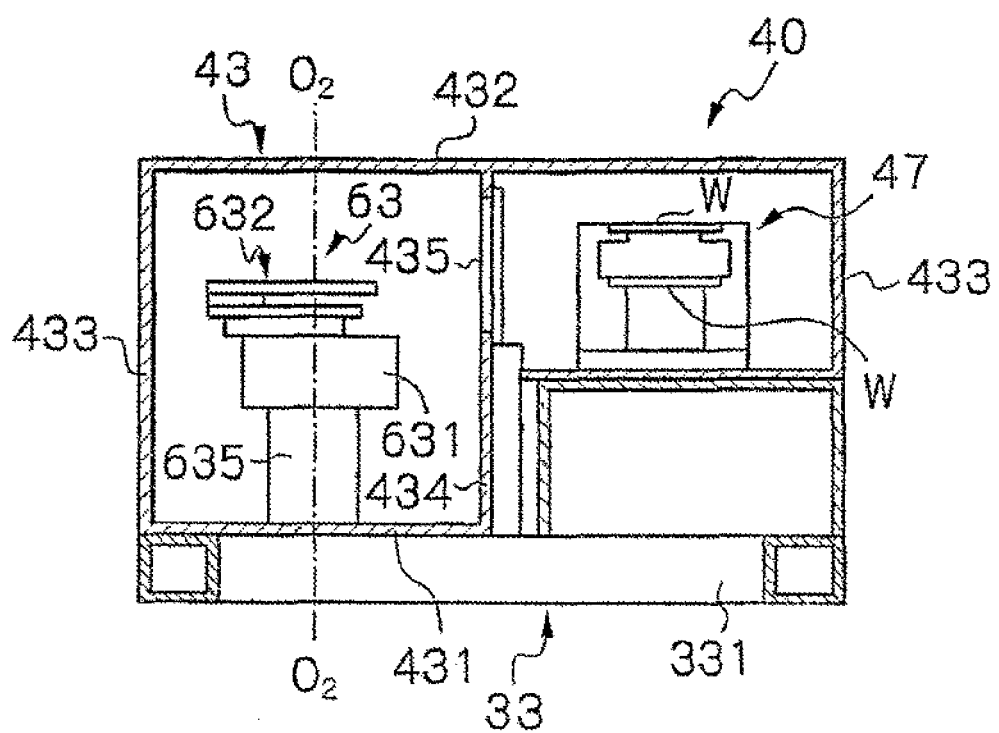
FIG. 4 is a diagram showing a loader housing of FIG. 1 taken along line D-D of FIG. 2.

In FIGS. 1, 2A and 4, the loader housing 40 includes a housing main body 43 that defines a first loading chamber 41 and a second loading chamber 42. The housing main body 43 includes a bottom wall 431, a top wall 432, surrounding walls 433 that surround the periphery, and a partition wall 434 that separates the first loading chamber 41 and the second loading chamber 42 from each other. The structure can separate both the loading chambers from the outside. An opening, or a gateway 435, through which a wafer is exchanged between both the loading chambers is formed at the partition wall 434. Gateways 436 and 437 are formed at portions of the surrounding walls 433 adjacent to the mini-environment device and the main housing. The housing main body 43 of the loader housing 40 is mounted on the frame structure 331 of the housing supporter 33, and supported by this structure. Accordingly, vibrations of the floor are not transmitted to loader housing 40 either. The gateway 436 of the loader housing 40 and the gateway 226 of the housing 22 of the mini-environment device match with each other. A shutter device 27 that selectively blocks communication between the mini-environment space 21 and the first loading chamber 41 is provided at the matching portion. The shutter device 27 includes: a seal member 271 that surrounds the gateways 226 and 436 and is in close contact with and fixed to the side wall 433; a door 272 cooperates with the seal member 271 to prevent the air from flowing through the gateways; and a drive device 273 that moves the door. The gateway 437 of the loader housing 40 and the gateway 325 of the housing main body 32 match with each other. A shutter device 45 is provided that selectively blocks communication between the second loading chamber 42 and the working chamber 31. The shutter device 45 includes: a seal member 451 that surrounds the gateways 437 and 325 and is in close contact with and fixed to the respective side walls 433 and 323; a door 452 that cooperates with seal member 451 to block communication of air through the gateways; and a drive device 453 that moves the door. Furthermore, a shutter device 46 that closes the door 461 to selectively seal and block communication between the first and second loading chambers is provided at an opening formed at the partition wall 434. In closed states, the shutter devices 27, 45 and 46 can hermetically seal the corresponding chambers. These shutter devices may be devices having a publicly known structure. Accordingly, detailed description on the structure and operations is omitted. The method of supporting the housing 22 of the mini-environment device 20 is different from the method of supporting the loader housing. In order to prevent vibrations of the floor from being transmitted to the loader housing 40 and the main housing 30 through the mini-environment device, a vibration isolating cushion member is preferably disposed between the housing 22 and the loader housing 40 so as to hermetically surround the gateway.

Figure 5:
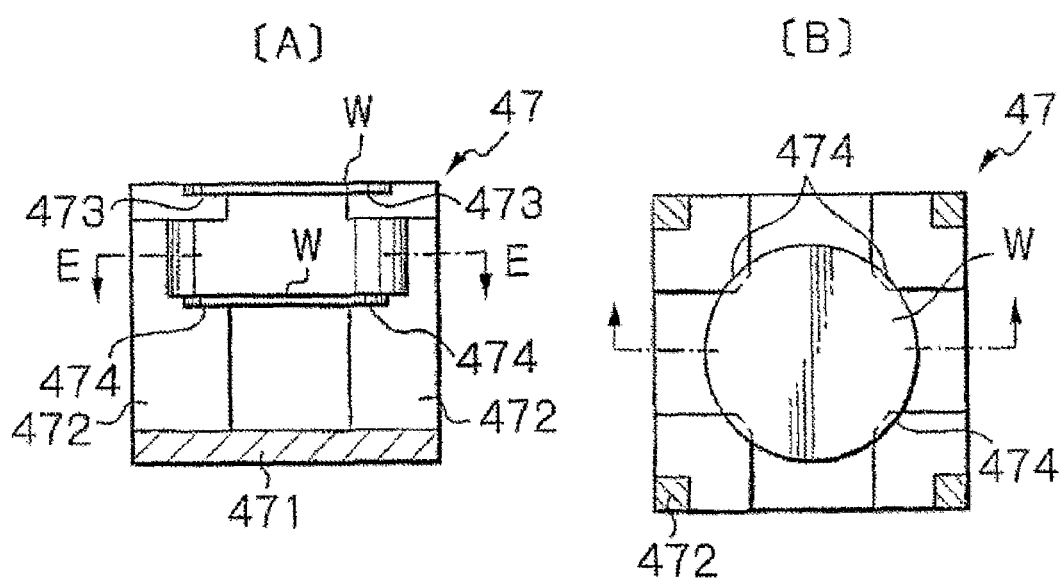
FIGS. 5A and 5B are enlarged views of a wafer rack.

A wafer rack 47 that vertically separates a plurality of (two in this embodiment) wafers and horizontally supports the wafers is arranged in the first loading chamber 41. As shown in FIGS. 5A and 5B, the wafer rack 47 includes pillars 472 fixed in a manner of being separated at the four corners of a rectangular substrate 471 in a state of standing upright. Two stages of supporters 473 and 474 are formed at each pillar 472. The periphery of the wafer W is mounted on the supporters, and thus the wafer is held. The distal ends of the arms of the after-mentioned first and second conveyance units are moved to approach the wafers between the adjacent pillars, and the arms hold the wafers.

The atmospheres of the loading chambers 41 and 42 can be controlled to a high vacuum (a degree of vacuum of $10^{-5}$ to $10^{-6}$ Pa) by a vacuum evacuator (not shown) that has a publicly known structure including a vacuum pump (not shown). In this case, the first loading chamber 41 may be kept in a low vacuum atmosphere and serve as a low vacuum chamber, and the second loading chamber 42 may be kept in a high vacuum atmosphere and serve as a high vacuum chamber. This structure can efficiently prevent wafer from being contaminated. Adoption of the structure can convey a wafer that is stored in the loading chamber and to be subjected to defect inspection at the next time, into the working chamber without delay. Adoption of such a loading chamber can improve the throughput of defect inspection, and achieve a degree of vacuum as high as possible around an electron source, which is required to be stored in a high vacuum state.

A vacuum exhaust pipe and a vent pipe for inert gas (e.g., dry pure nitrogen) (both the pipes are not shown) communicate to first and second loading chambers 41 and 42, respectively. According to this configuration, an atmospheric pressure state in each loading chamber can be achieved by the inert gas vent (inert gas is injected to prevent oxygen gas etc. other than inert gas from adhering to the surface). The device for such inert gas venting may be a device having a publicly known structure. Accordingly, the detailed description is omitted.

Stage Device

The stage device 50 includes: a fixed table 51 disposed on the bottom wall 321 of the main housing 30; a Y table 52 that moves in the Y direction (the direction perpendicular to the sheet of FIG. 1) on the fixed table; an X table 53 that moves in the X direction (the lateral direction in FIG. 1) on the Y table; a turn table 54 that can turn on the X table; and a holder 55 disposed on the turn table 54. A wafer is releasably held on a wafer-mounting surface 551 of the holder 55. The holder may be a holder that has a publicly known structure and can releasably grip a wafer mechanically or according to an electrostatic chuck system. The stage device 50 can highly accurately position a wafer held by the holder on the mounting surface 551, in the X direction, Y direction and the Z direction (the vertical direction in FIG. 1), and further in a direction (θ direction) about an axis perpendicular to the wafer holding surface, with respect to an electron beam emitted from the electronic optical device, by moving the tables using servomotors, encoders and various sensors (not shown). As to the positioning in the Z direction, for instance, the position of the mounting surface on the holder may preferably be slightly adjusted in the Z direction. In this case, the reference position of the mounting surface is detected by a position measuring instrument using fine diameter laser (a laser interferometric distance meter adopting the principle of an interferometer), and the position is controlled by a feedback circuit, not shown. Together with or instead of this control, the position of the notch or the orientation flat of the wafer is measured to detect the planar position and the turning position of the wafer with respect to the electron beam, and the positions are controlled by turning the turn table by a stepping motor or the like capable of fine angle control. In order to prevent dust from occurring in the working chamber as much as possible, servomotors 521 and 531 and encoders 522 and 532 for the stage device are disposed out of the main housing 30. The stage device 50 may be, for instance, a device used in a stepper or the like having a publicly known structure. Accordingly, detailed description on the structure and operations is omitted. The laser interferometric distance meter may be a meter having a publicly known structure. Accordingly, detailed description on the structure and operations is omitted.

The wafer turning position and the X and Y positions with respect to the electron beam are preliminarily input into an after-mentioned signal detection system or an image processing system to allow the signal to be standardized. Furthermore, a wafer chuck mechanism provided in the holder can apply a voltage for chucking a wafer to an electrode of an electrostatic chuck, and press three points on the circumference of the wafer (the points preferably separated by regular intervals in the circumferential direction) for positioning. The wafer chuck mechanism includes two fixed positioning pins, and one pressing crank pin. The clamp pin can achieve automatic chucking and automatic releasing, and configures a conduct part for voltage application.

In this embodiment, the table moving in the lateral direction in FIG. 2A is the X table, and the table moving in the vertical direction is the Y table. Instead, the table moving in the lateral direction may be the Y table, and the table moving in the vertical direction may be the X table in this diagram.

Loader

The loader 60 includes: a robotic first conveyance unit 61 disposed in the housing 22 of the mini-environment device 20; and a robotic second conveyance unit 63 disposed in the second loading chamber 42.

The first conveyance unit 61 includes a multi-axial arm 612 capable of turning about an axis $O_1$-$O_1$ with respect to a driver 611. The multi-axial arm may be an arm having any configuration. In this embodiment, the arm includes three parts attached in a manner capable of turning with respect to each other. A part of the arm 612 of the first conveyance unit 61, i.e., a first part nearest the driver 611, is attached to a shaft 613 that can be turned by a drive mechanism (not shown) that has a publicly known structure and provided in the driver 611. The arm 612 can be turned about the axis $O_1$-$O_1$ by the shaft 613, and extend and contract in the radial direction with respect to the axis $O_1$-$O_1$ as a whole by relative turning between the components. A distal end of a third part of the arm 612 that is most opposite to the shaft 613 is provided with a grip device 616 that has a publicly known structure, such as a mechanical chuck or electrostatic chuck, and grips a wafer. The driver 611 can be vertically moved by a lifting mechanism 615 having a publicly known structure.

The first conveyance unit 61 extends the arm 612 toward any one of directions M1 and M2 of the two cassettes c held by the cassette holder, mounts one wafer stored in the cassette c on the arm or grips the wafer using a chuck (not shown) attached to the distal end of the arm, and picks up the wafer. Subsequently, the arm is contracted (a state shown in FIG. 2A), turns to a position allowing the arm to extend in a direction M3 of the prealigner 25, and stops at this position. The arm then extends again, and mounts the wafer held by the arm on the prealigner 25. After the wafer is received from the prealigner in a manner inverted from the above description, the arm further turns and stops at a position allowing the arm to extend toward the second loading chamber 41 (direction M4), and exchanges the wafer with the wafer rack 47 in the second loading chamber 41. In the case of mechanically gripping the wafer, the peripheral portion of the wafer (a range within about 5 mm from the periphery) is grasped. This gripping manner is adopted because a device (circuit wiring) is formed on the entire surface except for the peripheral part of the wafer and gripping of this portion breaks the device and causes a defect.

The second conveyance unit 63 has a structure basically identical to the structure of the first conveyance unit. The structure is different only in that the wafer is conveyed between the wafer rack 47 and the mounting surface of the stage device. Accordingly, the detailed description is omitted.

In the loader 60, the first and second conveyance units 61 and 63 convey a wafer from the cassette held in the cassette holder onto the stage device 50 disposed in the working chamber 31 and convey a wafer in the inverse direction, in a state where the wafer is maintained in a horizontal orientation. The arm of the conveyance unit vertically moves only in the cases where the wafer is picked up from and inserted into the cassette, the wafer is mounted on and picked up from the wafer rack, and the wafer is mounted on and picked up from the storage device. Accordingly, even a large wafer, e.g., a wafer having a diameter of 30 cm, can be smoothly moved.

Wafer Conveyance

Next, conveyance of a wafer from the cassette c supported by the cassette holder to the stage device 50 disposed in the working chamber 31 will be sequentially described.

In the case of manually setting the cassette, the cassette holder 10 may be a holder having a structure suitable to the setting manner. In the case of automatically setting the cassette, the cassette holder 10 may be a holder having a structure suitable to the setting manner. In this embodiment, after the cassette c is set on the lifting table 11 of the cassette holder 10, the lifting table 11 is lowered by the lifting mechanism 12 to match the cassette c with the gateway 225.

After the cassette matches with the gateway 225, a cover (not shown) provided on the cassette opens. Furthermore, a cylindrical cover is disposed between the cassette c and the gateway 225 of the mini-environment. The configuration isolates the insides of the cassette and the mini-environment space from the outside. These structures are publicly known. Accordingly, detailed description on the structures and operations is omitted. In the case where a shutter device that opens and closes the gateway 225 is provided on the mini-environment device 20, the shutter device operates to open the gateway 225.

Meanwhile, the arm 612 of the first conveyance unit 61 stops in any of states of orientations in the directions M1 and M2 (the direction M1 in this direction). After the gateway 225 opens, the arm extends and receives one of the wafers stored in the cassette at the distal end of the arm. The vertical positions of the arm and the wafer to be picked up from the cassette are adjusted by vertically moving the driver 611 and the arm 612 of the first conveyance unit 61 in this embodiment. Instead, the movement may be achieved by vertically moving the lifting table of the cassette holder. Both movements may be adopted.

After the arm 612 has received the wafer, the arm is contracted. The gateway is closed by operating the shutter device (in the case with the shutter device). Next, the arm 612 comes into a state capable of extending in the direction M3 by turning about the axis $O_1$-$O_1$. The arm then extends and mounts, on the prealigner 25, the wafer mounted on the distal end of the arm or gripped by the chuck. The prealigner positions the orientation of the wafer in the turning direction (the direction about a central axis perpendicular to the wafer surface) within a prescribed range. After the positioning has been completed, the conveyance unit 61 receives the wafer from the prealigner 25 at the distal end of the arm and subsequently the arm is contracted to have an orientation allowing the arm to extend toward in the direction M4. The door 272 of the shutter device 27 then operates to open the gateways 226 and 436, the arm 612 extends to mount the wafer on the upper stage or the lower stage of the wafer rack 47 in the first loading chamber 41. As described above, before the shutter device 27 opens and the wafer is carried into the wafer rack 47, the opening 435 formed at the partition wall 434 is hermetically closed by the door 461 of the shutter device 46.

In the process of conveying the wafer by the first conveyance unit, cleaned air flows as a laminar flow (as a downflow) from the gas supply unit 231 provided on the housing of the mini-environment device. The flow prevents dust from adhering to the upper surface of the wafer during conveyance. A part of air around the conveyance unit (about 20% of air that is supplied from a supply unit and mainly dirty in this embodiment) is sucked from the intake duct 241 of the evacuator 24 and evacuated out of the housing. The remaining air is collected through the collection duct 232 provided at the bottom of the housing, and returned to the gas supply unit 231 again.

After the wafer is mounted in the wafer rack 47 in the first loading chamber 41 of the loader housing 40 by the first conveyance unit 61, the shutter device 27 is closed to seal the inside of the loading chamber 41. The inert gas is then charged in the first loading chamber 41 to evacuate the air, and subsequently the inert gas is also evacuated. The inside of the loading chamber 41 is thus in a vacuum atmosphere. The vacuum atmosphere of the first loading chamber may be a low degree of vacuum. After a certain degree of vacuum is achieved in the loading chamber 41, the shutter device 46 operates to open the gateway 434 having being hermetically closed with the door 461, the arm 632 of the second conveyance unit 63 extends, and receives one wafer from the wafer rack 47 by the grip device at the distal end (mounted on the distal end or gripped by the chuck attached to the distal end). After the wafer has been received, the arm is contracted, the shutter device 46 operates again, and the gateway 435 is closed with the door 461. Before the shutter device 46 opens, the arm 632 preliminarily becomes in an orientation capable of extending in the direction NI toward the wafer rack 47. As described above, before the shutter device 46 opens, the gateways 437 and 325 are closed with the door 452 of the shutter device 45, communication between the insides of the second loading chamber 42 and the working chamber 31 is blocked in a hermetical state, and the inside of the second loading chamber 42 is vacuum-evacuated.

After the shutter device 46 closes the gateway 435, the inside of the second loading chamber is vacuum-evacuated again to be in a degree of vacuum higher than the degree in the first loading chamber. Meanwhile, the arm of the second conveyance unit 61 turns to a position capable of extending in the direction toward the stage device 50 in the working chamber 31. On the other hand, in the stage device in the working chamber 31, the Y table 52 moves upward in FIG. 2A to a position where the center line $X_0$-$X_0$ of the X table 53 substantially matches with the X axis $X_1$-$X_1$ crossing the turning axis $O_2$-$O_2$ of the second conveyance unit 63. The X table 53 moves to a position approaching the left-most position in FIG. 2A. The tables are thus in a waiting state. When the second loading chamber becomes a state substantially identical to a vacuum state in the working chamber, the door 452 of the shutter device 45 operates to open the gateways 437 and 325, the arm extends, and thus the distal end of the arm holding the wafer approaches the stage device in the working chamber 31. The wafer is mounted on the mounting surface 551 of the stage device 50. After the wafer has been mounted, the arm is contracted, and the shutter device 45 closes the gateways 437 and 325.

The operations of conveying the wafer in the cassette c onto the stage device has been described above. However, the wafer mounted on the stage device and in a state where the processes have been completed is returned from the stage device to the cassette c according to inverted operations with respect to the aforementioned operations. Since the multiple wafers are mounted on the wafer rack 47, a wafer can be conveyed between the cassette and the wafer rack by the first conveyance unit during conveyance of a wafer between the wafer rack and the stage device by the second conveyance unit. Accordingly, the inspection process can be efficiently performed.

More specifically, in the case where a processed wafer A and an unprocessed wafer B are on the wafer rack 47 of the second conveyance unit, (1) first, the unprocessed wafer B is moved to the stage device 50, and the process is started, and (2) during the process, the processed wafer A is moved by the arm from the stage device 50 to the wafer rack 47, and the unprocessed wafer C is picked up from the wafer rack also by the arm, positioned by the prealigner, and subsequently moved to the wafer rack 47 of the loading chamber 41.

Thus, in the wafer rack 47, during the process on the wafer B, the processed wafer A can be replaced with the unprocessed wafer C.

According to certain usage of such an apparatus performing inspection or evaluation, multiple stage devices 50 may be arranged in parallel, and the wafer may be moved from one wafer rack 47 to each apparatus, thereby allowing multiple wafers to be subjected to the same process.

Figure 6:
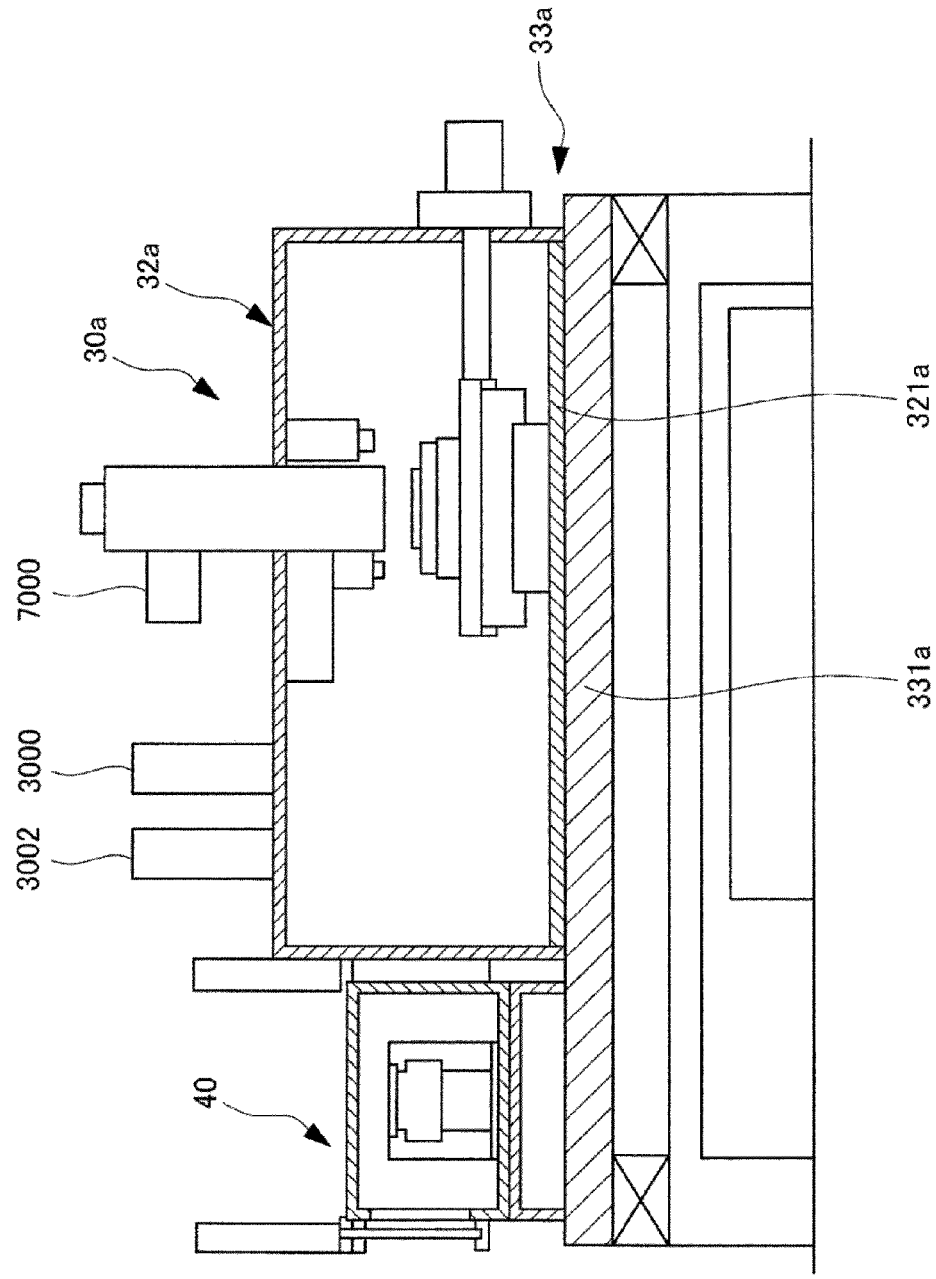
FIG. 6 is a diagram showing a variation of a method of supporting a main housing.

FIG. 6 shows a variation of a method of supporting a main housing. In the variation shown in FIG. 6, the housing supporter 33a includes a steel plate 331a that is thick and rectangular. A housing main body 32a is mounted on the steel plate. Accordingly, a bottom wall 321a of the housing main body 32a has a thinner structure than the bottom wall of the aforementioned embodiment. In a variation shown in FIG. 7, a housing main body 32b and a loader housing 40b are suspended and supported by a frame structure 336b of a housing supporter 33b. The bottom ends of multiple vertical frames 337b fixed to the frame structure 336b are fixed to the four corners of the bottom wall 321b of the housing main body 32b. The bottom wall supports surrounding walls and a top wall. Vibration isolators 37b are disposed between the frame structure 336b and the base frame 36b. The loader housing 40 is also suspended by a supporting member 49b fixed to the frame structure 336. In the variation of the housing main body 32b shown in FIG. 7, the support is achieved by suspension. Accordingly, in this variation, the centers of gravity of the main housing and all the devices provided in this housing can be lowered. The method of supporting the main housing and the loader housing, which includes the variations, prevents vibrations of the floor from being transmitted to the main housing and the loader housing.

In another variation, not shown, only the housing main body of the main housing may be supported by a housing supporting device from the lower side, and the loader housing may be disposed on the floor according to the same method as of the adjacent mini-environment device. In a still another variation, not shown, only the housing main body of the main housing may be supported by the frame structure in a suspending manner, and the loader housing may be disposed on the floor according to the same method as of the adjacent mini-environment device.

The embodiments can exert the following advantageous effects.

(A) The entire configuration of the mapping projection inspection apparatus that uses an electron beam can be acquired, and inspection objects can be processed at high throughput.

(B) In the mini-environment space, cleaned gas flows around the inspection object to prevent dust from adhering, and the sensors observing cleanness are provided. Thus, the inspection object can be inspected while dust in the space is monitored.

(C) The loading chamber and the working chamber are integrally supported via the vibration isolation device. Accordingly, the inspection object can be supplied to the stage device and inspected without being affected by the external environment.

Electronic Optical Device

Figure 8:
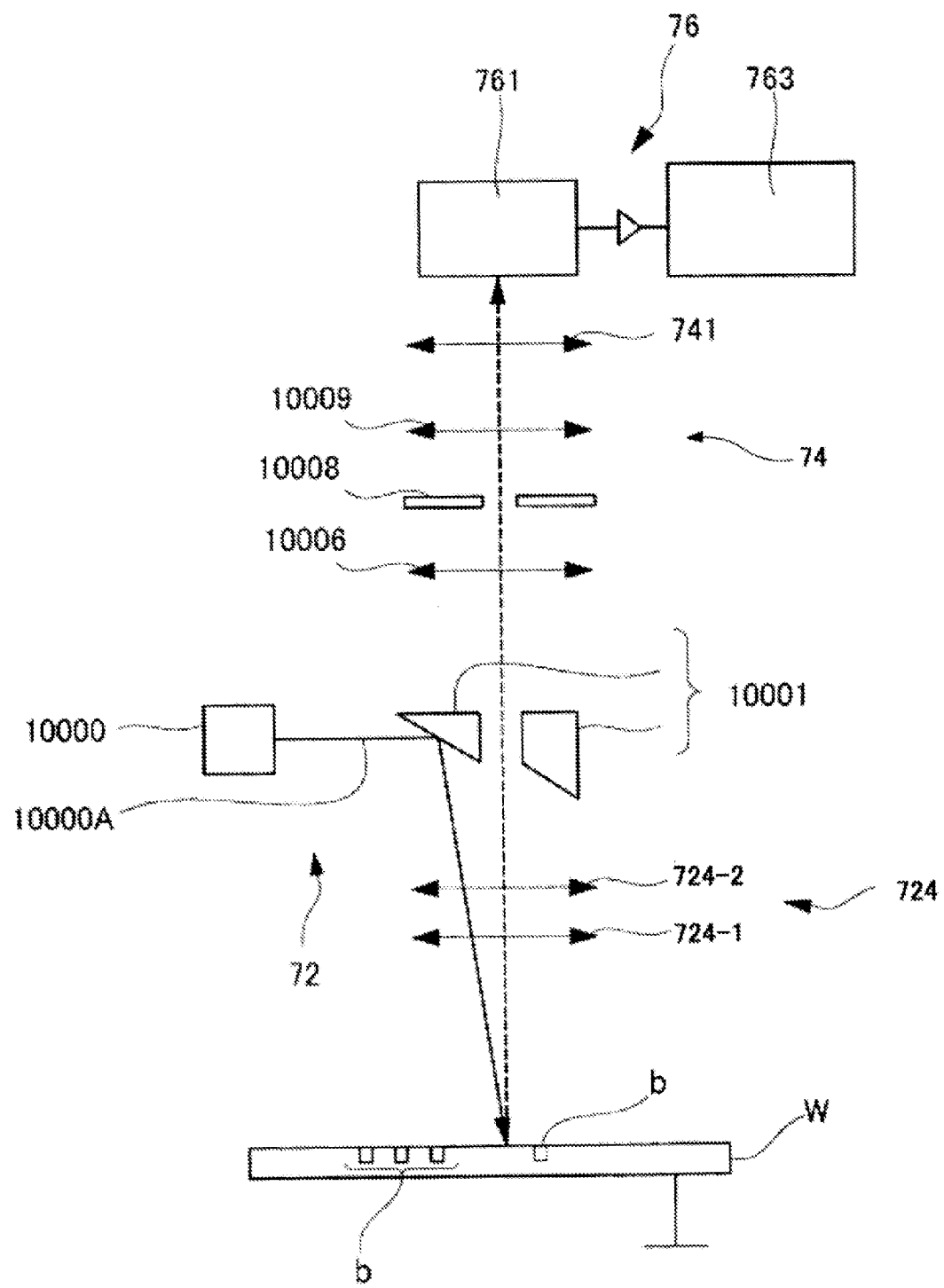
FIG. 8 is a schematic diagram showing an overview of a configuration of a light irradiation electronic optical device.

The electronic optical device 70 includes the lens tube 71 fixed to the housing main body 32. This tube internally includes: an optical system including a primary light source optical system (hereinafter, simply referred to as "primary optical system") 72 and a secondary electronic optical system (hereinafter, simply referred to as "secondary optical system") 74; and a detection system 76. FIG. 8 is a schematic diagram showing an overview of a configuration of a "light irradiation type" electronic optical device. The electronic optical device of this embodiment may be an after-mentioned "electronic irradiation type" electronic optical device. In the electronic optical device (light irradiation electronic optical device) in FIG. 8, a primary optical system 72, which is an optical system irradiating a surface of a wafer W as an inspection object with a light beam, includes a light source 10000 that emits the light beam, and a mirror 10001 that changes the direction of the light beam. In the light irradiation electronic optical device, the optical axis of the light beam 10000A emitted from the light source is inclined from the optical axis (perpendicular to the surface of the wafer W) of photoelectrons emitted from the wafer W, which is the inspection object.

The detection system 76 includes a detector 761 disposed on an imaging surface of a lens system 741, and an image processor 763.

Light Source (Light Beam Source)

In the electronic optical device in FIG. 8, a DUV laser light source is adopted as a light source 10000. The DUV laser light source 10000 emits DUV laser light. Another light source may be adopted that allows photoelectrons to emit from a substrate irradiated with light from the light source 10000, such as UV, DUV, and EUV light and laser, X-rays and X-ray laser.

Primary Optical System

An optical system where a light beam emitted from the light source 10000 forms a primary light beam, with which a surface of the wafer W is irradiated, forming a rectangular or circular (or elliptical) beam spot, is referred to as a primary optical system. The light beam emitted from the light source 10000 passes through an objective lens optical system 724, and the light beam serves as the primary light beam with which the wafer WF on the stage device 50 is irradiated.

Secondary Optical System

A two-dimensional image of photoelectrons caused by the light beam with which the wafer W is irradiated passes through a hole formed at the mirror 10001, is formed at a field stop position by electrostatic lenses (transfer lenses) 10006 and 10009 through a numerical aperture 10008, enlarged and projected by a lens 741 thereafter, and detected by the detection system 76. The image-forming projection optical system is referred to as a secondary optical system 74.

Here, a minus bias voltage is applied to the wafer. The difference of potentials between the electrostatic lens 724 (lenses 724-1 and 724-2) and the wafer accelerates the photoelectrons caused on the surface of the sample to exert an advantageous effect of reducing chromatic aberration. An extracted electric field in the objective lens optical system 724 is 3 to 10 kV/mm, which is a high electric field. There is a relationship where increase in extracted electric field exerts advantageous effects of reducing aberrations and improving resolution. Meanwhile, increase in extracted electric field increases voltage gradient, which facilitates occurrence of evacuated. Accordingly, it is important to select and use an appropriate value of the extracted electric field. Electrons enlarged to a prescribed magnification by the lens 724 (CL) is converged by the lens (TL1) 10006, and forms a crossover (CO) on the numerical aperture 10008 (NA). The combination of the lens (TL1) 10006 and the lens (TL2) 10009 can zoom the magnification. Subsequently, the enlarged projection is performed by the lens (PL) 741, and an image is formed on an MCP (micro channel plate) on the detector 761. In this optical system, NA is disposed between TL1-TL2. The system is optimized to configure an optical system capable of reducing off-axis aberrations.

Detector

A photoelectronic image from the wafer to be formed by the secondary optical system is amplified by the micro channel plate (MCP), subsequently collides with a fluorescent screen and converted into an optical image. According to the principle of the MCP, a prescribed voltage is applied using a hundred of significantly fine, conductive glass capillaries that are bundled to have a diameter 6 to 25 μm and a length of 0.24 to 1.0 mm and formed into a shape of a thin plate, thereby allowing each of the capillaries to function as independent electronic amplifier; the entire capillaries thus form an integrated electronic amplifier.

The image converted into light by the detector is projected on a TDI (time delay integration)-CCD (charge coupled device) by an FOP (fiber optical plate) system disposed in the atmosphere through a vacuum transmissive window in one-to-one mapping. According to another projection method, the FOP coated with fluorescent material is connected to the surface of a TDI sensor, and a signal electronically/optically converted in a vacuum may be introduced into the TDI sensor. This case has a more efficient transmittance and efficiency of an MTF (modulation transfer function) than the case of being arranged in the atmosphere has. For instance, the transmittance and MTF can be high values of ×5 to ×10. Here, the combination of the MCP and TDI may be adopted as the detector as described above. Instead, an EB (electron bombardment)-TDI or an EB-CCD may be adopted. In the case of adopting the EB-TDI, photoelectrons caused on the surface of the sample and forming a two-dimensional image is directly incident onto the surface of the EB-TDI sensor. Accordingly, an image signal can be formed without degradation in resolution. For instance, in the case of the combination of the MCP and TDI, electronic amplification is performed by the MCP, and electronic/optical conversion is performed by fluorescent material or a scintillator, and information on the optical image is delivered to the TDI sensor. In contrast, the EB-TDI and the EB-CCD have no component for electronic/optical conversion and no transmission component for optical amplification information and thus have no loss due to the component. Accordingly, a signal can be transmitted to the sensor without image degradation. For instance, in the case of adopting the combination of the MCP and TDI, the MTF and contrast are ½ to ⅓ of the MTF and contrast in the cases of adopting the EB-TDI and the EB-CCD.

In this embodiment, it is provided that a high voltage of 10 to 50 kV is applied to the objective lens system 724, and the wafer W is arranged.

Figure 9:
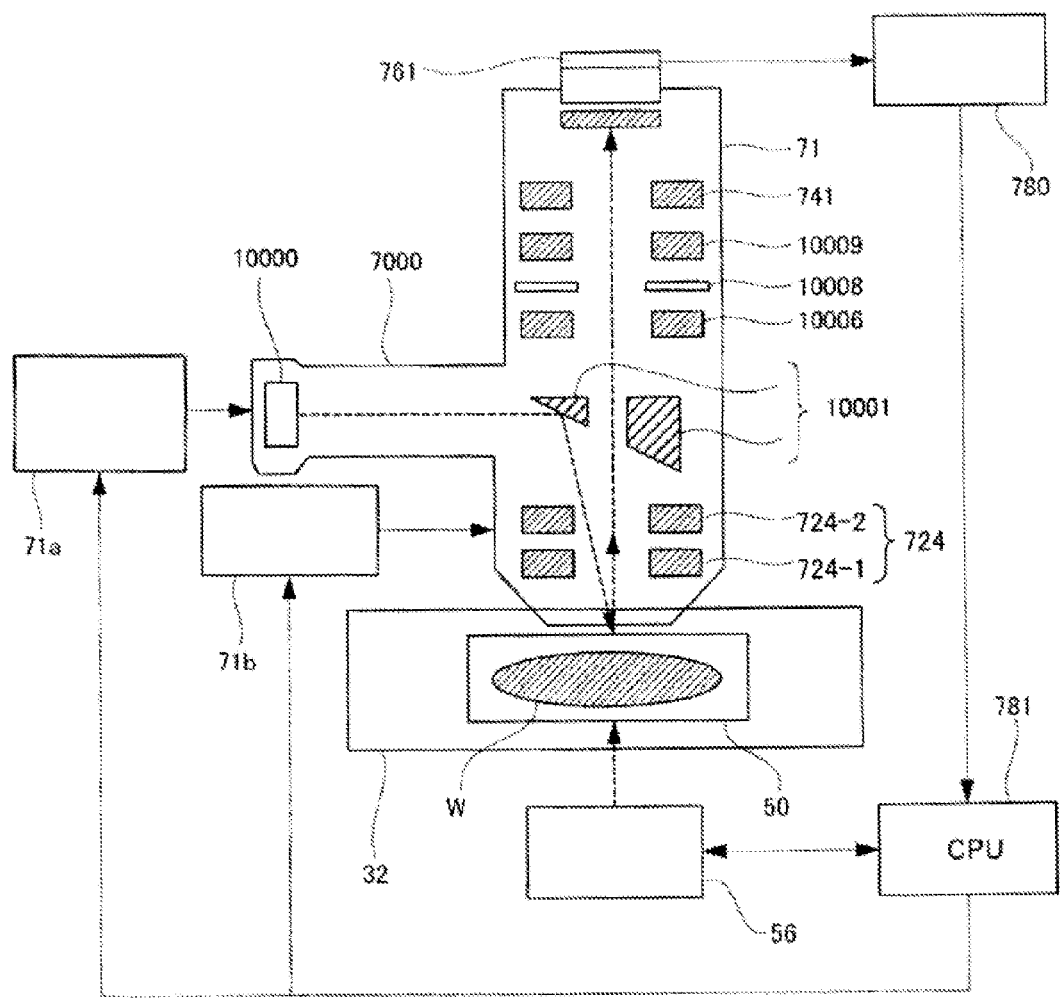
FIG. 9 is a diagram showing the entire configuration of the inspection apparatus according to an embodiment of the present invention.

Description on Relationship of Main Functions of Mapping Projection System and Overview FIG. 9 is a diagram showing the entire configuration of this embodiment. However, certain parts of components are abbreviated in the diagram.

In FIG. 9, the inspection apparatus includes the lens tube 71, a light source tube 7000, and a chamber 32. The light source 10000 is provided in the light source tube 7000. The primary optical system 72 is disposed on the optical axis of a light beam (primary light beam) emitted from the light source 10000. The stage device 50 is installed in the chamber 32. The wafer W is mounted on the stage device 50.

Meanwhile, the cathode lens 724 (724-1 and 724-2), the transfer lenses 10006 and 10009, the numerical aperture (NA) 10008, the lens 741 and the detector 761 are disposed on the optical axis of a secondary beam emitted from the wafer W, in the lens tube 71. The numerical aperture (NA) 10008 corresponds to an aperture stop, and is a thin plate that is made of metal (Mo. etc.) and has a circular hole.

The output of the detector 761 is input into a control unit 780. The output of the control unit 780 is input into a CPU 781. Control signals of the CPU 781 are input into a light source control unit 71a, a lens tube control unit 71b and a stage driving mechanism 56. The light source control unit 71a controls power supply to the light source 10000. The lens tube control unit 71b controls the lens voltages of the cathode lens 724, the lenses 10006 and 10009, and the lens 741, and the voltage of an aligner (not shown) (control of deflection).

The stage driving mechanism 56 transmits position information of the stage to the CPU 781. The light source tube 7000, the lens tube 71, and the chamber 32 communicate with a vacuum evacuation system (not shown). Air in the vacuum evacuation system is evacuated by a turbo pump of the vacuum evacuation system, and the inside of the chamber is kept in a vacuum. A rough evacuation system that typically adopts a dry pump or a rotary pump is disposed on a downstream side of the turbo pump.

When the sample is irradiated with the primary light beam, photoelectrons occur as the secondary beam from the surface of the wafer W irradiated with the light beam.

The secondary beam passes through the cathode lens 724, the group of TL lenses 10006 and 10009 and the lens (PL) 741, and is guided to the detector and formed as an image.

The cathode lens 724 includes three electrodes. It is designed such that the lowermost electrode forms a positive electric field with respect to the potential on the side of the sample W, and electrons (more specifically, secondary electrons having a small directivity) are extracted and efficiently guided into the lens. Thus, it is effective that the cathode lens is bi-telecentric. The secondary beam image-formed by the cathode lens passes through the hole of the mirror 10001.

If the secondary beam is image-formed by only one stage of the cathode lens 724, the effect of the lens is too strong. Accordingly, aberration easily occurs. Thus, the two stages of the doublet lens system are adopted for a formation of an image. In this case, the intermediate image formation position is between the lens (TL1) 10006 and the cathode lens 724. Here, as described above, the bi-telecentric configuration significantly exerts an advantageous effect of reducing the aberration. The secondary beam is converged on the numerical aperture (NA) 10008 by the cathode lens 724 and the lens (TL1) 10006, thereby forming a crossover. The image is formed between the lens 724 and lens (TL1) 10006. Subsequently, an intermediate magnification is defined by the lens (TL1) 10006 and the lens (TL2) 10009. The image is enlarged by the lens (PL) 741 and formed on the detector 761. That is, in this example, the image is formed three times as a total.

All the lenses 10006, 10009 and 741 are rotationally symmetrical lenses referred to as unipotential lenses or einzel lenses. The lenses have a configuration including three electrodes. Typically, the external two electrodes are zero potential, and control is performed by applying a voltage to the central electrode to exert a lens effect. The configuration is not limited to this lens configuration. Instead, the case of a configuration including a focus adjustment electrode on the first or second stage or both the stages of the lens 724, the case of including dynamic focus adjustment electrode and has a quadrupole or quintuple-pole configuration can be adopted. The field lens function may be added to the PL lens 741 to reduce off-axis aberrations, and a quadrupole or quintuple-pole configuration may effectively be adopted to increase the magnification.

The secondary beam is enlarged and projected by the secondary optical system, and image-formed on the detection surface of the detector 761. The detector 761 includes: the MCP that amplitudes electrons; a fluorescent plate that converts the electrons into light; a lens or another optical element for relaying an optical image between the vacuum system and the outside; and an image pickup element (CCD etc.). The secondary beam is image-formed on the MCP detection surface, and amplified. The electrons are converted into an optical signal by the fluorescent plate, and further converted into a photoelectric signal by an image pickup element.

The control unit 780 reads the image signal of the wafer W from the detector 761 and transmits the read signal to the CPU 781. The CPU 781 inspects defect on a pattern based on the image signal according to template matching or the like. The stage device 50 is movable in the XY direction by the stage driving mechanism 56. The CPU 781 reads the position of the stage device 50, outputs a drive control signal to the stage driving mechanism 56 to drive the stage device 50, thereby sequentially detecting and inspecting images.

As to change in magnification, even if a set magnification, which is lens conditions of the lenses 10006 and 10009, is changed, a uniform image can be acquired on the entire field of view on the detection side. In this embodiment, a uniform image without irregularity can be acquired. However, increase in magnification causes a problem of decreasing the brightness of the image. In order to solve the problem, the lens condition of the primary optical system is set such that the amount of emitted electrons per unit pixel is constant when the lens condition of the secondary optical system is changed to change the magnification.

Precharge Unit

As shown in FIG. 1, the precharge unit 81 is arranged adjacent to the lens tube 71 of the electronic optical device 70 in the working chamber 31. This inspection apparatus is an apparatus that inspects a device pattern and the like formed on the surface of the wafer by irradiating the substrate as the inspection object, i.e., wafer, with the electron beam. The information on the photoelectrons caused by irradiation with the light beam is information on the surface of the wafer. However, the surface of the wafer may be charged (charged up) according to conditions, such as a wafer material, the wavelength and energy of irradiation light or laser. Furthermore, a strongly charged spot and a weakly charged spot may occur on the surface of the wafer. If there is irregularity of the amount of charge on the surface of the wafer, the photoelectronic information also includes irregularity. Accordingly, correct information cannot be acquired. Thus, in this embodiment, to prevent the irregularity, the precharge unit 81 including a charged particles irradiation unit 811 is provided. Before a prescribed spot on the wafer to be inspected is irradiated with light or laser, charged particles are emitted from the charged particles irradiation unit 811 of the precharge unit to eliminate charging irregularity. The charging-up on the surface of the wafer preliminarily forms an image of the surface of the wafer, which is a detection object. Detection is performed by evaluating the image to operate the precharge unit 81 on the basis of the detection.

Embodiment 1

Electronic Optical Device Including Primary Optical System Using Electronic Irradiation Instead of Primary System Using Light Irradiation The mode has been described where the surface of the sample is irradiated with light, laser or the like, thereby causing photoelectrons from the surface of the sample. An embodiment of the present invention that is the "electronic irradiation type" primary system emitting electron beam instead of light will be described. FIGS. 10A and 10B show an example of an inspection apparatus including a typical electron gun. FIG. 10A shows the entire configuration. FIG. 10B shows an enlarged schematic diagram of the electron gun. However, certain parts of components are abbreviated in the diagram.

In FIG. 10A, the inspection apparatus includes a primary column 71-1, a secondary column 71-2, and a chamber 32. An electron gun 721 is provided in the primary column 71-1. The primary optical system 72 is disposed on the optical axis of the electron beam (primary beam) emitted from the electron gun 721. The stage device 50 is installed in the chamber 32, and the sample W is mounted on the stage device 50. Meanwhile, the cathode lens 724, a numerical aperture NA-2, a Wien filter 723, a second lens 741-1, a numerical aperture NA-3, a third lens 741-2, a fourth lens 741-3, and the detector 761 are disposed on the optical axis of the secondary beam occurring from the sample W in the secondary column 71-2. The numerical aperture NA-3 corresponds to an aperture stop, and is a thin plate that is made of metal (Mo. etc.) and has a circular hole. The numerical aperture NA-2 is disposed such that the opening is disposed at the convergence position of the primary beam and the focal point of the cathode lens 724. Accordingly, the cathode lens 724 and the numerical aperture NA-2 configure a telecentric electronic optical system. More specifically, in another case, the cathode lens 724 may be two-stage doublet lens where the first intermediate image formation point is formed on or around the E×B center to configure a bi-telecentric electronic optical system. This case can reduce aberrations in comparison with the single telecentric case and the non-telecentric case. Accordingly, a high resolution image forming of a wide-field-of-view two-dimensional electronic image can be achieved. That is, aberration can be ½ to ⅓.

The output of the detector 761 is input into the control unit 780. The output of the control unit 780 is input into the CPU 781. The control signal of the CPU 781 is input into the primary column control unit 71a, the secondary column control unit 71b and the stage driving mechanism 56. The primary column control unit 71a controls a lens voltage of the primary optical system 72. The secondary column control unit 71b controls lens voltages of the cathode lens 724 and the second lens 741-1 to fourth lens 741-3, and an electromagnetic field to be applied to the Wien filter 723. The stage driving mechanism 56 transmits the position information of the stage to the CPU 781. The primary column 71-1, the secondary column 71-2, and the chamber 32 are connected to the vacuum evacuation system (not shown), the air in the components is evacuated by a turbomolecular pump of the vacuum evacuation system to keep the insides of the components in a vacuum state.

Primary Beam

The primary beam from the electron gun 721 is subjected to the lens effect by the primary optical system 72, and enters the Wien filter 723. Here, a rectangular, circular flat, or curved surface (e.g., about r=50 μm) chip may be adopted as a chip for the electron gun. LaB6 capable of drawing large current is used. The primary optical system 72 may be a rotationally asymmetric quadrupole or eightfold-pole electrostatic (or electromagnetic) lens. This system can cause convergence and divergence in each of the X and Y axes, as with a lens referred to as a cylindrical lens. Two or three stages of the lenses may be adopted to optimize each lens condition, and the shape of a beam irradiation region on the surface of the sample can be adjusted to have any of rectangular and elliptical shapes without loss of irradiation electrons. More specifically, in the case of adopting the electrostatic lens, four cylindrical rods are adopted. The opposite electrodes are set to have the same potential, and have voltage characteristics reversed to each other. The quadrupole lens does not necessarily have a cylindrical shape. Instead, this lens may be a lens that is an electrostatic deflector and has a shape where a disk for typical use is divided into four. In this case, the lens can be minimized.

The trajectory of the primary beam, having passed through the primary optical system 72, is curved by a deflecting effect of the Wien filter 723. The Wien filter 723 only causes charged particles that satisfy the Wien condition E=vB to straightly travel, and curves the trajectories of the other charged particles, where the magnetic field is orthogonal to the electric field, and the electric field is E, the magnetic field is B, and the velocity of the charged particles is v. A force FB due to the magnetic field and a force FE due to the electric field are exerted on the primary beam, and the trajectory of the beam is curved. Meanwhile, the force FB and the force FE exert in respective different directions on the secondary beam. Accordingly, the forces cancel each other, thereby allowing the secondary beam to straightly travel as it is. The lens voltage of the primary optical system 72 is preset such that the primary beam forms an image at the opening of the numerical aperture NA-2. The numerical aperture NA-2 prevents a redundant part of the electron beam that might be scattered in the apparatus from reaching the surface of the sample, and prevents the sample W from being charged up and contaminated. The field aperture NA-2 and the cathode lens 724 (two-stage doublet lens, although not shown) configure a bi-telecentric electronic optical system. Accordingly, the primary beam, having passed through the cathode lens 724, is converted into a parallel beam, with which the sample W is irradiated uniformly and evenly. That is, illumination referred to as KOhler illumination in the optical microscope field is achieved.

Secondary Beam

Irradiation of the sample with the primary beam causes secondary electrons, reflected electrons or backscattering electrons, as the secondary beam, from the beam irradiation surface of the sample. Instead, at a certain irradiation energy, mirror electrons are formed. The secondary beam passes through the lens while being subjected to the lens effect of the cathode lens 724. The cathode lens 724 includes three or four electrodes. It is designed such that the lowermost electrode forms a positive electric field with respect to the potential of the side of the sample W, and electrons (more specifically, secondary electrons having a small directivity and mirror electrons) are extracted and efficiently guided into the lens. The lens effect is exerted by applying voltages to the first and second electrodes of the cathode lens 724 and setting the third electrode to the zero potential. Instead, the effect is exerted by applying voltages to the first, second and third electrodes and setting the fourth electrode to the zero potential. The third electrode in the four-electrode configuration is used for focus adjustment. Meanwhile, the numerical aperture NA-2 is disposed at the focal point of the cathode lens 724, i.e., the back focus position from the sample W. Accordingly, the flux of light of the electron beam from the off-center of the field of view (off-axis) is also converted into a parallel beam, and passes through the center position of the numerical aperture NA-2 without vignetting. The numerical aperture NA-3 serves as a role of suppressing the lens aberrations of the cathode lens 724, second lens 741-1 to fourth lens 741-3 with respect to the secondary beam. The secondary beam, having passed through the numerical aperture NA-2, straightly travels as it is and passes without being subjected to the deflecting effect of the Wien filter 723. Only electrons having a specific energy (e.g., secondary electrons, or reflected electrons, or backscattering electrons) can be guided to the detector 761 by changing the electromagnetic field applied to the Wien filter 723. With respect to the secondary beam, the cathode lens 724 is an important lens to determine the aberrations of the secondarily released electrons occurring from the surface of the sample. Accordingly, a large magnification is not expected. Thus, in order to reduce the aberrations, the lens is configured to have a bi-telecentric structure, as the cathode lens having the two-stage doublet lens structure. In order to reduce the aberrations (astigmatism etc.) occurring in the Wien filter, which is formed by E×B, an intermediately formed image is set on and around the E×B center. This setting exerts a great advantageous effect of suppressing increase in aberration. The beam is converged by the second lens 741-1 to form a crossover on and around the numerical aperture NA-3. The second lens 741-1 and the third lens 741-2 have a zoom lens function, which allows magnification control. At a stage after the lens, the fourth lens 741-3 is disposed to enlarge and form an image on the detector surface. The fourth lens has a five-lens structure. The first, third and fifth stages are set to GND. Positive high voltages are applied to the second and fourth stages to form a lens. In this state, the second stage has a field lens function, on and around which a secondary intermediate image is formed. At this time, off-axis aberrations can be corrected by the field lens function. The fourth lens function enlarges and forms an image. As described above, the image is formed three times as a total. Instead, the image may be formed by the cathode lens and the second lens 741-1 on the detection surface (twice as a total). All the second lens 741-1 to fourth lens 741-3 may be rotationally symmetrical lenses, which are referred to as unipotential lenses or einzel lenses. Each lens has a three-electrode configuration. Typically, while external two electrodes are set to the zero potential, a voltage applied to the central electrode exerts a lens effect for control. A field aperture FA-2 (not shown) may be disposed at the intermediate image formation point. The field aperture FA-2 is disposed on or around the second stage in the case where the fourth lens 741-3 is a five-stage lens. This aperture is disposed on or around the first stage in the case of a three-stage lens. As with a field stop of an optical microscope, the field aperture FA-2 restricts the field of view to a required range. However, in the case of an electron beam, the field aperture blocks a redundant part of the beam to prevent the detector 761 from being charged up and contaminated. The secondary beam is enlarged and projected by the secondary optical system, and image-formed on the detection surface of the detector 761. The detector 761 includes an MCP that amplifies electrons; a fluorescent plate that converts electrons into light; a lens or another optical element for relaying and transmitting an optical image between the vacuum system and the outside; and an image pickup element (CCD etc.). The secondary beam is image-formed on the MCP detection surface and amplified. The electrons are converted into an optical signal by the fluorescent plate, and further converted into a photoelectric signal by the image pickup element. The control unit 780 reads an image signal of the sample from the detector 761, and transmits the signal to the CPU 781. The CPU 781 inspects defect on a pattern based on the image signal according to template matching or the like. The stage device 50 is movable in the XY direction by the stage driving mechanism 56. The CPU 781 reads the position of the stage device 50, outputs a drive control signal to the stage driving mechanism 56 to drive the stage device 50, thereby sequentially detecting and inspecting images.

"Secondary charged particles" include a part or mixture of secondarily released electrons, mirror electrons, and photoelectrons. In the case of irradiation with electromagnetic waves, photoelectrons occur from the surface of the sample. When the surface of the sample is irradiated with charged particles, such as electron beam, "secondarily released electrons" occur from the surface of the sample, or "mirror electrons" are formed. The "secondarily released electrons" are caused by collision of an electron beam with the surface of the sample. That is, the "secondarily released electrons" are a part or mixture of the secondary electrons, the reflected electrons, and the backscattering electrons. "Mirror electrons" are the emitted electron beam that does not collide with the surface of the sample and is reflected in proximity to the surface.

As described above, in the inspection apparatus of this embodiment, the numerical aperture NA-2 and the cathode lens 724 configure the telecentric electronic optical system. Accordingly, the sample can be uniformly irradiated with the primary beam. That is, KOhler illumination can be easily achieved. As to the secondary beam, all parts of the main light beam from the sample W enter the cathode lens 724 perpendicularly (parallel to the lens optical axis), and pass through the numerical aperture NA-2. Accordingly, even peripheral light is not vignetted, and the image luminance around the periphery of the sample does not decrease. Variation in energy of electrons varies the image forming position; i.e., what is called chromatic aberration of magnification occurs (specifically, since the secondary electrons have a large variation in energy, the chromatic aberration of magnification is large). Arrangement of the numerical aperture NA-2 at the focal point of the cathode lens 724 can suppress occurrence of the chromatic aberration of magnification.

The enlarging magnification is changed after the beam passes through the numerical aperture NA-2. Accordingly, even if the lens conditions, i.e., set magnifications, of the third lens 741-2 and the fourth lens 741-3 are changed, a uniform image can be acquired on the entire plane of the field of view on the detection side. In this embodiment, a uniform image without irregularity can be acquired. Typically, a problem occurs in that increase in enlarging magnification decreases the brightness of the image. To solve the problem, the lens condition of the primary optical system such that, when the lens condition of the secondary optical system is changed to change the enlarging magnification, the effective field of view on the surface of the sample that is determined by the change has the same size as the size of the electron beam with which the surface of the sample is irradiated.

That is, increase in magnification reduces the field of view accordingly. However, the irradiation energy density of the electron beam is increased accordingly, which uniformly keeps the signal density of detected electrons and prevents the brightness of the image from decreasing even if the image is enlarged and projected by the secondary optical system. The inspection apparatus of this embodiment adopts the Wien filter 723 that curves the trajectory of the primary beam but allows the secondary beam to straightly pass. However, the configuration is not limited thereto. Instead, the inspection apparatus may have a configuration adopting a Wien filter that allows the trajectory of the primary beam to straightly pass but curves the trajectory of the secondary beam. In this embodiment, the rectangular beam is formed by the rectangular negative electrode and the quadrupole lens. The configuration is not limited thereto. For instance, a rectangular beam or an elliptical beam may be formed from a circular beam. Instead, a rectangular beam may be acquired by causing a circular beam to pass through a slit.

In this example, the two numerical apertures, or the numerical aperture NA-2 and the numerical aperture NA-3, are disposed. The numerical apertures can be selectively used according to the amount of irradiation electrons. If the amount of irradiation electrons onto the sample is small, e.g., 0.1 to 10 nA, an appropriate beam diameter of e.g. #30 to #300 μm is selected in order to allow the numerical aperture NA-2 to reduce the aberrations of the primary beam and the secondary beam. However, if the amount of irradiation electrons increases, the numerical aperture NA-2 may be charged up owing to adhesion of contamination to inversely degrade the image quality. In such a case, a relatively large diameter of the hole is selected, for instance, the hole of the numerical aperture NA-2 has a diameter of $\phi 500$ to $\phi 3000$ μm for use of cutting peripheral stray electrons. The numerical aperture NA-3 is used to define the aberration and transmittance of the secondary beam. The numerical aperture NA-3 is not irradiated with the primary beam. Accordingly, the aperture has a small amount of adhesion of contamination, thereby eliminating image degradation due to charging up. Thus, selection and use of the diameter of the numerical aperture according to the magnitude of the amount of irradiation current are significantly effective.

In the case of such a primary beam of electron irradiation, the semiconductor inspection apparatus 1 that adopts the electron gun as the primary optical system 72 of the electronic optical device 70 has a problem in that the energy width of electrons increases in the case of acquiring a large irradiation current. Referring to the drawings, description will be made in detail. FIG. 10B is a schematic diagram of the primary optical system 72 of the electronic optical device 70 including a typical electron gun 2300.

In the electron gun 2300, a heating power supply 2313 for generating thermoelectrons flows heated current into a cathode 2310. The acceleration voltage Vacc is applied to the cathode 2310 by an acceleration power supply 2314. Meanwhile, a voltage is applied to an anode 2311 so as to have a relatively positive voltage with respect to the cathode 2310, e.g., a voltage difference of 3000 to 5000 V. In the case where the cathode 2310 is set to −5000 V, the anode 2311 may be set to 0 V. The amount of emission is controlled by a voltage to be applied to a Wehnelt 2312. The voltage of the Wehnelt 2312 is superimposed to the acceleration voltage Vacc. For instance, the superimposed voltage: 0 to −1000 V. The larger the voltage difference from Vacc is, the smaller the amount of emission is. The smaller the voltage difference is, the larger the amount of emission is. The position of a crossover (first crossover: 1stCO) formed first by the Wehnelt voltage deviates in the axial direction accordingly. If the cathode center, the Wehnelt, and the anode center deviate, positional deviation also occurs in X and Y directions perpendicular to the Z-axis. The released emission is widened. Among these components, a field aperture FA2320 selects an effective beam and determines the beam shape. The transmittance for the emission at this time is typically 0.1 to 0.5%. For instance, at an emission of 5 μA, the irradiation current is 5 to 25 nA. Accordingly, an emission of 200 μA to 1 mA is required to acquire, e.g., an irradiation current of 1 μA. At this time, increase in emission increases the width of energy of electrons due to Boersch effect in a trajectory from the cathode to the first crossover, and from the first crossover to the field aperture FA. For instance, the width of energy increases from 1.2 eV to 10-50 eV at the FA position.

The energy width causes a problem especially at a low LE. The spread in the Z direction of the trajectory of electrons adjacent to the surface of the sample is widened. Description will be made on the basis of drawings. FIGS. 11A and 11B are diagrams showing the intensity (amount) of irradiation current of electron beam with which the surface of the sample is irradiated and the energy state, and the state of the beam with which the surface of the sample is irradiated. FIG. 11A shows the intensity of the irradiation current of the beam with which the surface of the sample is irradiated, and the energy state. FIG. 11B shows the state of the beam with which the surface of the sample is irradiated. A beam in the case where the energy of the irradiation current of the beam with which the sample is irradiated is optimal is a beam c. A beam in the case where the energy of the irradiation current of the beam is low is a beam a. A beam in the case where an energy of the irradiation current of the beam is the maximum is a beam b. A beam in the case where the energy of the irradiation current of the beam is high is a beam d. The relationship between the energy of the electron beam and the intensity (amount) of the irradiation current in a thermoelectrons formation system, such as LaB6, according to Maxwell distribution shows a distribution of FIG. 11A. At this time, as described above, the electron beams having characteristics due to energy height are beams a to d.

For instance, FIG. 11B shows the case where the beam d with a high energy correctly collides with the surface of the sample. At this time, the beam d collides with the surface and is not reflected (without mirror electron formation). Meanwhile, the beam c, the beam b, and the beam a are reflected at the respective reflection potential points. That is, mirror electrons are formed. The positions in the axial direction, i.e., Z positions, where the beam c, the beam b and the beam a having different energies are reflected are different from each other. A difference $\Delta Z$ in the Z position occurs. The larger the $\Delta Z$ is, the larger the blurring of the image formed by the secondary optical system is. That is, the mirror electrons formed at the same surface position cause positional deviation on the imaging surface. More specifically, as to the mirror electrons, deviation in energy causes the reflection point and the intermediate trajectory to deviate. Accordingly, the deviation causes large adverse effects. The same relationship holds in an image formed by the mirror electrons, or an image formed by the mirror electrons and secondarily released electrons. The larger the energy width of the irradiation electron beams, the larger the adverse effects are (increase in $\Delta Z$). Accordingly, existence of the primary beam with which the surface of the sample is irradiated in the state where the energy width decreases is significantly effective. What is invented therefor is the electron source and the primary optical system as shown in FIGS. 12 to 18, which will be described later. These configurational elements can not only reduce the energy width of the electron beam in comparison with the conventional configuration, but also significantly increase the transmittance of the beam of the primary system. Accordingly, the surface of the sample can be irradiated with large current having a narrow energy width. That is, the $\Delta Z$ can be small. Accordingly, the positional deviation on the imaging surface in the secondary optical system decreases, which can achieve low aberration, high resolution, large current, and high throughput. Typically, a thermoelectron type electron source (Gun) of LaB6 and the like have an energy width of about 2 eV in an electron generation portion. As the intensity of occurring current increases, the energy width further increases owing to the Boersch effect and the like according to Coulomb repulsion. For instance, if the emission current of the electron source is changed from 5 to 50 μA, the energy width increases, e.g., from 0.6 to 8.7 eV. That is, as the current value increases by a factor of ten, the energy width increases by a factor of fifteen. Furthermore, while the beam passes through the middle of the primary optical system, the energy width, such as the space charge effect, increases. In view of such characteristics, in order to allow the electron beam with a narrow energy width to reach the sample, increase in energy width in the electron source, and increase in emission current of the electron source by increasing the transmittance of the primary optical system are most important. Although there have been no means for achieving these features, the present invention achieves the features. Advantageous effects of the features will be described later in embodiments shown in FIGS. 12 to 18.

The intensity of the electron beam (in the case of a high intensity, the beam b) is not necessarily optimal for taking an image. For instance, if the distribution is an energy distribution according to the Maxwell distribution, the beam intensity (amount) is often at a part with a low energy (beam b). In this case, many beams have higher energies than the beam b has. Accordingly, in some cases, the image quality may be different from the qualities of the images formed by the beams. That is, in the case where the beam d collides with the sample and an image of the secondarily released electrons is formed, the beam b has a relatively low energy. Accordingly, the effect is low on the asperities of the surface of the sample and mirror electrons are easily formed. That is, the asperities of the surface and the potential difference are small, the mirror electron is formed, and an image with a low contrast as a whole in image quality or a glaring image is easily formed. Empirically, it is difficult to acquire an image with a high resolution. In particular, in the case where an oxide film is at the uppermost part of the surface, effects of the amount of electrons colliding with the surface are large. Accordingly, for instance, increase in emission (e.g., by a factor of ten) increases the energy width by a factor of ten or more in comparison with the case of low emission current. In this case, when the surface of the sample is irradiated with the electron beam with the same landing energy LE, the absolute amount of a portion that has a higher energy than the beam b has, e.g., the beam d, increases. Accordingly, charging up of the oxide film increases. The adverse effects of the charging up may disturb the trajectory and image forming conditions, and prevent a normal image from being taken. This problem is a factor of preventing the irradiation current from increasing. In such situations, the beam c (beam with the optimal energy) can be used that can reduce the amount of the beam d colliding with the surface of the sample, and suppress the variation in potential of the oxide film to be low. This use of the beam can suppress the amount of the beam colliding with the sample and acquire a stable image. Note that, as shown in FIG. 11A, the beam c has a lower intensity (amount) than the beam b has. If the beam c with the optimal energy can approach the beam b with the maximum intensity, the amount of electrons contributing to image formation can be increased accordingly, and increase the throughput. Thus, it is important that the energy width is set to narrow to reduce the electrons colliding with the surface of the sample. The present invention achieves this feature. The embodiments will be described with reference to FIGS. 12 to 18.

In FIG. 11B, as LE gradually increases, the beam d collides with the surface of the sample, and then the beam c collides. As the colliding electron beam increases, the secondarily released electrons caused by the increase, in turn, increases. A region in which such mirror electrons and secondarily released electrons are mixed is referred to as the transition region. When the entire primary beam collides with the surface of the sample, mirror electrons are eliminated, and only the secondarily released electrons remains. In the case of no colliding electrons, all the electrons are mirror electrons.

As the Wehnelt voltage is changed to change the emission, the position of the first crossover is also changed. Every time such changing, the aligner and lens on the downstream are required to be adjusted.

To support new technologies, semiconductor inspection requires defect inspection of a level of 10 nm, such as EUV mask inspection (inspection on a mask for extreme ultraviolet lithography) and NIL inspection (inspection on a mask for nanoimprint lithography). Thus, reduction in aberrations and increase in resolution are required in the semiconductor inspection apparatus.

In order to reduce aberrations and increase the resolution, it is particularly required to reduce the aberrations of the secondary optical system. Factors of degrading the mapping system are what is called energy aberration (also referred to as chromatic aberration) and coulomb blur. Thus, in order to improve aberration in the secondary optical system, it is required to increase acceleration energy in a short time period.

In order to solve such problems, the inventors have invented a primary optical system including a new photoelectron generator, and an electronic optical device including the primary optical system. The primary optical system adopts a light source emitting DUV light or DUV laser. However, the light source is not limited thereto. Instead, UV, EUV or X-ray sources may be adopted. The description will be made with reference to FIG. 12.

Figure 12:
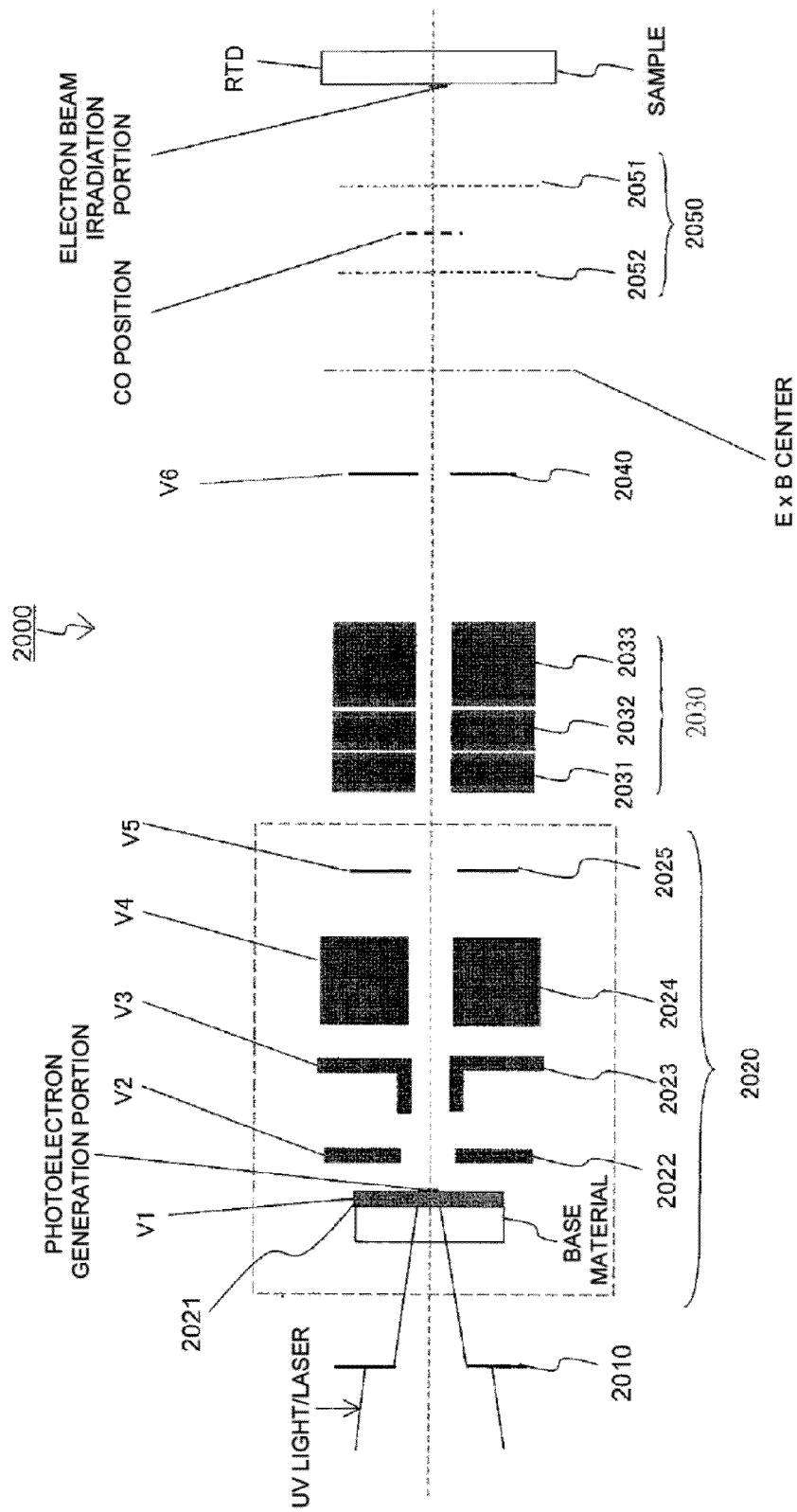
FIG. 12 is a diagram showing an example of a primary optical system using UV, EUV or X-rays, according to an embodiment of the present invention.

As shown in FIG. 12, in a schematic view, this primary optical system 2000 includes a light source (not shown), a field aperture (FA) 2010, a photoelectron generator 2020, an aligner 2030, an E×B deflector (Wien filter) (not shown), an aperture 2040, and a cathode lens (CL) 2050.

The field aperture 2010 is disposed between an after-mentioned photoelectronic surface 2021 of the photoelectron generator 2020 and the light source, and provided with a hole having a prescribed shape. Light or laser emitted from the light source toward the field aperture 2010 passes through the hole of the field aperture 2010. The photoelectronic surface 2021 is irradiated with the light or laser having a shape of the hole. That is, the light or laser emitted from the light source causes the photoelectronic surface 2021 to cause photoelectrons having a shape similar to the shape of the hole. The light source may be a light source emitting light or laser, such as DUV (deep ultraviolet rays), UV (ultraviolet rays), EUV (extreme ultraviolet rays), and X-rays, having a wavelength for generating photoelectrons. In this case, particularly, DUV light or laser having a wavelength of $\lambda \leq 270$ nm (i.e., $E \geq 2$ 4.7 eV) is preferably used.

The photoelectron generator 2020 configures one extraction lens that includes a photoelectronic surface 2021, and a three-stage extraction lens including a first stage lens 2022, a second stage lens 2023 and a third stage lens 2024. This generator further includes a numerical aperture 2025. The extraction lens may be a magnetic field lens or an electrostatic lens. In the case of adopting the magnetic field lens, a magnetic field corrector is provided around an after-mentioned numerical aperture 2025. The corrector may effectively be provided around the downstream of the field lens (not shown) of the secondary optical system or around an objective lens (not shown). In some cases, the image may be curved by adverse effects of a magnetic field. The corrector is provided to correct the curve. The number of stages of the extraction lens is not limited to this example.

The photoelectronic surface 2021 includes a base material made of an optical transmission material, such as sapphire or diamond, and a photoelectronic material coated thereon, and further includes a planar portion. The structure of the photoelectronic surface 2021 including the planar portion is also referred to as a planar cathode. In this case, particularly, materials with high thermal conductivities, such as sapphire and diamond, are preferably adopted as the base material of the photoelectronic surface 2021. The thermal conductivities of sapphire and diamond (sapphire: 30 to 40 W/(K·m), and diamond: 50 to 100 W/(K·m)) are higher than thermal conductivity of quartz or synthetic quartz (1 to 2 W/(K·m)). Accordingly, heat at a portion subjected to electronic irradiation can be quickly dispersed. Thus, damage to the photoelectronic surface 2021 can be reduced, and reduction in quantum efficiency and occurrence of inconsistency of quantum efficiency can be suppressed. Since the damage to the photoelectronic surface 2021 can be suppressed, the size of the spot of the electronic irradiation can be small (high power density), and the thickness of the photoelectronic material can be reduced. For instance, in the case where the base material is made of synthetic quartz, the quantum efficiency for irradiation onto the photoelectronic surface with CW laser that has a wavelength of 266 nm and at a power density of 8000 W/cm$^2$ is decreased to ⅕ of the quantum efficiency for irradiation with laser at a power density of 1000 W/cm$^2$. Meanwhile, in the case where the base material is made of sapphire, the quantum efficiency is not reduced. Not only natural but also artificial sapphire or diamond may be adopted. Materials having a low work function (materials with a high photoelectron generation efficiency), such as ruthenium and gold, are preferably adopted as the photoelectronic material. For instance, in this embodiment, the photoelectronic surface may be a surface where the base material is coated with a photoelectronic material, such as ruthenium or gold, having a thickness 5 to 100 nm, preferably, a thickness of 5 to 30 nm. As to the shape of the photoelectronic surface 2021, the diameter of the base material is, for instance, about 5 to 50 mm, and the photoelectronic material is coated in a central region of the base material. The coated region has, for instance, a diameter of 2 to 10 mm, and preferably a diameter of 3 to 5 mm. A conductive film made of Cr or the like is coated on a region outside of the photoelectronic material. A voltage can be applied to the photoelectric surface through the film. Furthermore, the Cr film has a transmittance for DUV laser, and shields irradiation onto irrelevant components to reduce noise occurring from the components. Cr has a photoelectron occurrence efficiency smaller in order-of-magnitude than the photoelectronic materials, such as Au and Ru, has. Accordingly, noise occurring therefrom also decreases.

The spot coated with the photoelectronic material is irradiated with DUV laser or the like. The spot has a shape of a disc having a diameter of 10 to 300 μm, preferably, 20 to 150 μm, or a shape of a rectangle having a side of 10 to 300 μm, preferably 10 to 150 μm. However, the scope of the present invention is not limited thereto. The light or laser is introduced through a view port of the base material, and reaches the photoelectric surface. On the photoelectric surface, photoelectrons occur.

The extraction lens (extraction electrode) including the first stage lens 2022, the second stage lens 2023, and the third stage lens 2024 performs functions that extract photoelectrons occur from the photoelectronic surface 2021 in the direction opposite to the light source and accelerate the extracted photoelectrons. Electrostatic lenses are adopted as these extraction lenses. The Wehnelt is not adopted as extraction lenses 2022, 2023 and 2024. The extracted electric field is constant. The first extraction electrode 2022, the second extraction electrode 2023 and the third extraction electrode 2024 preferably have a single telecentric or bi-telecentric configuration. This configuration is adopted because a significantly uniform extracted electric field region can be formed, and occurring photoelectrons can be transmitted at low loss.

Voltages applied to the respective extraction lenses are as follows. In the case where the voltage of the photoelectronic surface is V1, and the voltages of the first extraction electrode 2022, the second extraction electrode 2023 and the third extraction electrode 2024 are V2, V3 and V4, respectively, for instance, V2 and V4 are set to V1+3000 to 30000 V, and V3 is set to V4+10000 to 30000 V. However, the setting is not limited thereto.

The numerical aperture 2025 is disposed between the third extraction electrode 2024 of the photoelectron generator 2020 and an after-mentioned aligner 2030. The numerical aperture 2025 selects an effective beam in terms of the crossover formation position, the amount of beam, and aberrations.

The aligner 2030 includes a first aligner 2031, a second aligner 2032 and a third aligner 2033, and is used to adjust optical axis conditions. The first aligner 2031 and the second aligner 2032 are aligners performing static operations, and functions as tilting and shifting used for adjusting the optical axis conditions. Meanwhile, the third aligner 2033 is an aligner used in the case of high speed operations by the dynamic deflector, and, for instance, used for dynamic blanking operations.

At the downstream of the aligner 2030 (on the sample side; hereinafter, the light source side is referred to as upstream, and the sample side is referred to as downstream, in the positional relationship with each component), the aperture 2040 is disposed. The aperture 2040 is used to receive a beam during blanking, cut stray electrons, and center the beam. The amount of electron beam can be measured by measuring absorption current in the aperture 2040.

An E×B region that intersects with the secondary optical system is at the downstream of the aperture 2040. An E×B deflector (Wien filter) (not shown) is provided in this region. The E×B deflector deflects the primary electron beam such that the optical axis is perpendicular to the surface of the sample.

The cathode lens 2050 is provided at the downstream of the E×B region. The cathode lens 2050 is a lens where both the primary optical system and the secondary optical system are included. The cathode lens 2050 may include two stages of a first cathode lens 2051 and a second cathode lens 2052, or have single stage configuration. In the case where the cathode lens 2050 has the two-stage configuration, a crossover is formed between the first cathode lens 2051 and the second cathode lens 2052. In the case where the cathode lens has the single stage configuration, a crossover is formed between the cathode lens 2050 and the sample.

The amount of photoelectrons is defined by the intensity of light or laser with which the photoelectronic surface is irradiated. Accordingly, this primary optical system 2000 may adopt a system of adjusting the output of a light source or a laser light source. Although not shown, an output adjusting mechanism, for instance, an attenuator, a beam separator and the like, may further be provided between the light source or the laser light source and the base material.

For instance, in this embodiment, aging procedures may be performed when the electronic irradiation is performed. The aging procedures are sequentially performed as follows. First, (1) electronic irradiation with a large beam size (1 to 2 mm) is performed for five hours. Next, (2) electronic irradiation with an intermediate beam size (100 to 300 μm) is performed for two hours. Subsequently, (3) electronic irradiation with a small beam size (10 to 100 μm) is performed. The procedures can remove dust and contamination adhering to the photoelectronic surface, and provide thermal stable conditions. The dust and contamination adhering to the photoelectronic surface are, for instance, carbon, hydrocarbon, moisture and the like. Formation of thermal stable conditions can achieve uniformity in thermal conditions, and reduce damage to the photoelectronic surface in the case of increase in heat. The beam size in (3) is a size (size for use) in the case of use as the photoelectronic source. Accordingly, the beam size in (2) is a beam size 3 to 10 times as large as the size for use. The beam size in (1) can be regarded as a beam size 500 to 1000 time as large as the size for use.

Figure 13:
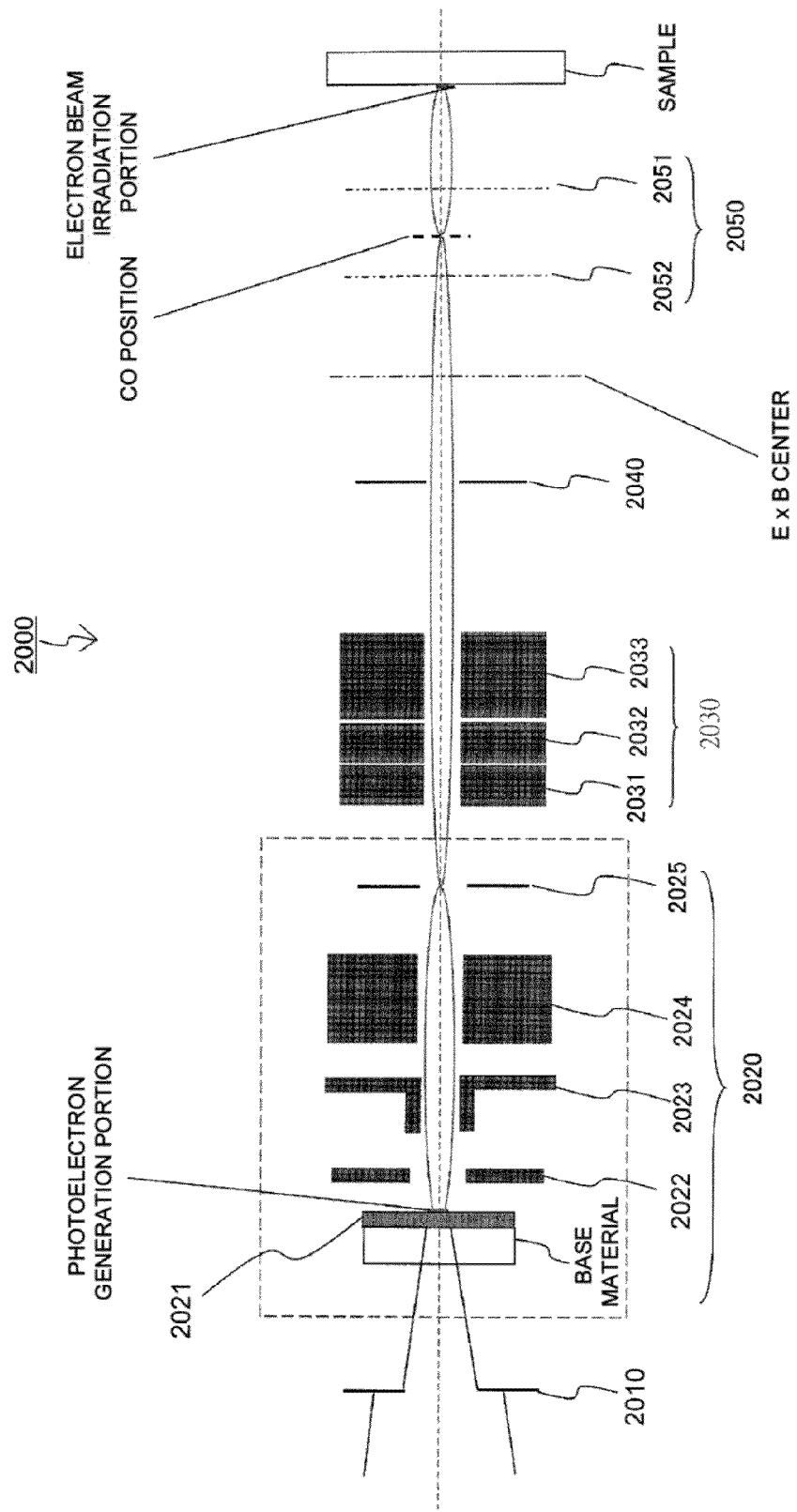
FIG. 13 is a schematic diagram of crossover formation of the primary optical system according to an embodiment of the present invention.

Formation of a crossover of in the primary optical system 2000 according to the present invention will be described with reference to the drawings. FIG. 13 is a schematic diagram of formation of the crossover in the primary optical system 2000 according to the invention of this application. In FIG. 13, it is schematically represented such that the sample is perpendicularly irradiated with photoelectrons occurring on the photoelectronic surface. However, in actuality, deflection is performed by the E×B deflector.

As shown in FIG. 13, the photoelectronic surface 2021 is irradiated with light or laser light through the field aperture 2010 from the light source or laser light source. Thus, photoelectrons occurring from the photoelectronic surface 2021 form a first crossover at the position of the numerical aperture 2025, pass through the aperture 2040, are deflected perpendicularly to the sample by the E×B deflector, and form a crossover between the first cathode lens 2051 and the second cathode lens 2052. The surface of the sample is irradiated with the photoelectrons forming the crossover as a planar beam. Accordingly, the electron release shape of the photoelectronic surface 2021 is conjugate with the shape of the electron beam with which the surface of the sample is irradiated. Meanwhile, as shown in FIG. 10B, in the primary optical system including a typical electron gun, photoelectrons emitted from the cathode 2310 form the first crossover between the cathode 2310 and the anode 2311, and pass through the anode 2311 and the field aperture 2320; the surface of the sample is irradiated with the photoelectrons. Accordingly, the shape of the field aperture 2320 is conjugate with the shape of the electron beam with which the surface of the sample is irradiated.

Setting of the applied voltages in the primary optical system 2000 according to the invention of this application will be described. The invention of this application has a configuration different from the configuration of a typical electron gun. The photoelectronic surface 2021 is irradiated with the light or laser, and occurring photoelectrons are extracted by the extraction lens on the latter stage and accelerated. Acceleration is performed by a uniform electric field without a Wehnelt and a suppressor. Accordingly, setting of the voltages applied to the respective configurational components is different from the setting of the typical electron gun.

Referring to FIG. 12, description will hereinafter be made. Voltages applied to the respective configurational components are set as follows. The voltage of the photoelectronic surface 2021 is V1. The voltages of electrodes configuring the extraction lens are set such that the voltage of the first extraction electrode 2022 is V2, the voltage of the second extraction electrode 2023 is V3, the voltage of the third extraction electrode 2024 is V4, the voltage of the numerical aperture 2025 is V5, and the voltage of the aperture 2040 is V6. A wafer surface voltage (also referred to as retarding voltage) is RTD. In the primary optical system 2000 of the invention of this application, according to representation with reference to the voltage V1 of the photoelectronic surface 2021, the voltages are applied to the respective configurational components as follows. That is, in the case of a low LE, V1=RTD−10 V to RTD+5 V. V2, V4=V1+3000 to 30000 V. V3=V4+10000 to 30000 V. V5, V6=reference potential. In one embodiment of the primary optical system according to the invention of this application, setting is made such that RTD=−5000 V, V1=−5005 V, V2, V4=GND, and V3=+20000V. Such voltage application can achieve high throughput at a low LE and a high resolution. However, this configuration is one example. Voltage application to the configurational components is not limited thereto.

In the case where the reference potential is represented as V0, and the voltage of the surface of the detector on which electrons are incident is represented as DV, application voltage relationship with RTD in the primary optical system 2000 according to the invention of this application is preferably setting shown in Table 1.

[Table 1]

The primary optical system 2000 according to the invention of this application that includes the aforementioned configuration, and the electronic optical device including the primary optical system 2000 according to the invention of this application can exert the following advantageous effects.

First, the primary optical system 2000 of the invention of this application can achieve a significantly high transmittance. The transmittance is 5 to 50%. A transmittance can be secured that is 10 to 100 times as high as the transmittance of 0.1 to 0.5% of the primary optical system including a typical electron gun. This achievement is made because, first, the configuration of the planar cathode surface and the new extraction lens can form a significantly uniform extracted electric field region to transmit occurring photoelectrons at low loss. Even with increase and decrease in the amount of occurring photoelectrons, this configuration can achieve a constant extracted electric field distribution, thereby achieving stable operations at a high transmittance. A primary optical system including a typical electron gun requires a Wehnelt or a suppressor mechanism. Accordingly, the amount of occurring electrons, i.e., the amount of emission, changes the electric field distribution, the uniform extracted electric field portion is reduced, and the effective beam region is reduced. It is therefore difficult to increase the transmittance. In contrast, the primary optical system 2000 according to the invention of this application does not require the Wehnelt and the suppressor mechanism, and can increase the transmittance. Second, in the primary optical system 2000 according to the invention of this application, the position of the first crossover is at the downstream of the lens. Accordingly, the numerical aperture and the like can be easily arranged. Thus, the optical system that can easily reduce the aberrations of the beam and the Boersch effect can be achieved. In the primary optical system including a typical electron gun, the position of the first crossover is in proximity to the Wehnelt. Accordingly, it is difficult to arrange the numerical aperture and the like at the position. Since the position deviates due to emission, effective use is difficult even if the numerical aperture and the like can be arranged at this position. In the primary optical system 2000 according to the invention of this application, the position of the first crossover can be disposed at the downstream of the lens. Accordingly, the problem can be solved.

Second, the primary optical system 2000 according to the invention of this application can achieve high throughput at high resolution. As described above, a high transmittance is achieved. Accordingly, only a significantly small amount of cathode release current intensity of 2 to 10 μA is sufficient to achieve high throughput, i.e., the amount of electronic irradiation of 1 μA. Accordingly, a significantly small Boersch effect is sufficient. For instance, at the position of the numerical aperture, the energy width is 0.5 to 1.2 eV. Thus, the amount of electronic irradiation can be increased with a small energy width. The positional deviation of the beam image-formed in the secondary optical system is small, and a high resolution can be maintained. As a result, a high throughput can be achieved at high resolution.

Third, the primary optical system 2000 according to the invention of this application can maintain the optical system in an always stable state. This feature is achieved because the primary optical system 2000 according to the invention of this application does not cause positional deviation of the first crossover.

Next, advantageous effects of the electronic optical device including the primary optical system 2000 according to the invention of this application will be described later.

First, since the primary optical system 2000 having the aforementioned configuration is used, the shape of the electron beam with which the surface of the sample is irradiated is set to have magnification×10 to ×0.1 with respect to the electron release shape of the photoelectronic surface. In particular, since use of a scale of magnification×1 or less is allowed, which negates the need of reduction in size of the photoelectronic surface, and can suppress the occurring photoelectron density to be low. Accordingly, the electronic optical device of the primary optical system 2000 according to the invention of this application can reduce the Boersch effect, and suppress the spread of energy width.

Second, as to the axial center of the electron generation portion of the photoelectronic surface, a photoelectron generation portion can be easily formed at the center position formed by the extraction lens. This feature can be achieved by irradiating the axial center position with the light or laser. Although FIGS. 12 and 13 do not show the position of the light source, the feature can be achieved by using a lens or a mirror irrespective of the position of the light source. The primary optical system 2000 according to the invention of this application is disposed in the lens tube fixed to the main housing. However, light or laser is used to generate photoelectrons. Accordingly, the light source is not necessarily disposed in the lens tube. For instance, the light source may be disposed outside of the lens tube, and the light or laser can be guided by a mirror, a lens and the like to the axial center of the electron generation portion of the photoelectronic surface. Since the light source can thus be disposed on the atmosphere side, the electronic optical device adopting the primary optical system 2000 according to the invention of this application can easily adjust the center position. In the inspection apparatus adopting a typical electron gun shown in FIG. 10B, the center positions of the cathode 2310, the Wehnelt 2312, the anode 2311 and the field aperture 2320 deviate from each other by assembly. Furthermore, positional deviation due to baking, which is performed after opening to the atmosphere occurs. That is, positional variation after assembly caused by being subjected to thermal expansion and cooling processes due to variation in temperature also occurs. In order to correct the deviation, a normal aligner is provided at the upstream of the field aperture 2320, and correction is performed by the aligner. If the positional deviation is large, repetition of disassembly, assembly, adjustment, and baking is required. Meanwhile, in the electronic optical device including the primary optical system 2000 according to the invention of this application, only irradiation onto the axial center position with light or laser can easily form the photoelectron generation portion at the center position formed by the electrostatic lens. Accordingly, adjustment is easily performed even if assembly causes deviation. Furthermore, the light source can be disposed on the atmosphere side. Accordingly, the configuration is resistant to occurrence of positional variation after assembly, and adjustment can easily be performed even if positional deviation occurs after assembly. Thus, operation procedures can be significantly reduced, and the cost can be reduced. Furthermore, the field aperture 2010 that defines the electron generation shape on the photoelectronic surface can be disposed on the atmosphere side. Accordingly, the field aperture 2010 can be easily replaced. Also in this point, the operation procedures can be significantly reduced, and the cost is reduced. In the case where the field aperture is disposed on the vacuum side, replacement requires operations, such as vacuum break, disassembly of the column, assembly, adjustment, vacuum disposal, baking, and optical axis adjustment. The above feature can be achieved by eliminating these operations.

Third, the electronic optical device including the primary optical system 2000 according to the invention of this application improves flexibility in beam size. The electron generation shape on the photoelectronic surface is defined by the field aperture 2010. Accordingly, not only a circular or rectangular shape but also an oblong or a shape asymmetric with respect to the axis may be allowed. The inspection apparatus including primary optical system 2000 according to the present invention allows, for instance, a circular shape with #100 µm on the photoelectronic surface and a circular shape with 450 µm to 100 µm on the surface of the sample, and a rectangular shape with 100×100 µm on the photoelectronic surface and a rectangular shape with 50×50 µm to 100×100 µm on the surface of the sample.

Fourth, the electronic optical device including the primary optical system 2000 according to the invention of this application can significantly reduce the number of components residing in a vacuum. In the electronic optical device including a typical electron gun, an aligner is required in front of the field aperture 2320 shown in FIG. 10B to correct deviation in the cathode center, the Wehnelt, the anode, and the field aperture center. Furthermore, a one-to-three-stage lens is required to form an image of the beam shape formed by the field aperture 2320, on the surface of the sample. Accordingly, the electronic optical device including the primary optical system 2000 according to the invention of this application does not require these components. Thus, the number of components in a vacuum is significantly reduced.

High throughput at high resolution is achieved by applying the aforementioned electronic optical device including primary optical system of the invention of this application as described above to the semiconductor inspection apparatus. Accordingly, configuration is preferably applicable to EUV mask inspection and NIL mask inspection. Also in the case of low LE (landing energy), high resolution can be achieved.

Embodiment 2

Second Embodiment of Primary Optical System

Figure 14:
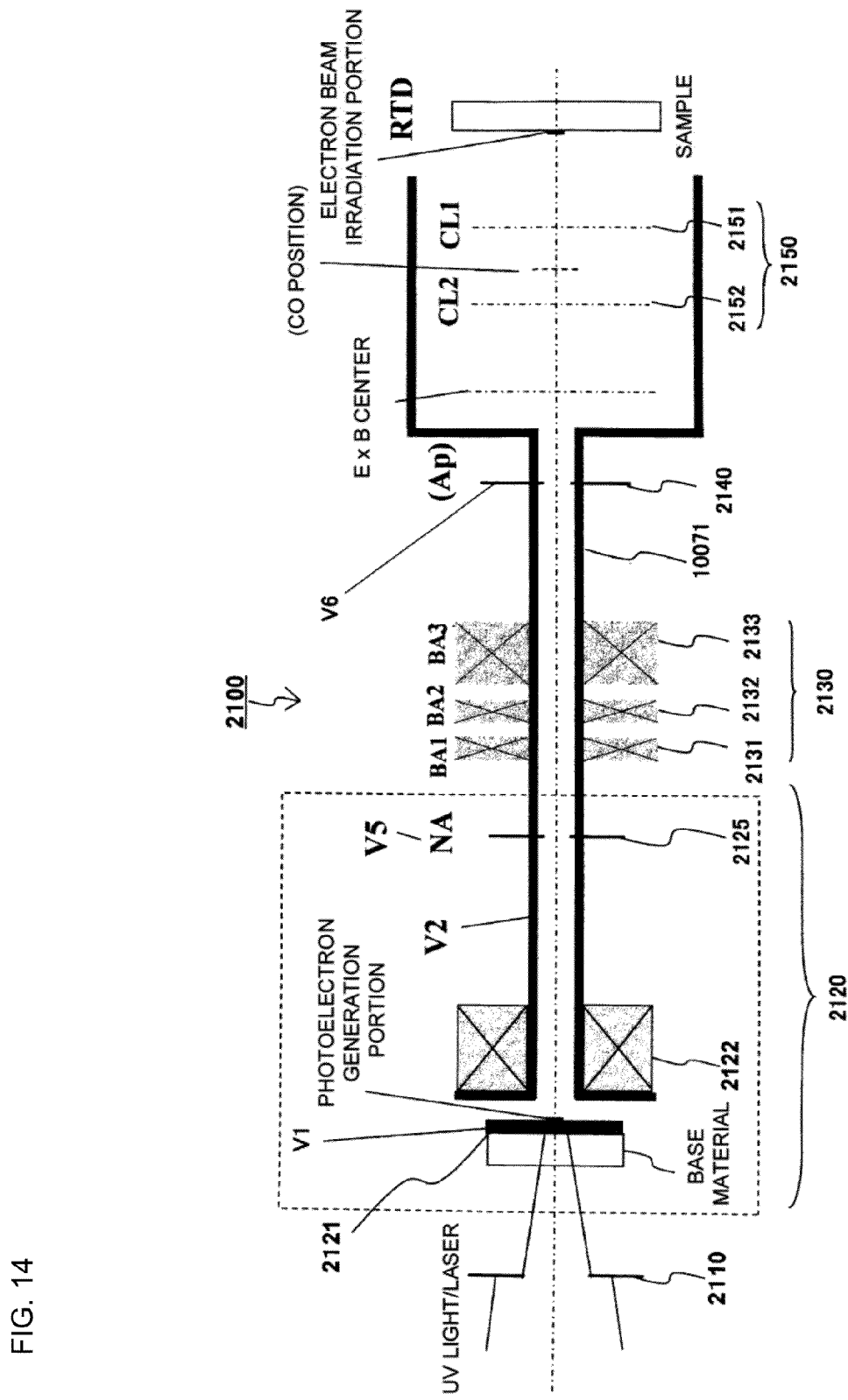
FIG. 14 is a diagram showing a second embodiment of the primary optical system according to an embodiment of the present invention.

A second embodiment of the primary optical system according to the invention of this application will be described. FIG. 14 is a diagram showing the second embodiment of the primary optical system according to the invention of this application. In a schematic view, this primary optical system 2100 includes: a light source (not shown), a field aperture (FA) 2110, a photoelectron generator 2120, an aligner 2130, an E×B deflector (Wien filter) (not shown), an aperture 2140, a cathode lens (CL) 2150, a first pipe 10071; and a second pipe (not shown) that stores the primary optical system. The second embodiment of the primary optical system according to the invention of this application is characterized in that the reference potential is a high voltage. Description will hereinafter be made mainly on differences from the aforementioned primary optical system according to the invention of this application.

This embodiment has a double structure that includes the first pipe 10071 and the second pipe. The photoelectron generator 2120 includes a photoelectronic surface 2121, an extraction lens 2122, and a numerical aperture 2125.

The first pipe 10071 is for generating a reference voltage in the case where the reference voltage is at a high voltage. The high voltage is applied to the first pipe. The first pipe 10071 is disposed in the holes which are provided at the extraction lens 2122, the numerical aperture 2125 and the aligner 2130 and through which the primary beam passes, so as to be inscribed in the holes. The diameter is formed to be large on the latter stage of the aperture 2140. The cathode lens 2150 is arranged in the portion where the diameter is formed to be large.

The first pipe 10071 may be made of any of materials other than magnetic materials; there is no other limitation. A thin copper pipe, a thin titanium pipe, or copper-plated or titanium-plated plastic is preferably adopted. Accordingly, when a high voltage is applied to the first pipe 10071, a magnetic field is formed in the first pipe 10071. The field highly accelerates the primary electron beam occurring on the photoelectronic surface 2121 irradiated with light or laser light.

Although not shown in FIG. 14, the second pipe covers the field aperture (FA) 2110, the photoelectron generator 2120, the aligner 2130, the E×B deflector (Wien filter) (not shown), the aperture 2140, the cathode lens (CL) 2150 and the first pipe 10071, and is set to GND. The second pipe is the outermost configurational component. Accordingly, this pipe is set to GND for conductive connection with the other parts of the apparatus and for preventing an electric shock in case where a person touches the apparatus.

The extraction lens is one lens. The second embodiment of the primary optical system according to the invention of this application adopts an electromagnetic lens. The other configurational components are analogous to the components of the aforementioned embodiment. Accordingly, the description is omitted.

The primary optical system 2100 according to the invention of this application can set the sample surface voltage to GND by adopting such a double structure pipe. The electron beam occurring on the photoelectronic surface 2121 can be highly accelerated by applying the high voltage to the first pipe 10071, which is the inner pipe of the double pipe structure. Accordingly, the primary optical system according to the invention of this application can be regarded as a high acceleration column.

In the primary optical system 2100 according to the invention of this application (see FIG. 14), the voltages applied to the respective configurational components are as follows. The voltage of the photoelectronic surface 2121 is V1. The voltage of the first pipe 10071 is V2. The voltage of the numerical aperture NA 2025 is V5. The voltage of the aperture 2140 is V6. The wafer surface voltage (also referred to as retarding voltage) is RTD. In a low LE condition, V1=RTD−10 V to RTD+5 V. V2, V5 and V6 are reference potentials. In one embodiment of the invention of this application, setting is made such that RTD=0, V1=−5 V, and the reference potential=40000V. Such voltage application can achieve high throughput at a low LE and high resolution.

If a magnetic field lens is adopted here, an occurring longitudinal magnetic field (residual magnetic field in the optical axis) turns the beam. Accordingly, the two-dimensional photoelectron generation shape formed on the photoelectronic surface may turn after passing through the generation part and the magnetic field lens in some cases. In order to correct the turning, a turning correction lens is arranged around NA or at a position downstream of the magnetic field lens to correct adverse effects. The correction lens at the position downstream of the magnetic field lens is preferably set at a position as close as possible to (immediately after) the magnetic field lens to correct the turning.

In the electrostatic lens primary optical system 2000 (see FIG. 12) of the invention of this application, an example of the double pipe structure will be described with reference to the photoelectronic surface 2021 voltage V1. Voltages are applied to the respective configurational components as follows. That is, in the case of a low LE, V1=RTD−10 V to RTD+5 V. V2, V5 and V6 are reference potentials. V3=reference voltage+10 to 100 kV. In an embodiment of the invention of this application, setting is made such that RTD=0, V1=−5 V, V2=reference potential+40000 V, and V3=65000 V. The pipe 1 storing these lenses is provided such that the reference voltage is the reference spatial voltage. The lens, the aperture and the aligner in FIG. 12 are stored in the pipe 1 to which the reference voltage is applied. The pipe 2 set to GND potential is arranged outside the pipe 1. The pipe 1 and the pipe 2 are fixed to each other by insulative components (the pipe 1 and the pipe 2 are not shown). Such voltage application can achieve high throughput at a low LE and high resolution.

The primary optical system 2100 according to the invention of this application can exert an advantageous effect that allows inspection while leaving the sample surface voltage RTD to 0 V. Furthermore, the primary optical system 2100 according to the invention of this application can exert effects analogous to the effects of the primary optical system 2000 according to the invention of this application. The electronic optical device including the primary optical system according to the invention of this application has analogous advantageous effects. Accordingly, the description is omitted.

Variation of Photoelectron Generator in Primary Optical System

Figure 15:
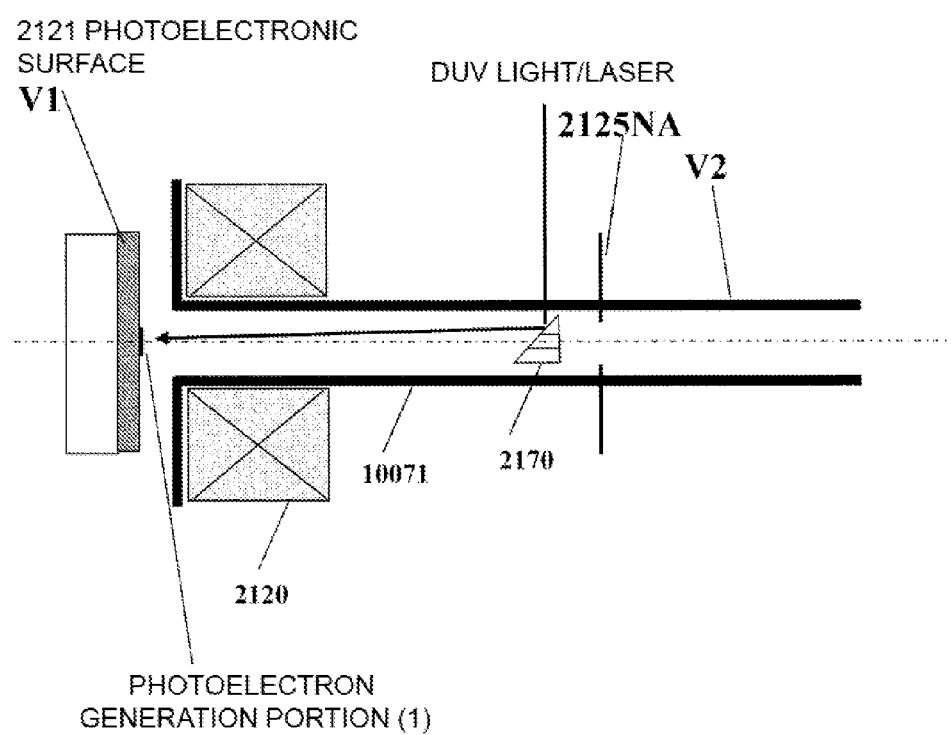
FIG. 15 is a diagram showing an example where light or laser guided to a photoelectronic surface from a position in a primary system by a mirror provided in a column, according to an embodiment of the present invention.
Figure 16:
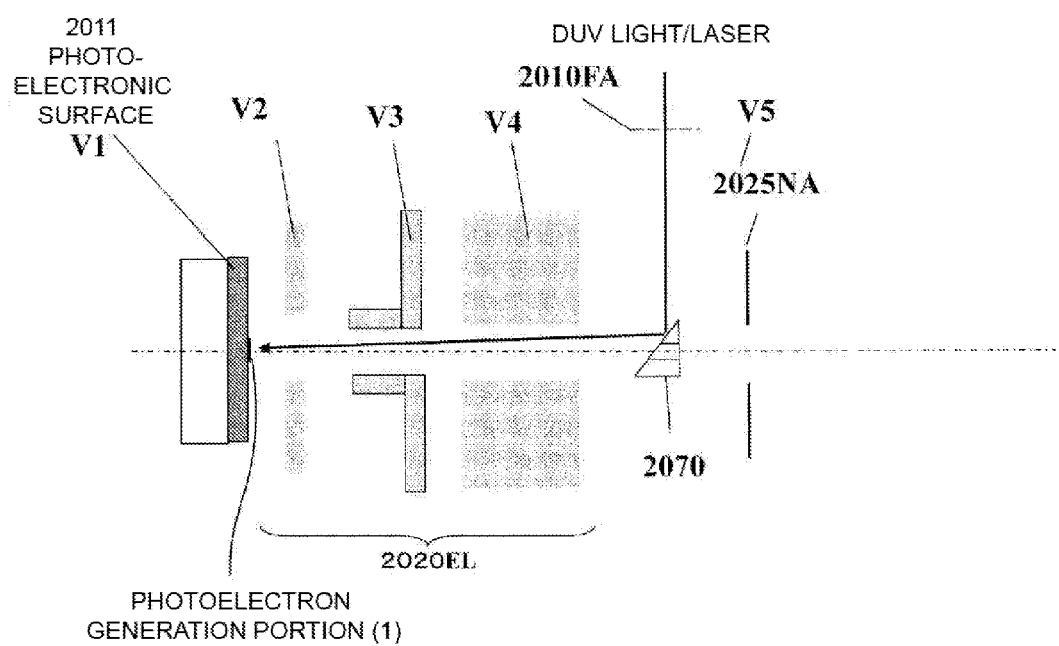
FIG. 16 is a diagram showing an example where light or laser guided to a photoelectronic surface from a position in a primary system by a mirror provided in a column.

Another example of the primary optical system according to the invention of this application will be described. FIGS. 15 and 16 show examples where light or laser is guided by a mirror arranged in the column from a midpoint in the primary system to the photoelectronic surface.

FIG. 15 is an example where the reference voltage is a high voltage, e.g., 40 kV. That is, the example is an application to the second embodiment of the primary optical system 2000 according to the invention of this application. Here, in order to form the reference voltage, a voltage of V2=40 kV is applied to the pipe 10071 to which the high voltage is to be applied. The inside of the pipe 10071 is an identical voltage space. Accordingly, in this example, a mirror having a hole at the center allowing photoelectrons to pass therethrough, for instance, a triangular mirror 2170 are adopted. DUV light or UV laser is guided through the hole, not shown, provided at the pipe 100071, and reflected by the triangular mirror 2170 to be incident on the photoelectronic surface 2121. Photoelectrons occur from the irradiated surface. The photoelectrons passes through the EX lens 2120 and NA 2125 and then passes through the downstream aligner and emitted onto the surface of the sample. Here, occurring photoelectrons form the trajectory of the primary system. Accordingly, a voltage of a prescribed value is applied to the photoelectronic surface 2121. It is determined such that LE=RTD voltage−V1.

FIG. 16 shows an example where the photoelectronic surface is irradiated with light or laser for generating photoelectrons by the triangular mirror 2070, as with the example shown in FIG. 15, but the reference voltage is GND. That is, this example is an application to one embodiment the primary optical system 2000 according to the invention of this application. Here, for instance, V2, V4 and V5 are GND, and a reference voltage space are defined therearound. The mirror similar to the mirror in FIG. 15 is arranged to allow light or laser to be introduced. Here, the amount of occurring photoelectrons is defined by laser irradiation intensity. The irradiation intensity is thus controlled. For the control, the aforementioned method of controlling the intensity is used. Here, the surface of the mirror and the entire mirror structure are coated with conductive material. The potential of the mirror is identical to the reference potential. The identical potential is selected so as not to disturb the space potential. A hole is formed at the optical axis center part of the mirror to allow the primary beam to pass therethrough without being affected by the mirror. The primary beam passes through this hole. The inner surface of the hole is also coated with the conductive material or a conductor and connected to the reference voltage part so as to be isopotential with respect to the reference voltage.

Two methods will be described on photoelectron generating shapes. Description will be made with reference to FIG. 16. One method uses an FA aperture 2010 that defines the beam shape before the beam is incident on the mirror in the column. A beam having the shape of the field aperture (FA) 2010 is formed. The photoelectric surface is irradiated with the beam to cause photoelectrons having this shape. Here, the projection size of the field aperture (FA) 2010 is controlled by the position of the lens at the upstream of the field aperture (FA) 2010.

Figure 17:
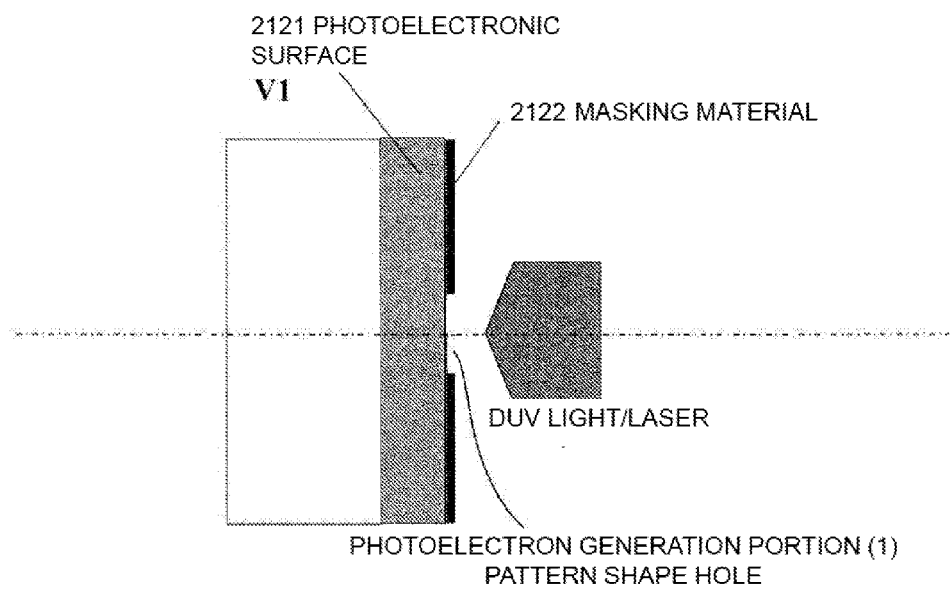
FIG. 17 is a diagram showing an example of adopting an exemplary photoelectric surface coated with a masking material of a pattern in a second embodiment of an primary optical system, according to an embodiment of the present invention.

The other method coats a masking material of a pattern on the photoelectronic surface. FIG. 17 is a diagram showing an example where an example of the photoelectronic surface coated with the masking material of the pattern is used in the second embodiment of the primary optical system according to the primary optical system 2100 according to the invention of this application. As shown in FIG. 17, a masking material 2122 is coated on the photoelectronic surface 2121. The masking material 2122 has a hole that has a pattern shape. No masking material is coated on the hole portion. No photoelectron occurs from the coated portions. Photoelectrons occur from portions without the masking material. That is, during irradiation with DUV light, photoelectrons having the pattern shape occur from the photoelectric surface portion having the pattern without masking. Here, masking material for coating may be any material that does not cause photoelectrons. This material may be a material having a high work function or a material with a low occurring efficiency. For instance, the material may be carbon, Pt, Cr or the like. Note that, since charging up forms potential nonuniformity to cause adverse effects, such as curving of the trajectory of the released electrons, a conductive material is adopted.

Figure 18:
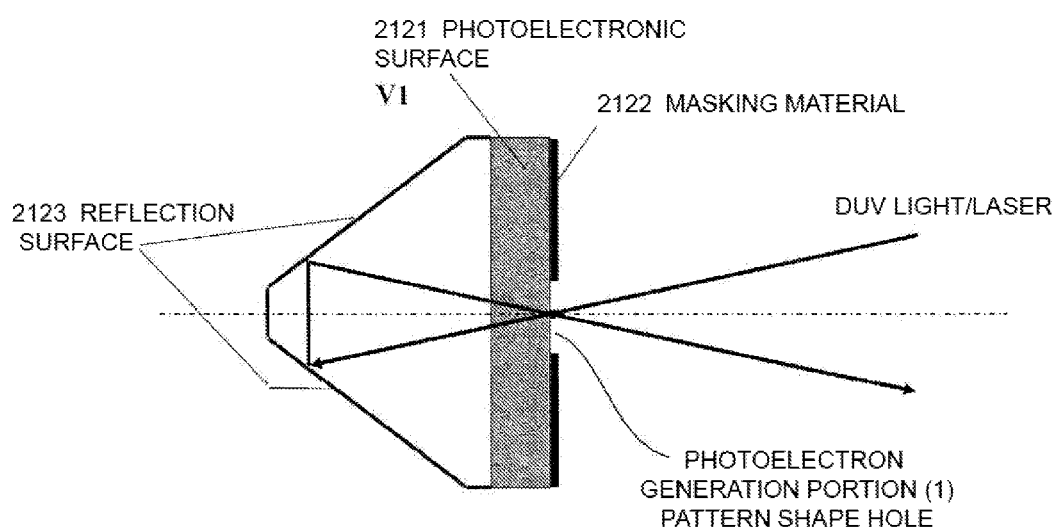
FIG. 18 is a diagram showing a method of irradiating the photoelectronic surface again by reflecting light or laser having passed, according to an embodiment of the present invention.

FIG. 18 is a diagram showing a method of reflecting the passing light or laser to irradiate the photoelectronic surface again, in order to further improve the efficiency. Light or laser incident on the photoelectronic surface 2121 is reflected in an element that allows light or laser to pass and has a reflection surface structure (reflection surface 2123), and returns to the photoelectronic surface 2121, which is thus irradiated again. This method irradiates the photoelectronic surface 2121 with light or laser multiple times, which thereby improves the efficiency. For instance, provided that the light/laser transmittance of the photoelectronic surface 2121 is 60%, repetitive irradiation with 60% of the passing light or laser can improve the amount of occurring photoelectrons according to the number of irradiation times. The method is not limited to this example; any method of multiple irradiation is effective. In particular, irradiation two to five times can enjoy the effectiveness. Since further irradiation times reduce the intensity of light or laser, the effectiveness is significantly reduced. If the multiple times of irradiation are allowed as described above, an advantageous effect can be exerted where the intensity of incident light or laser remains ½ to ⅕ of the case of one time irradiation. For instance, in the case where an intensity of irradiation light or laser of 1 W is required, 0.2 to 0.5 W is sufficient. In particular, there are a case where a large output light source is required, a case without the light source itself, and a case where the operation management cost is high. If a low output light source can be used here, the use is significantly effective because the use reduces the adverse effects of cost, efficiency and heat, adverse effects of deterioration of elements of optical introduction system and the like.

The examples described with reference to FIGS. 17 and 18 are examples of application to the primary optical system 2100 that pertains to the second embodiment of the primary optical system 2100 according to the invention of this application. However, application is not limited thereto. The examples may be applied to the primary optical systems 2000 according to the other embodiments.

Embodiment 3

Semiconductor Inspection Apparatus Including Double Pipe Structure Lens Tube

As described above, the electronic optical device 70 including the primary optical system 2100, which is described as the second embodiment of the primary optical system according to the invention of this application, is different in setting of voltages applied to the respective configurational components from a typical electron gun. That is, reference potential V2 is used as the high voltage (e.g., +40000 V). First, the semiconductor inspection apparatus 1 including the electronic optical device 70 according to the invention of this application has a double pipe structure.

Figure 19:
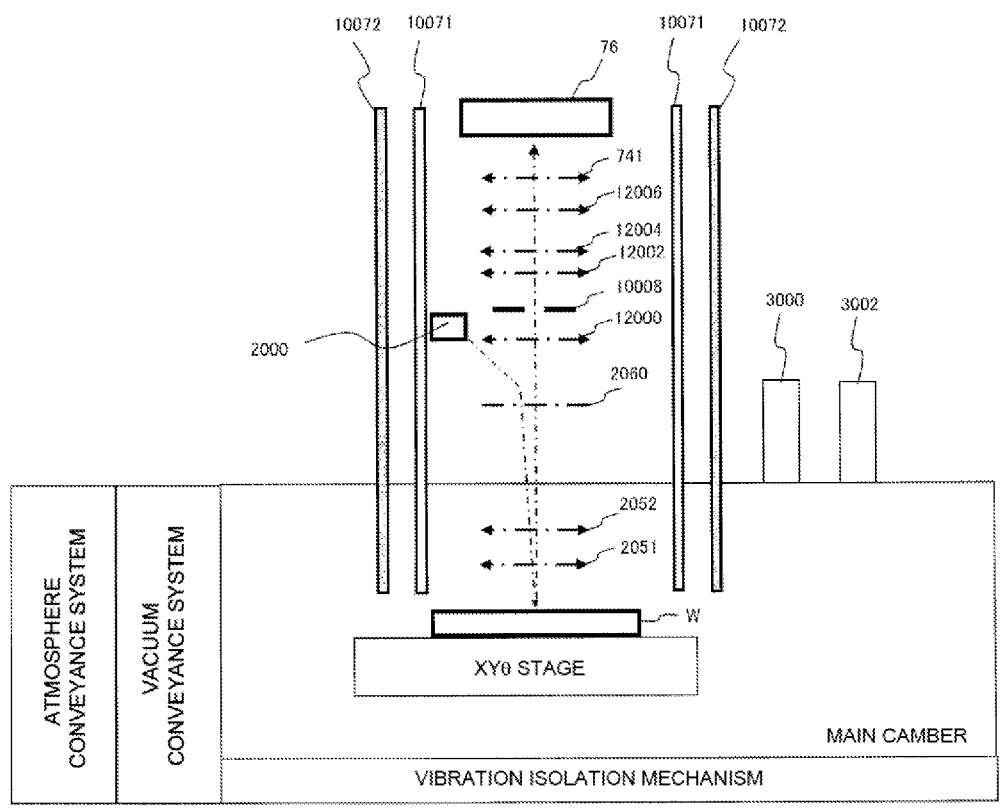
FIG. 19 is a diagram schematically showing a double pipe structure of a semiconductor inspection apparatus according to an embodiment of the present invention.

Description will be made with reference to FIG. 19. FIG. 19 is a diagram schematically showing the double pipe structure of the semiconductor inspection apparatus according to one embodiment of the present invention. In FIG. 19, the first pipe and the second pipe are emphasized. The sections of the actual first pipe and second pipe are different from the illustration. As shown in FIG. 19, the electronic optical device 70 including the primary optical system 2000 according to the invention of this application includes two pipes, which are the first pipe 10071, and a second pipe 10072 provided outside of the first pipe 10071. In other words, the device has a double pipe structure. The double pipe structure internally stores a light source, a primary optical system, a secondary optical system and a detector. A high voltage (e.g., +40000 V) is applied to the first pipe 10071. The second pipe 10072 is set to GND. The first pipe 10071 secures a spatial reference potential V0 with reference to the high voltage. The first pipe is surrounded by the second pipe and is thus set to GND. This configuration achieves GND connection in the apparatus installation and prevents electric shock. The pipe 10071 is fixed to the pipe 10072 by insulative components. The pipe 10072 is set to GND, and attached to the main housing 30. The primary optical system 2000, the secondary optical system, the detection system 76 and the like are arranged in the first pipe 10071.

An internal partition wall between the first pipe 10071 and the second pipe 10072, even including components screws and the like, are made of nonmagnetic material not to affect the magnetic field, thereby preventing the magnetic field from affecting the electron beam. Although not shown in FIG. 19, a space is provided at the side of the second pipe 10072. In the space, a protrusion is connected in which parts of the primary optical system 2000, such as the light source and the photoelectron generator, are arranged. A space similar to the space provided for the second pipe 10072 is also provided for the first pipe 10071. Photoelectrons occurring from the photoelectron generation portion pass through the spaces, and the sample is irradiated with the photoelectrons. The light source is not necessarily provided in the second pipe 10072. Instead, the light source may be provided on the atmosphere side, and light may be introduced into the photoelectron generation portion stored in the second pipe 10072 on the vacuum side. However, the primary optical system and the secondary optical system are necessarily stored in the double pipe structure. The detector may be disposed in the first pipe 10071, or at the position with a potential independent from the first and second pipes. Here, the potential of the detection surface of the detector is set to any value to control the energy of electrons incident on the detector to have an appropriate value. In a state of potential separation by the insulative component from the pipe 1 and the pipe 2, any voltage is applied to the detector to achieve a detection sensor surface potential, thereby allowing operation. Here, provided that the sensor surface potential is VD, the energy incident on the sensor surface is defined by VD−RTD. In the case where EB-CCD or EB-TDI is adopted as the detector, it is effective to set the incident energy to 1 to 7 keV for the sake of reducing damage to the sensor and use for a long period of time.

Figure 20:
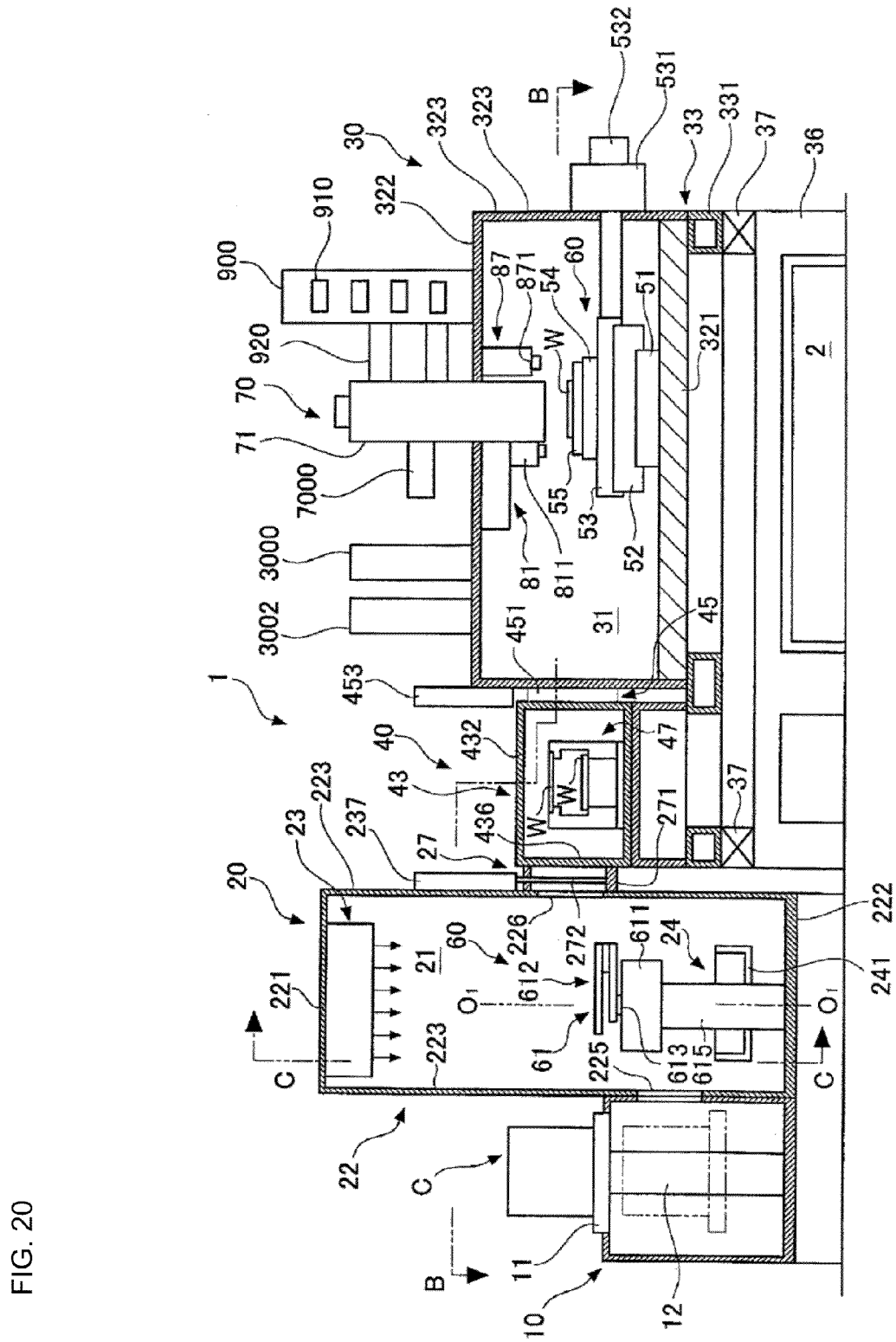
FIG. 20 is a diagram showing the entire configuration of a semiconductor inspection apparatus according to an embodiment of the present invention.

Furthermore, another configuration of the semiconductor inspection apparatus 1 including the electronic optical device 70 according to the invention of this application will be described. FIG. 20 is a diagram showing the entire configuration of the semiconductor inspection apparatus 1 according to one embodiment of the invention of this application. As shown in FIG. 20, the semiconductor inspection apparatus 1 according to the one embodiment of the invention of this application includes a second vacuum chamber 900. That is, the second vacuum chamber 900 is arranged in the semiconductor inspection apparatus 1. The power supply 910 causing a high voltage is arranged in the second vacuum chamber 900. The lens tube 71, which stores the first pipe and the second pipe, and the second vacuum chamber 900 are caused to communicate with each other by the communication pipe 920. wiring is arranged in the communication pipe 920. This arrangement is adopted because the electronic optical device 70 according to the invention of this application has a reference potential V0 at a high voltage as described above, which is different from the conventional configuration. In order to set the reference potential V0 to the high voltage, the semiconductor inspection apparatus 1 including the electronic optical device 70 according to the invention of this application includes pipes having a double pipe structure. The high voltage is applied to the internal first pipe 10071. Application of such a high voltage requires a large feedthrough between the atmosphere and the vacuum in order to secure a creeping dielectric strength voltage because the dielectric strength voltage on the atmosphere side is low. For instance, provided that the dielectric strength voltage is 1 kV/mm, an insulative component having at least an insulation creeping distance of 40 mm at 40 kV and large connectors supporting the specification are required. If a number of such connectors are adopted, a space used for an installation section for the connectors in the lens tube accounts for a large ratio, and the size of the lens tube and the cost are increased. Thus, in the present invention, a vacuum chamber dedicated to the power supply is provided. This configuration negates the need of the feedthrough from the output. Accordingly, it is sufficient that the wiring is connected to the electrode. Here, generated gas from the power supply is a factor of contamination. Accordingly, it is effective to establish vacuum insulation between the vacuum chamber for the power supply and the lens tube using an insulative component, in order to block vacuum communication at the middle of the wiring. In the case of high voltage, the wires should be thick. In the semiconductor inspection apparatus 1, the higher the voltage applied to the sample, the more a number of thick wires are required to be arranged around the stage. In the case of arranging the wires having a large diameter in the working chamber, a large torque is required because stage movement is accompanied by movement of the wires. There is a problem in that, for instance, the frictional force between the wires and the surface of walls is large, and particles are formed. Accordingly, the configuration where the sample potential is set to GND, and the reference voltage is set to the high voltage is significantly effective. Here, it is further effective that the voltage of the surface of the detector is controlled to reduce damage to the sensor. The sample potential, the reference stage potential and the sensor surface potential are set to different values. Here, for instance, it is significantly effective to set the sample potential to GND, set the reference voltage to 10 to 50 kV, and sets the sensor surface potential to 3 to 7 kV. As described above, the second vacuum chamber 900 is arranged to store the power supply 910 and communicates with the lens tube and the like through the communication pipe 920, and the wiring is arranged in the communication pipe 920, thus achieving vacuum wiring. An external power supply (AC 100 V, DC 24 V or the like) is introduced to the power supply, and an optical communication system is adopted. A small feedthrough is sufficient for an extent to such an external power supply. Accordingly, connection from the atmosphere side is easy.

As described above, the configuration has the double pipe structure. Accordingly, a state can be achieved where the inner pipe (pipe 1) is in a high vacuum, and a space between the external pipe (pipe 2) and the inner pipe (pipe 1) is at an atmospheric pressure. In such a case, arrangement of the electrostatic electrode in the pipe 1 is sometimes unrealistic because the number of connections on the wall of the wiring pipe 1 is large, and the feedthrough between the vacuum and atmosphere is large. Here, the lens, the aligner and the corrector using the magnetic field are adopted. This configuration negates the need of arranging the feedthrough in the pipe 1, and is effective for the case of forming a reference space at the high voltage. This structure is applicable to the modes of Embodiments 1 to 9.

The double structure is applied to each of the lens tube, the second vacuum chamber for power supply, and the communication pipe which is for vacuum wiring and through which the lens tube and the second vacuum chamber communicate with each other, thereby providing the aforementioned semiconductor inspection apparatus 1 including the primary optical system 2000 according to the invention of this application. However, this is only an example. The semiconductor inspection apparatus 1 including the primary optical system 2000 according to the invention of this application is not limited thereto. The aforementioned embodiments, for instance, the embodiments of the primary system and the secondary system as described in Embodiments 1 to 9 can be embodied adopting the double pipe structure of this embodiment.

Embodiment 4

Beam Measurement Method at Crossover Position, Method of Adjusting Primary Irradiation Electron Beam and NA Position Using the Measuring Method, and Semiconductor Inspection Apparatus Using the Adjustment Method A semiconductor inspection method will be described that includes an electronic optical device provided with the primary optical system according to the invention of this application. The following method is also applicable to a semiconductor inspection apparatus that includes electronic optical device including a typical electron gun.

In this embodiment, a mapping projection observation apparatus (electron beam observation apparatus including a mapping projection optical system) is used to observe a sample. Such an electron beam observation apparatus includes a primary optical system and a secondary optical system. The primary optical system 2000 irradiates the sample with electron beam emitted from a photoelectron generation portion to generate electrons including information on the structure and the like of the sample. The secondary optical system includes a detector, and forms an image of electrons generated by irradiation with the electron beam. The mapping projection observation apparatus uses an electron beam with a large diameter to acquire an image in a wide range. That is, irradiation is performed using a planar beam instead of a spot beam narrowed as in the case of a typical SEM.

When the sample is irradiated with the electron beam, multiple type of electrons are detected by the secondary optical system. The multiple types of electrons are mirror electrons, secondary electrons, reflected electrons, and backscattering electrons. In this embodiment, the secondary electrons, reflected electrons and the backscattering electrons are referred to as secondarily released electrons. The sample is then observed using the characteristics of the mirror electrons and the secondarily released electrons. The mirror electrons recoil immediately before the sample without colliding with the sample. A mirror electron phenomenon is caused by an action of an electric field of the surface of the sample.

As described above, the secondary electrons, the reflected electrons and the backscattering electrons are referred to as the secondarily released electrons. Also in the case where the three types of electrons are mixed, the term of secondarily released electrons is used. Among the secondarily released electrons, the secondary electrons are typical. Thus, the secondary electrons are sometimes described as a representative type of the secondarily released electrons. On both the mirror electrons and the secondarily released electrons, expressions, such as "released from the sample", "reflected by the sample" and "generated by irradiation with the electron beam" may be used.

Figure 21:
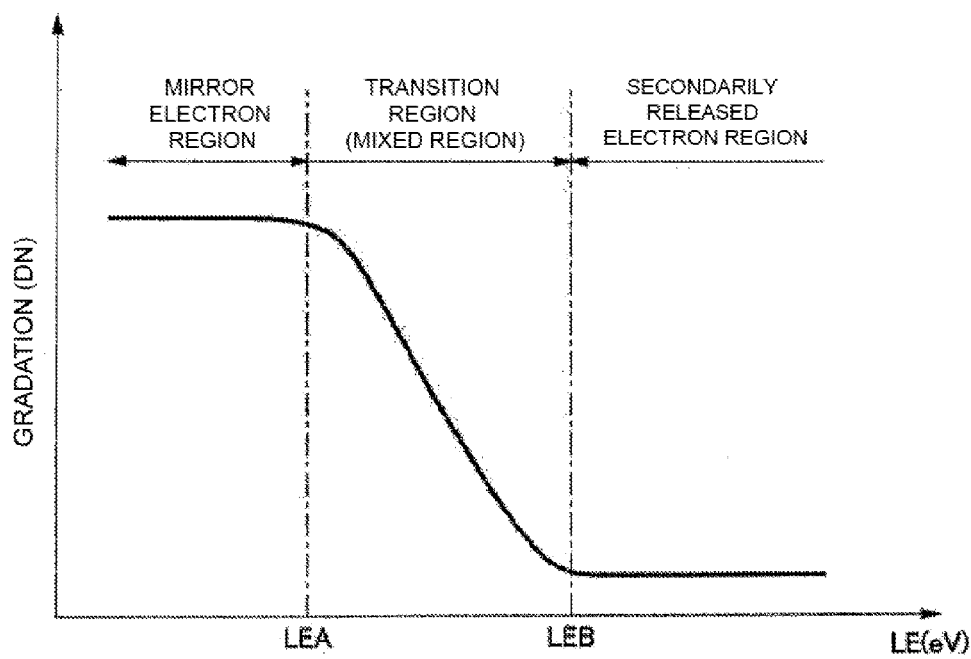
FIG. 21 is a diagram showing a relationship between landing energy LE and gradation DN when a sample is irradiated with an electron beam, according to an embodiment of the present invention.

FIG. 21 is a diagram showing the relationship between the landing energy LE and the gradation DN in the case of irradiating the sample with electron beams. The landing energy LE is an energy applied to the electron beam with which the sample is irradiated. It is provided that the acceleration voltage Vacc is applied to the electron gun, and a retarding voltage Vrtd is applied to the sample. In this case, the landing energy LE is represented by the difference between the acceleration voltage and the retarding voltage.

In FIG. 21, the gradation DN in the ordinate represents the luminance of an image generated from electrons detected by the detector of the secondary optical system. That is, the gradation DN represents the number of detected electrons. The gradation DN increases with the number of detected electrons.

FIG. 21 shows gradation characteristics in a small energy region around 0 [eV]. As shown in the diagram, in a region where the LE is higher than the LEB (LEB<LE), the gradation DN is a constant value that is relatively small. In a region where the LE is equal to or less than the LEB but at least the LEA (LEA LE 5 LEB), the gradation the DN increases with decrease in the LE. In a region where the LE is smaller than the LEA (LE<LEA), the gradation DN is a constant value that is relatively large.

The gradation characteristics relate to the types of detected electrons. In the region where LEB<LE, almost all the detected electrons are the secondarily released electrons. The region can be regarded as a secondarily released electron region. Meanwhile, in the region where LE<LEA, almost all the detected electrons are the mirror electrons. This region can be regarded as a mirror electron region. As shown in the diagram, the gradation of the mirror electron region is larger than the gradation of the secondarily released electron region. This feature is because the mirror electron distribution range is smaller than the range of the secondarily released electrons. Since the distribution range is small, electrons as many as possible reach the detector, and the gradation increases.

The region where LEA≤LE≤LEB is a transition region from the secondarily released electron region to the mirror electron region (or reversed relationship). The region may be a region where the mirror electron and the secondarily released electrons are mixed, and may be regarded as a mixed region. In the transition region (mixed region), as the LE decreases, the amount of generated mirror electron increases and the gradation increases.

LEA and LEB denote the minimum landing energy and maximum landing energy of the transition region, respectively. Specific values of the LEA and LEB are described. Research results of the inventors show that LEA is at least −5 [eV] and LEB is 5 [eV] or less (i.e., −5 [eVi]≤LEA≤LEB≤5 [eV]).

Advantages of the transition region are as follows. In the mirror electron region (LE<LEA), all electrons generated by beam irradiation are mirror electron. Accordingly, all detected electrons are mirror electrons irrespective of the shape of the sample, the difference in gradation at both the pits and bumps of the sample is small, and the S/N ratio and contrast of patterns and defects are small. Accordingly, it is sometimes difficult to use the mirror electron region for inspection. In contrast, in the transition region, mirror electrons are characteristically and specifically generated at edges of the shape, and secondarily released electrons are generated at the other portions. The S/N ratio and contrast of the edges can thus be increased. The transition region is therefore significantly effective for inspection. This point will be described in detail below.

Figure 22:
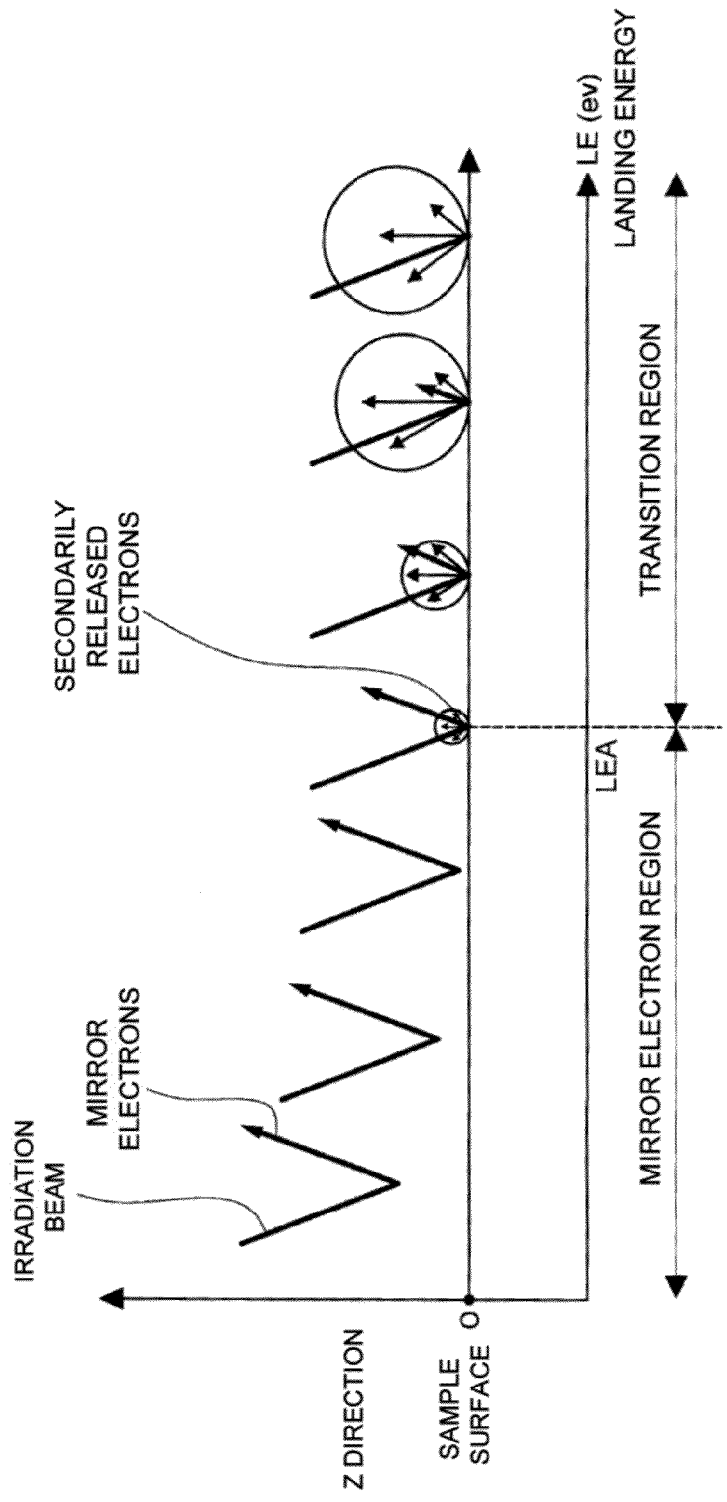
FIG. 22 is a diagram showing a phenomenon in transition region, according to an embodiment of the present invention.

FIG. 22 shows the phenomenon in the transition region. FIG. 22 is a diagram showing the phenomenon in the transition region. In FIG. 22, in the mirror electron region (LE<LEA), all electrons become mirror electrons without colliding with the sample. In contrast, in the transition region, a part of electrons collides with the sample, and the sample emits secondarily released electrons. The higher the LE is, the higher the ratio of the secondarily released electrons is. Although not shown, if the LE exceeds the LEB, only secondarily released electrons are detected.

In the present invention, a method of condition creation and adjustment of the electron beam of the irradiation electron beam and the secondary optical system for forming an image, including the secondarily released electron region, the transition region, the mirror electron region, and including patterns with asperity structures, and patterns without asperities. The present invention can greatly effectively achieve highly accurate adjustment and condition creation. This point will be described below.

The present invention is significantly characterized by measuring the position and shape of the beam reaching a crossover position (hereinafter, referred to as a CO position) at a midpoint in the secondary optical system. Conventionally, the NA is moved without measurement of the beam reaching the CO position, and the contrast of the image is evaluated. This technique takes too much time. The conventional procedures are as follows.

a. Form image forming conditions by a lens between the CO position and the detector.

b. Use a large diameter in the case of presence of an NA. Instead, remove the NA. It is preferred that the entire CO can be observed. For instance, φ1000 to φ5000 μm.

c. Take an image of the beam at the CO position.

Figure 23:
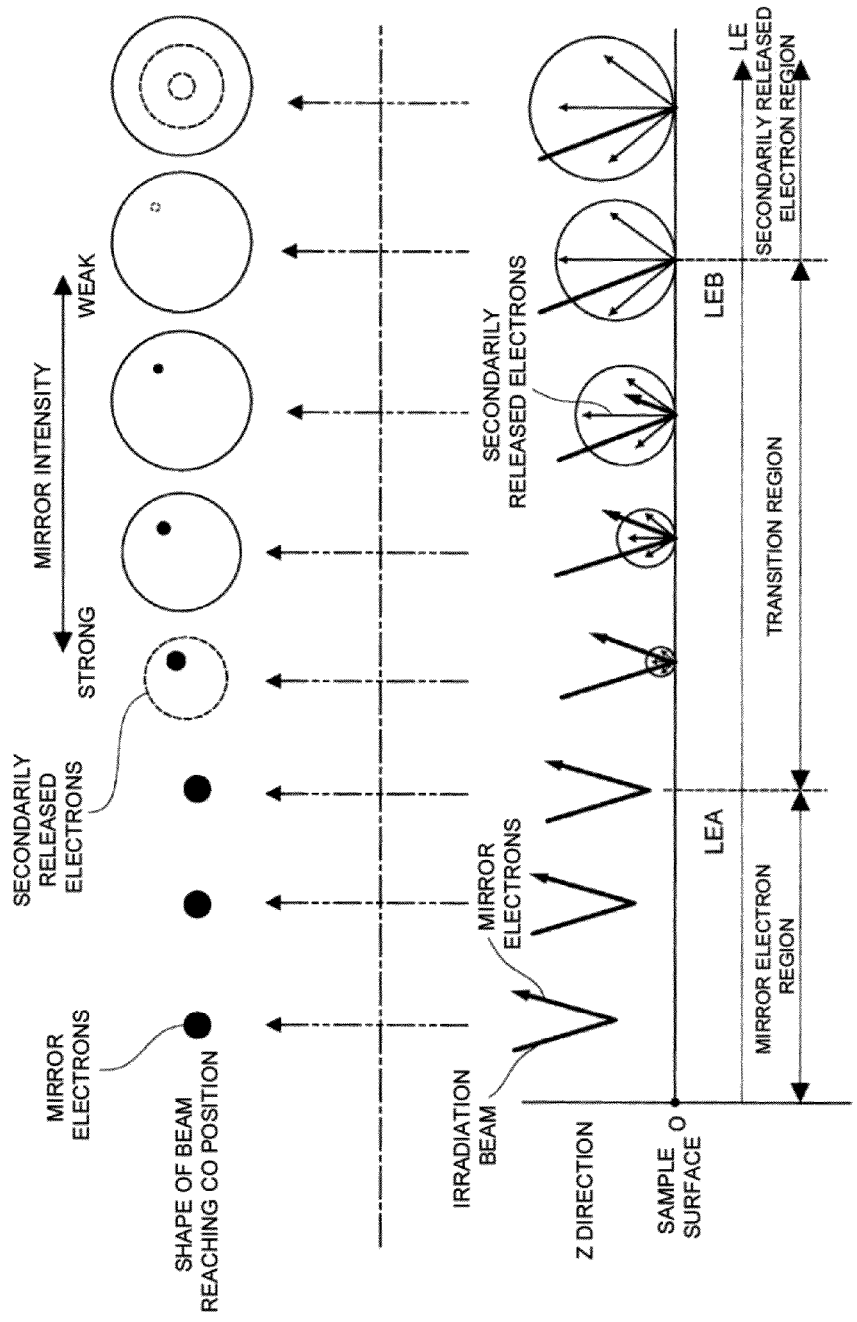
FIG. 23 is a diagram showing an inspection example of a beam shape at a CO position with respect to LE, according to an embodiment of the present invention.

In the present invention, in order to efficiently take an image and perform adjustment as described above, and to prevent deterioration due to contamination, improve exchangeability and facilitate maintenance, a movable numerical aperture (NA) 10008 is characteristically provided; the configuration of the apparatus will be described. FIG. 23 shows an inspection example of a beam shape at the CO position at the LE. FIG. 23 is a diagram showing the inspection example of the beam shape at the CO position at the LE. FIG. 23 shows: the shape of the beam reaching the CO position in the upper half of the diagram; and phenomena in the mirror region of the beam with which the surface of the sample is irradiated, the transition region and the secondarily released electron region in the lower half. In the upper half, the mirror electrons are indicated by solid dots, and the secondarily released electrons are indicated by an open circle. At the LE, in the mirror electron region, only the mirror electrons are observed. In the transition region, the mirror electron and the secondarily released electrons are observed. In the secondarily released electron region, only the secondarily released electrons are observed, but no mirror electron is observed. Through use of image data acquired by the imaging, the position, size and intensity of the mirror electrons, and the size and intensity of the secondarily released electrons are observed.

When the sample as a target is irradiated with the irradiation electron beam, it can be immediately determined which one is the state concerned among the three states on the basis of the observation. Conventionally, ambiguous prediction has been made on the basis of irradiation conditions and an acquired image. Accordingly, accurate determination on situations as described above cannot be made. Furthermore, errors due to power supply setting accuracy and adverse effects due to optical axis conditions cannot be correctly determined either. These problems occur because formation of the mirror electron region and the transition region is sensitive to the LE and the optical axis conditions and adverse effects are also caused owing to errors of control devices and the conditions. For instance, the setting accuracy of the power supply is typically about 0.1%. The setting error of the 5000 V-setting power supply reaches 5 V. A variation of 5 V is sufficient for a change from the transition region to the mirror region, and a change from the transition region to the secondarily released electron region. Since the verification cannot have been made, only ambiguous predictions have been allowed; e.g., the predictions include that the region might be the mirror electron region and that the region might be the transition region, based on the setting values.

Furthermore, according to the present invention, a method will be described that sets the NA position where the primary irradiation electron beam is adjusted and an image is formed, using the measurement method. It is provided that the direction of the sample, such as a mask and a wafer, has already been positionally adjusted with respect to the coordinates of the secondary optical system (column).

Photoelectron Cathode Primary System

FIG. 14 shows an example where the reference voltage is not GND but is a high voltage. In this example, the reference voltage is +40000 V. A cylindrical pipe is adopted in order to integrate the reference voltage and form an electric field in the column. The pipe is represented as a pipe 1. A voltage of 40000 V is applied to form the reference voltage. A part adjacent to the photoelectronic surface is parallel to the equipotential line (distribution) photoelectric surface. A magnetic field lens is adopted as the lens. An electromagnetic aligner is adopted as the aligner. The NA and the other apertures are set to the reference potential, and provided in the pipe structure.

A high voltage is applied to the pipe 1. Accordingly, another pipe 2 is provided outside of the pipe 1. The pipe 2 is set to GND. This setting allows the apparatus to establish GND connection. The pipe 1 and the pipe 2 are insulated from each other by a voltage-resistant insulator. Necessary application voltage is maintained. Although not described here, the reference voltage of the primary system is controlled in order to set the reference voltage of the secondary optical system to the high voltage. Accordingly, as with the primary optical system, the secondary optical system adopts a column with a double structure of pipes. The high voltage is applied to the inner pipe, and the outer pipe is set to GND. The voltage difference is kept as with the primary system. The pipe 1 may be conductive and coated with resin material, such as polyimide and epoxy, on the outer periphery of the pipe 1. The outer periphery of the resin material may be further coated with conductive material, and the conductive material may be GND. Accordingly, the inside of the resin material is set to the reference voltage, which is the high voltage, the outside is set to GND, and components with another GND connection and GND installation can be achieved. Furthermore, a pipe 2 that is a shield pipe may be externally provided. The pipe 2 is made of magnetic material, such as permalloy or pure iron, and can shield an external magnetic field. This embodiment is also applicable to the aforementioned Embodiments 1 to 25 and embodiments without reference numerals.

Second Detector

Figure 24:
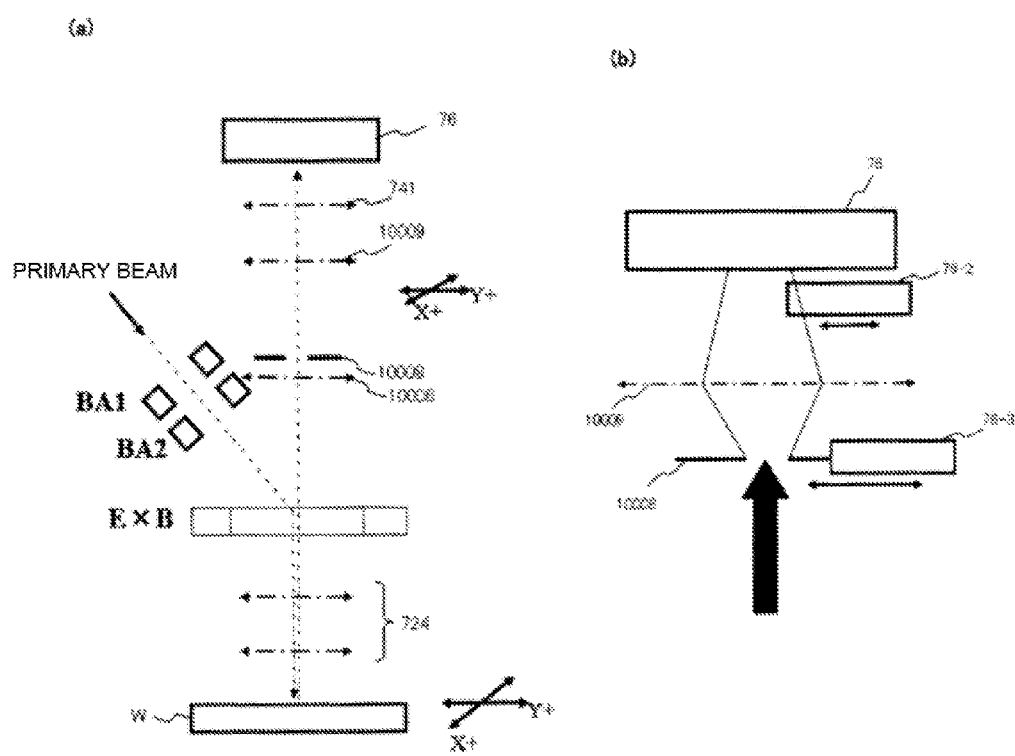
FIGS. 24A and 24B are diagrams showing a principle of a second detector according to an embodiment of the present invention.

As means that does not require frequent replacement of detectors and measures the position, the shape of the beam at the CO position and adjusts the optical axis, and as a detector for measuring the beam at the CO position, a second detector is provided immediately before a detector for inspection. FIGS. 24A and 24B are diagrams showing the principle of the second detector according to the invention of this application. FIG. 24A is a diagram showing the secondary optical system of the invention of this application. FIG. 24B is a diagram showing a state where an electron beam of secondarily released electrons and mirror electrons at a numerical aperture (NA) 10008 position is image-formed at a second detector 76-2 through a lens. Between the numerical aperture 10008 and the detection system 76 shown in FIG. 24B, the second detector 76-2 according to one embodiment of the invention of this application is provided to allow the movable numerical aperture (NA) 10008 to move and take an image of the position and the shape of the beam at the CO position at the second detector. Any shape at the CO position (or NA position) and position that allow a still image to be taken may be adopted. Adjustment is repeated on the basis of information on the taken image by the second detector 76-2, and inspection is performed after the adjustment.

The secondarily released electrons and the mirror electrons having passed through the numerical aperture (NA) 10008 are image-formed on the sensor surface of the detector. The thus formed two-dimensional electronic image is acquired by the second detector 76-2, converted into an electric signal, and transmitted to an image processing unit. In order to allow the second detector 76-2 to take an electron beam image at the CO position, a transfer lens or an electrostatic lens for enlarged projection may be adopted between the numerical aperture 10008 and the second detector 76-2.

An EB-CCD or a C-MOS type EB-CCD may be adopted as the second detector 76-2. The element has a size of ½ to ⅓ of element size of the EB-TDI, which is the first detector (detector 761). This configuration can take an image with a pixel size smaller than the size of the first detector. The pixel size is a value acquired by dividing the element size by the optical magnification, and is an image division size on the surface of the sample. For instance, with an element size of 10 μm☐ and a magnification of 1000, pixel size=10 μm/1000=10 nm. Any second detector having a smaller element size than the first detector has allows surface observation with a smaller pixel size than the size of the first detector. The EB-TDI of the first detector, and the EB-CCD or the C-MOS type EB-CCD of the second detector do not require a photoelectron conversion mechanism and an optical transmission mechanism. Electrons are immediately incident on the EB-TDI sensor surface or the EB-CCD sensor surface. Accordingly, the resolution is not degraded, and a high MTF (modulation transfer function) and contrast can be achieved. In comparison with the conventional EB-CCD, the C-MOS type EB-CCD can significantly reduce the background noise. Accordingly, the reduction is significantly effective for reducing noise due to the detector. In the case of imaging in the same conditions, the contrast can be improved and the S/N ratio can be improved in comparison with the conventional art. In particular, this configuration is effective for the case where the number of acquired electrons is small. In terms of noise reduction, this configuration can exert advantageous effects ⅓ to 1/20 as high as the effects of the conventional EB-CCD.

The beam passing through the numerical aperture (NA) 10008 and forming an image at the detector surface is detected by the second detector 76-2. On the basis of the position and the shape of the detected beam, condition creation of the electron beam and the position of the numerical aperture (NA) 10008 are adjusted. After various adjustments are performed on the basis of the detection results by the second detector 76-2, the sample is inspected using the detection system 76. Accordingly, since the detection system 76 is used only during inspection, the frequency of replacement of the detection system 76 can be suppressed. Since the second detector 76-2 takes only still images, degradation, if any, does not affect inspection. In order to achieve such image forming conditions, for instance, in the conditions for forming an electronic image at the first detector, and the conditions for forming an image at the second detector, and the conditions for forming an image at the second detector where the image is of the beam shape at the CO position for observing the beam at the CO position, these adjustments includes the cases where the lens intensity of the transfer lens 10009 is adjusted, and the optimal conditions for the first detector and the second detector are acquired, and the image forming conditions are used, with reference to FIG. 10A. The lens 741 may be adopted instead of the transfer lens 10009. The distance between the lens center and the detector is changed, and the magnification is changed accordingly between the case of using the transfer lens 10009 and the case of using the lens 741. Thus, a preferable lens and magnification may be selected.

The aforementioned second detector 76-2 can exert advantageous effects in the case of using the adjusting method according to the invention of this application that measures the position and shape of the beam at the CO position, creates the conditions for the electron beam and performs highly accurate adjustment. The second detector 76-2 can be applied not only to the electronic optical device including the new photoelectron generation portion according to the invention of this application but also to an electronic optical device including a typical electron gun. This embodiment is also applicable to the apparatuses described in Embodiments 1 to 3. In the example of the method of adjusting the beam and the NA position, the case where the primary beam is the electron beam has been described. However, the configuration is also applicable to the case where the irradiation system is the system with light or laser. The configuration is applicable to the case where laser or light is emitted, photoelectrons occur from the surface of the sample, and the size of the crossover of the photoelectrons and the relationship between the center position of the cross over and the NA setting position are appropriately defined. Accordingly, a photoelectron image with a high resolution can be formed.

Electronic Inspection Apparatus

Figure 25:
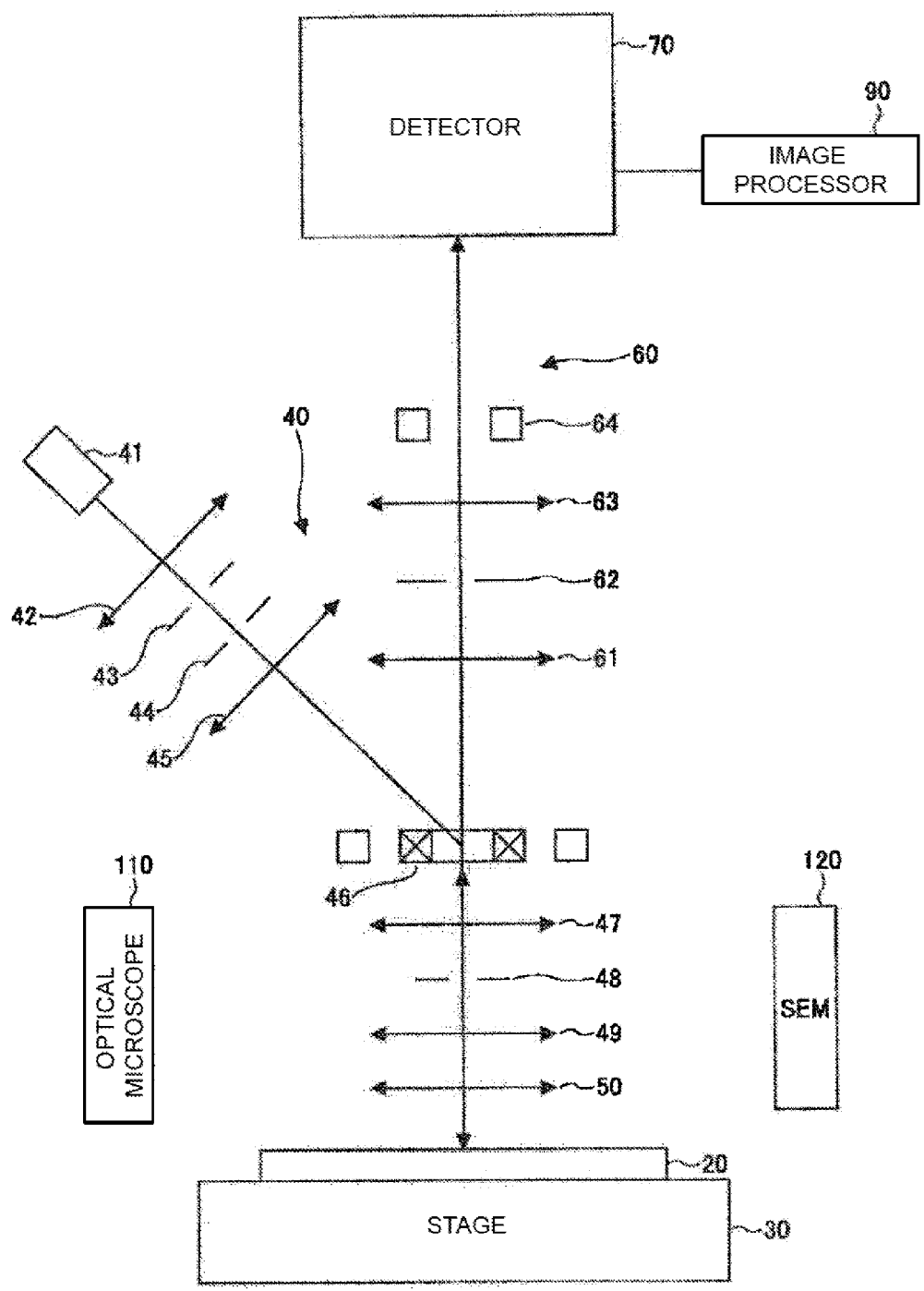
FIG. 25 is an electron beam inspection apparatus to which the present invention is applied, according to an embodiment of the present invention.

FIG. 25 is a diagram showing a configuration of an electron beam inspection apparatus to which the present invention is applied. The above description has been made mainly on the principle of the foreign matter inspection method. The foreign matter inspection apparatus applied to performing the foreign matter inspection method will herein be described. Accordingly all of the aforementioned foreign matter inspection methods are applicable to the following foreign matter inspection apparatus.

An inspection object of the electron beam inspection apparatus is a sample 20. The sample 20 is any of a silicon wafer, a glass mask, a semiconductor substrate, a semiconductor pattern substrate, and a substrate having a metal film. The electron beam inspection apparatus according to this embodiment detects presence of a foreign matter 10 on the surface of the sample 20 that is any one of these substrates. The foreign matter 10 is insulative material, conductive material, semiconductor material, or a composite thereof. The types of the foreign matter 10 include particles, cleaning residues (organic matters), reaction products on the surface and the like. The electron beam inspection apparatus may be an SEM type apparatus or a mapping projection apparatus. In this example, the present invention is applied to the mapping projection inspection apparatus.

The mapping projection type electron beam inspection apparatus includes: a primary optical system 40 that generates an electron beam; a sample 20; a stage 30 on which the sample is mounted; a secondary optical system 60 that forms an enlarged image of secondarily released electrons or mirror electrons from the sample; a detector 70 that detects the electrons; an image processor 90 (image processing system) that processes a signal from the detector 70; an optical microscope 110 for alignment; and an SEM 120 for review. In the present invention, the detector 70 may be included in the secondary optical system 60. The image processor 90 may be included in the image processor of the present invention.

The primary optical system 40 generates an electron beam, and irradiates the sample 20. The primary optical system 40 includes an electron gun 41; lenses 42 and 45; apertures 43 and 44; an ExB filter 46; lenses 47, 49 and 50; and an aperture 48. The electron gun 41 generates an electron beam. The lenses 42 and 45 and apertures 43 and 44 shape the electron beam and control the direction of the electron beam. In the ExB filter 46, the electron beam is subjected to a Lorentz force due to a magnetic field an electric field. The electron beam enters the ExB filter 46 in an inclined direction, is deflected into a vertically downward direction, and travels toward the sample 20. The lenses 47, 49 and 50 control the direction of the electron beam and appropriately decelerate, thereby controlling the landing energy LE.

The primary optical system 40 irradiates the sample 20 with the electron beam. As described above, the primary optical system 40 performs irradiation with both an electron beam for precharging and an imaging electron beam. In experiment results, the difference between a precharging landing energy LE1 and a landing energy LE2 for an imaging electron beam is preferably 5 to 20 [eV].

In terms of this point, it is provided that in the case with a potential difference between the potential of the foreign matter 10 and the potential therearound, the precharging landing energy LE1 is emitted in a negative charging region. In conformity with the value of LE1, the charging up voltage varies. This variation is because of variation in a relative ratio of the LE1 and the LE2 (LE2 is a landing energy of the imaging electron beam as described above). If the LE1 is high, the charging up voltage is high. Accordingly, a reflection point is formed at an upper position of the foreign matter 10 (position close to the detector 70). The trajectory and transmittance of the mirror electrons vary according to the reflection point. Thus, the optimal charging-up voltage conditions are determined according to the reflection point. If the LE1 is too low, an efficiency of forming the mirror electrons reduces. The present invention has found that the difference between the LE1 and the LE2 is preferably 5 to 20 [eV]. The value of the LE1 is preferably 0 to 40 [eV], and further preferably 5 to 20 [eV].

In the primary optical system 40 of the mapping projection optical system, the ExB filter 46 is particularly important. The primary electron beam angle can be defined by adjusting the conditions of the electric field and the magnetic field of the ExB filter 46. For instance, the irradiation electron beam of the primary system and the electron beam of the secondary system can set the conditions of ExB filter 46 so as to make the incidence substantially rectangular to the sample 20. In order to further increase the sensitivity, for instance, it is effective to incline the incident angle of the electron beam of the primary system with respect to the sample 20. An appropriate inclined angle is 0.05 to 10 degrees, preferably is about 0.1 to 3 degrees.

Thus, the signal from the foreign matter 10 is strengthened by emitting the electron beam at an inclination of a prescribed angle θ with respect to the foreign matter 10. Accordingly, conditions where the trajectory of the mirror electron does not deviate from the center of the secondary optical axis can be formed. Thus, the transmittance of the mirror electron can be increased. Accordingly, in the case where the foreign matter 10 is charged up and the mirror electrons are guided, the inclined electron beam is significantly efficiently used.

Referring again to FIG. 25, the stage 30 is means for mounting the sample 20, and movable in the horizontal x-y directions and the θ direction. The stage 30 may be also movable in the z direction as necessary. Means for fixing a sample, such as an electrostatic chuck, may be provided on the surface of the stage 30.

The sample 20 is on the stage 30. The foreign matter 10 is on the sample 20. The primary optical system 40 irradiates the surface 21 of the sample with the electron beam at a landing energy LE of 5 to −10 [eV]. The foreign matter 10 is charged up, incident electrons in the primary optical system 40 recoil without coming into contact with the foreign matter 10. Accordingly, the mirror electrons are guided by the secondary optical system 60 to the detector 70. Here, the secondarily released electrons are released from the surface 21 of the sample in spread directions. Accordingly, the transmittance of the secondarily released electrons is a low value, for instance, about 0.5 to 4.0%. In contrast, the direction of the mirror electron is not scattered. Accordingly, a transmittance of the mirror electrons of about 100% can be achieved. The mirror electrons are formed on the foreign matter 10. Thus, only the signal of the foreign matter 10 can achieve a high luminance (the state with the large amount of electrons). The difference of the luminance from the ambient secondarily released electrons and the ratio of the luminance increase, thereby allowing high contrast to be achieved.

As described above, the image of the mirror electron is enlarged at a magnification higher than the optical magnification. The magnification ratio reaches 5 to 50. In typical conditions, the magnification ratio is often 20 to 30. Here, even if the pixel size is three times as large as the size of the foreign matter, the foreign matter can be found. Accordingly, high speed and high throughput can be achieved.

For instance, in the case where the size of the foreign matter 10 has a diameter of 20 [nm], it is sufficient that the pixel size is 60 [nm], 100 [nm], 500 [nm] or the like. As with this example, the foreign matter can be imaged and inspected using the pixel size three times as large as the size of the foreign matter. This feature is significantly excellent for high throughput in comparison with the SEM system and the like.

The secondary optical system 60 is means for guiding electrons reflected by the sample 20 to the detector 70. The secondary optical system 60 includes lenses 61 and 63, a NA aperture 62, an aligner 64, and a detector 70. The electrons are reflected by the sample 20, and pass again through the objective lens 50, the lens 49, the aperture 48, the lens 47 and the ExB filter 46. The electrons are then guided to the secondary optical system 60. In the secondary optical system 60, electrons pass through the lens 61, the NA aperture 62 and the lens 63 and are accumulated. The electrons are adjusted by the aligner 64, and detected by the detector 70.

The NA aperture 62 has a function of defining the secondary transmittance and aberrations. The size and the position of the NA aperture 62 are selected such that the difference between the signal from the foreign matter 10 (mirror electron etc.) and the signal from the ambient portions (normal portions) is large. Instead, the size and the position of the NA aperture 62 are selected such that the ratio of the signal from the foreign matter 10 with respect to the ambient signal is large. Thus, the S/N ratio can be high.

For instance, it is provided that the NA aperture 62 can be selected in a range of φ50 to φ3000 [μm]. Detected electrons are mixture of mirror electrons and secondarily released electrons. In such situations, the aperture size is effectively selected in order to improve the S/N ratio of the mirror electron image. In this case, it is preferred to select the size of the NA aperture 62 such that the transmittance of the mirror electrons is maintained by reducing the transmittance of the secondarily released electrons.

For instance, in the case where the incident angle of the primary electron beam is 3°, the reflection angle of the mirror electrons is about 3°. In this case, it is preferred to select the size of the NA aperture 62 that allows the trajectory of the mirror electrons to pass. For instance, the appropriate size is φ250 [μm]. Because of the limitation to the NA aperture (diameter φ250 [μm]), the transmittance of the secondarily released electrons is reduced. Accordingly, the S/N ratio of the mirror electron image can be improved. For instance, in the case where the aperture diameter is from φ2000 to φ250 [μm], the background gradation (noise level) can be reduced to ½ or less.

Referring again to FIG. 25, the detector 70 is means for detecting electrons guided by the secondary optical system 60. The detector 70 has a plurality of pixels on the surface. Various two-dimensional sensor may be adopted as the detector 70. For instance, the detector 70 may be any of a CCD (charge coupled device) and a TDI (time delay integration)-CCD. These are sensors that convert electrons into light and then detect signals. Accordingly, photoelectronic conversion means is required. Thus, electrons are converted into light using photoelectronic conversion or a scintillator. Optical image information is transmitted to the TDI that detects light. The electrons are thus detected.

Here, an example where the EB-TDI is applied to the detector 70 will be described. The EB-TDI does not require a photoelectronic conversion mechanism and an optical transmission mechanism. The electrons are directly incident on the EB-TDI sensor surface. Accordingly, the high MTF (modulation transfer function) and contrast can be acquired without degradation in resolution. Conventionally, detection of small foreign matters 10 has been unstable. In contrast, use of the EB-TDI can improve the S/N ratio of a weak signal of the small foreign matters 10. Accordingly, a higher sensitivity can be achieved. The S/N ratio improves by a factor of 1.2 to 2.

In addition to the EB-TDI, an EB-CCD may be provided. The EB-TDI and the EB-CCD can be replaced with each other, and can be arbitrarily switched. Such a configuration may also be effective. For instance, a method of use as shown in FIG. 26 is applied.

Figure 26:
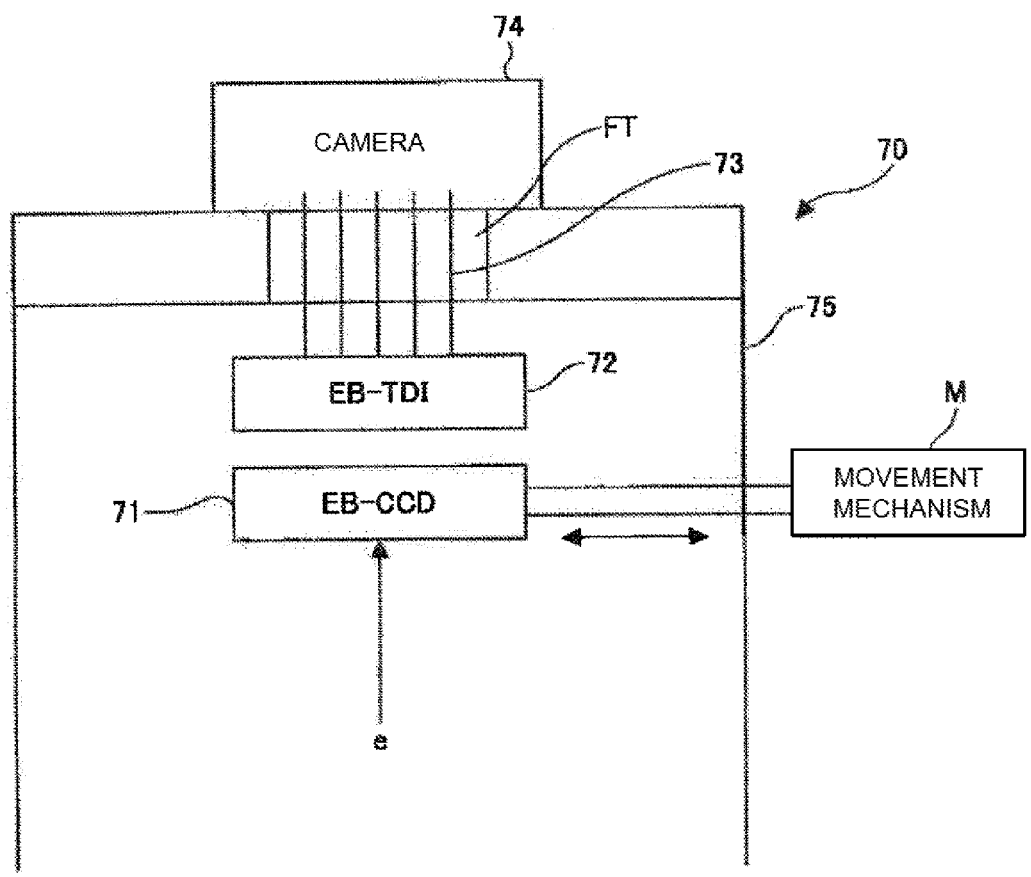
FIG. 26 is a diagram showing a detector that can switch EB-TDI and EB-CCD, according to an embodiment of the present invention.

FIG. 26 shows the detector 70 that can switches an EB-TDI 72 and the EB-CCD 71 from each other. The two sensors can be replaced with each other according to usage. Both the sensors can be used.

In FIG. 26, the detector 70 includes the EB-CCD 71 and the EB-TDI 72 provided in the vacuum container 75. The EB-CCD 71 and the EB-TDI 72 are electronic sensors that receive an electron beam. The electron beam e is directly incident on the detection surface. In this configuration, the EB-CCD 71 is used to adjust the optical axis of the electron beam, and to adjust and optimize image taking conditions. Instead, in the case of using the EB-TDI 72, the EB-CCD 71 is moved to a position apart from the optical axis by a movement mechanism M. The EB-TDI 72 then takes an image through use or in consideration of the conditions acquired using the EB-CCD 71. Evaluation or measurement is performed using the image. The movement mechanism M may be configured to allow movement not only in the direction (X direction) where the EB-CCD 71 moves but also along the three axes (e.g., X, Y and Z directions), and allow the center of the EB-CCD 71 to be finely adjusted with respect to the center of the optical axis of the electronic optical system.

In the detector 70, the EB-TDI 72 can detect the foreign matters on the semiconductor wafer through use or with reference to the electronic optical conditions acquired using the EB-CCD 71.

After foreign matter detection by the EB-TDI 72, review imaging may be performed using the EB-CCD 71. Defects, such as the types and the sizes of foreign matters, may be evaluated. The EB-CCD 71 can integrate images. The integration can reduce the noise. Accordingly, review imaging can be performed on defect detection portions at a high S/N ratio. Furthermore, it is effective that the pixel of the EB-CCD 71 is smaller than the pixel of the EB-TDI 72. That is, the number of pixels of the image pickup element can be increased in comparison with the size of the signal enlarged by the mapping projection optical system. Accordingly, an image having a higher resolution can be acquired. The image is used for inspection and classifying and determining the types of defects.

The EB-TDI 72 has a configuration where the pixels are two-dimensionally arranged. For instance, the EB-TDI has a rectangular shape. Thus, the EB-TDI 72 can directly receive the electron beam e and form an electronic image. The pixel size is, for instance, 12 to 16 [µm]. Meanwhile, the pixel size of the EB-CCD 71 is, for instance, 6 to 8 [µm].

The EB-TDI 72 is formed into a package. The package itself functions as feedthrough FT. Pins 73 of the package are connected to a camera 74 on the atmosphere side.

The configuration shown in FIG. 26 can cancel the various drawbacks. The canceled drawbacks include optical conversion loss due to FOP, hermetic optical glass, optical lens and the like, aberrations and distortion during light transmission, degradation in image resolution thereof, poor detection, high cost, increase in size and the like.

Figure 27:
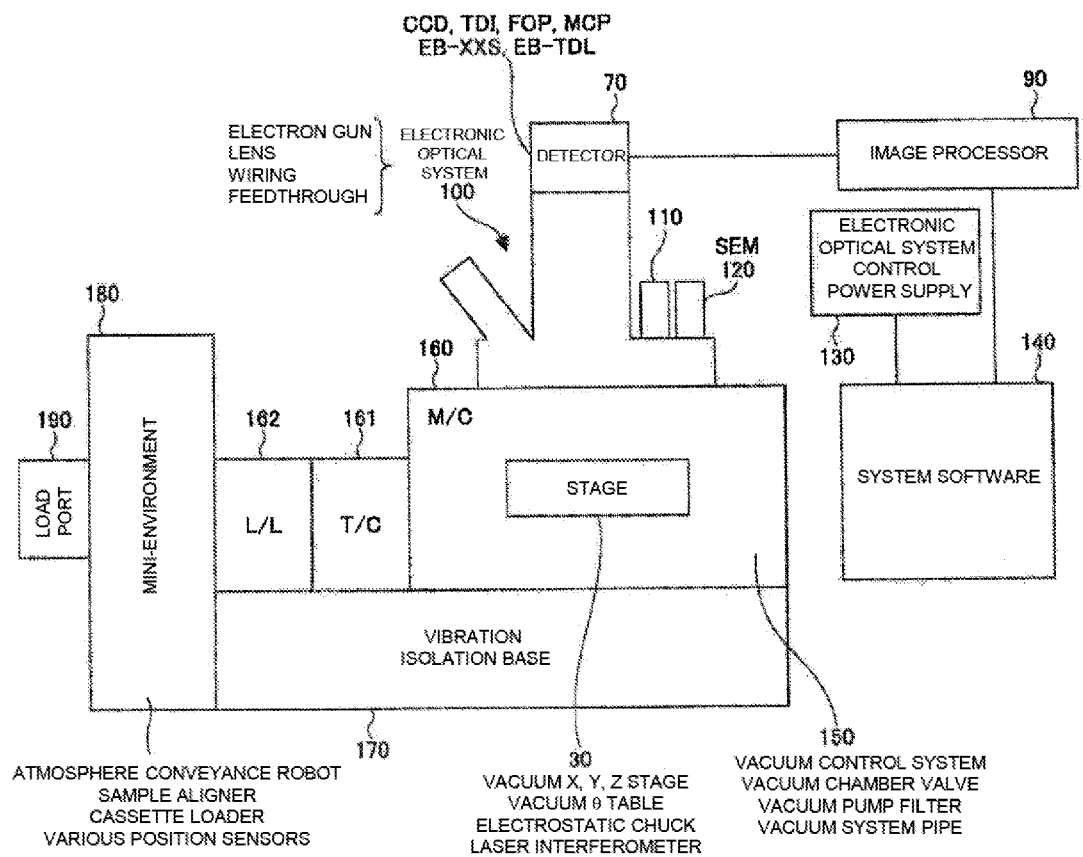
FIG. 27 is a diagram showing an electron beam inspection apparatus to which the present invention is applied, according to an embodiment of the present invention.

FIG. 27 shows an electron beam inspection apparatus to which the present invention is applied. Here, an example of the entire system configuration will be described.

In FIG. 27, the foreign matter inspection apparatus includes: a sample carrier 190; a mini-environment 180; a load lock 162; a transfer chamber 161; a main chamber 160; an electron beam column system 100; and an image processor 90. A conveyance robot in the atmosphere, a sample alignment device, clean air supply mechanism and the like are provided in the mini-environment 180. A conveyance robot in a vacuum is provided in the transfer chamber 161. The robots are arranged in the transfer chamber 161 that is always in a vacuum state. Accordingly, occurrence of particles and the like due to pressure variation can be suppressed to the minimum.

The stage 30 that moves in the X and Y directions and the θ (turning) direction is provided in the main chamber 160. An electrostatic chuck is provided on the stage 30. The sample 20 itself is provided at the electrostatic chuck. Instead, the sample 20 is held by the electrostatic chuck in a state of being arranged on a pallet or a jig.

The main chamber 160 is controlled by the vacuum control system 150 such that the inside of the chamber is kept in a vacuum. The main chamber 160, the transfer chamber 161 and the load lock 162 are mounted on a vibration isolation base 170. The configuration prevents vibrations from the floor from being transmitted.

An electron column 100 is provided on the main chamber 160. The electron column 100 includes: columns of a primary optical system 40 and a secondary optical system 60; and a detector 70 that detects secondarily released electrons, mirror electrons and the like from the sample 20. The signal from the detector 70 is transmitted to the image processor 90 and processed. Both on-time signal processing and off-time signal processing can be performed. The on-time signal processing is performed during inspection. In the case of off-time signal processing, only an image is acquired and the signal processing is performed thereafter. Data processed in the image processor 90 is stored in recording media, such as a hard disk and memory. The data can be displayed on a monitor of a console, as required. The displayed data is, for instance, an inspection region, a map of the number of foreign matters, the size distribution and map of foreign matters, foreign matter classification, a patch image and the like. System software 140 is provided in order to perform signal processing. An electronic optical system control power supply 130 is provided in order to supply power to the electron column system. The optical microscope 110 and the SEM inspection apparatus 120 may be provided in the main chamber 160.

Figure 28:
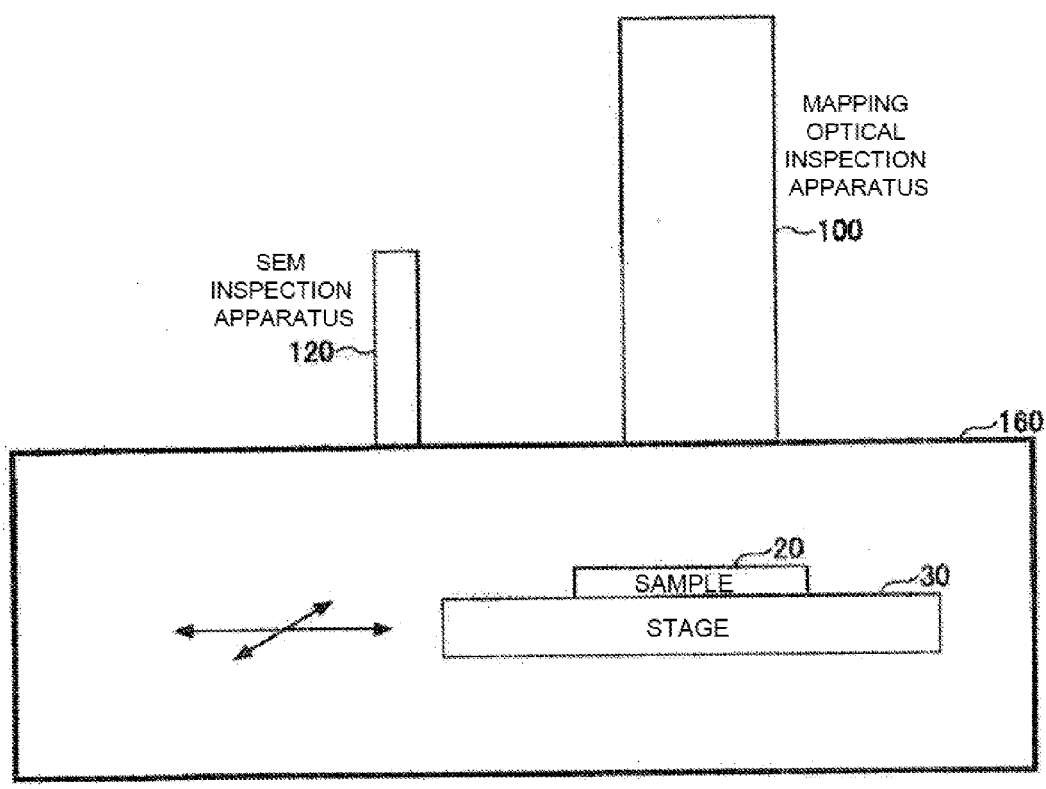
FIG. 28 is a diagram showing an example of a configuration where an electron column of a mapping optical system inspection apparatus and an SEM inspection apparatus are provided in the same main chamber, according to an embodiment of the present invention.

FIG. 28 shows an example of a configuration in the case where an electron column 100 and an SEM inspection apparatus 120 of a mapping optical system inspection apparatus are provided in the same main chamber 160. The arrangement of the mapping optical system inspection apparatus and the SEM inspection apparatus 120 in the same chamber 160 as shown in FIG. 28 is significantly advantageous. A sample 20 is mounted on the same stage 30. The sample 20 can be observed or inspected according to the mapping system and SEM system. A method of using this configuration and advantageous effects thereof are as follows.

Since the sample 20 is mounted on the same stage 30, the coordinate relationship is uniquely defined when the sample 20 is moved between the mapping system electron column 100 and the SEM inspection apparatus 120. Accordingly, when the detection positions of foreign matters are identified, two inspection apparatuses can easily highly accurately identify the same position.

In the case where above configuration is not applied, for instance, the mapping optical inspection apparatus and the SEM inspection apparatus 120 are configured to be separated from each other as different apparatuses. The sample 20 is moved between the separated apparatuses. In this case, the sample 20 is required to be mounted on the separate stages 30. Accordingly, the two apparatuses are required to separately align the sample 20. In the case of separately aligning the sample 20, specific errors at the same position are unfortunately 5 to 10 [μm]. In particular, in the case of the sample 20 with no pattern, the positional reference cannot be identified. Accordingly, the error further increases.

In contrast, in this embodiment, as shown in FIG. 28, the sample 20 is mounted on the stage 30 in the same chamber 160 in two types of inspections. Even in the case where the stage 30 is moved between the mapping type electron column 100 and the SEM inspection apparatus 120, the same position can be highly accurately identified. Accordingly, even in the case of the sample 20 with no pattern, the position can be highly accurately identified. For instance, the position can be identified at an accuracy of 1 [μm] or less.

Such highly accurate identification is significantly advantageous in the following case. First, foreign matter inspection on the sample 20 with no pattern is performed according to the mapping method. The detected foreign matter 10 is then identified and observed (reviewed) in detail by the SEM inspection apparatus 120. Since the accurate position can be identified, not only presence or absence of the foreign matter 10 (pseudo-detection in the case of absence) can be determined but also the size and shape of the foreign matter 10 can be observed in detail at high speed.

As described above, the separate arrangement of the electron column 100 for detecting foreign matters and the SEM inspection apparatus 120 for reviewing takes much time for identifying the foreign matter 10. In the case of the sample with no pattern, the difficulty is increased. Such problems are solved by this embodiment.

As described above, in this embodiment, through use of the imaging conditions for the foreign matter 10 according to the mapping optical system, a significantly fine foreign matter 10 can be highly sensitively detected. Furthermore, the mapping optical type electron column 100 and the SEM inspection apparatus 120 are mounted in the same chamber 160. Thus, in particular, inspection on the significantly fine foreign matter 10 with a dimension of 30 [nm] or less determination and classification of the foreign matter 10 can be performed significantly efficiently at high speed. This embodiment is also applicable to the aforementioned Embodiments 1 to 3 and embodiments to which no numeral is assigned.

Next, another example using both the mapping projection type inspection apparatus and the SEM will be described.

The above description has been made where the mapping projection type inspection apparatus detects the foreign matters and the SEM performs reviewing inspection. However, the present invention is not limited thereto. The two inspection apparatuses can be applied to another method. Combination of the inspection apparatuses can perform effective inspection. For instance, the other method is as follows.

In this inspection method, the mapping projection type inspection apparatus and the SEM inspect respective regions different from each other. Furthermore, the "cell to cell (cell to cell)" inspection is applied to the mapping projection type inspection apparatus, and the "die to die (die to die)" inspection is applied to the SEM. Accordingly, highly accurate inspection is effectively achieved as a whole.

More specifically, the mapping projection type inspection apparatus performs "cell to cell" inspection in a region with many repetitive patterns in the die. The SEM performs the "die to die" inspection in a region with a small number of repetitive patterns. Both inspection results are combined and one inspection result is acquired. The "die to die" inspection compares images of two dice that are sequentially acquired. The "cell to cell" inspection compares images of two cells that are sequentially acquired. The cell is a part of a die.

The inspection method performs high speed inspection using mapping projection on repetitive pattern portions while performing inspection on regions with a small number of repetitive patterns using the SEM that can achieve high accuracy and small number of artifacts. The SEM is not suitable to high speed inspection. However, since the region with a small number of repetitive patterns is relatively narrow, the inspection time by the SEM is not too long. Accordingly, the entire inspection time can be suppressed short. Thus, this inspection method can take advantage of the two methods at the maximum, and perform highly accurate inspection in a short inspection time.

Next, referring again to FIG. 27, the mechanism of conveying the sample 20 will be described.

The sample 20, such as a wafer or a mask, is conveyed through a load port into the mini-environment 180, and an alignment operation is performed in the environment. The sample 20 is conveyed to the load lock 162 by the conveyance robot in the atmosphere. The load lock 162 is evacuated from the atmosphere to a vacuum state by the vacuum pump. After the pressure becomes below a prescribed value (about 1 [Pa]), the sample 20 is conveyed by the conveyance robot in the vacuum disposed in the transfer chamber 161 from the load lock 162 to the main chamber 160. The sample 20 is mounted on the electrostatic chuck mechanism on the stage 30.

Light+EB Irradiation

An embodiment in the case with two types of primary systems will be described.

It is also significantly effective to form an image using combination of a photoelectron image by irradiation with light or laser and secondarily released electrons and/or mirror electrons (cases with and without mirror electrons) by irradiation with an electron beam. Here, secondarily released electrons are in states where a part or mixture of secondary electrons, reflected electrons, and backscattering electrons. In particular, in the case of a low LE, it is difficult to discriminate the states from each other.

Figure 7:
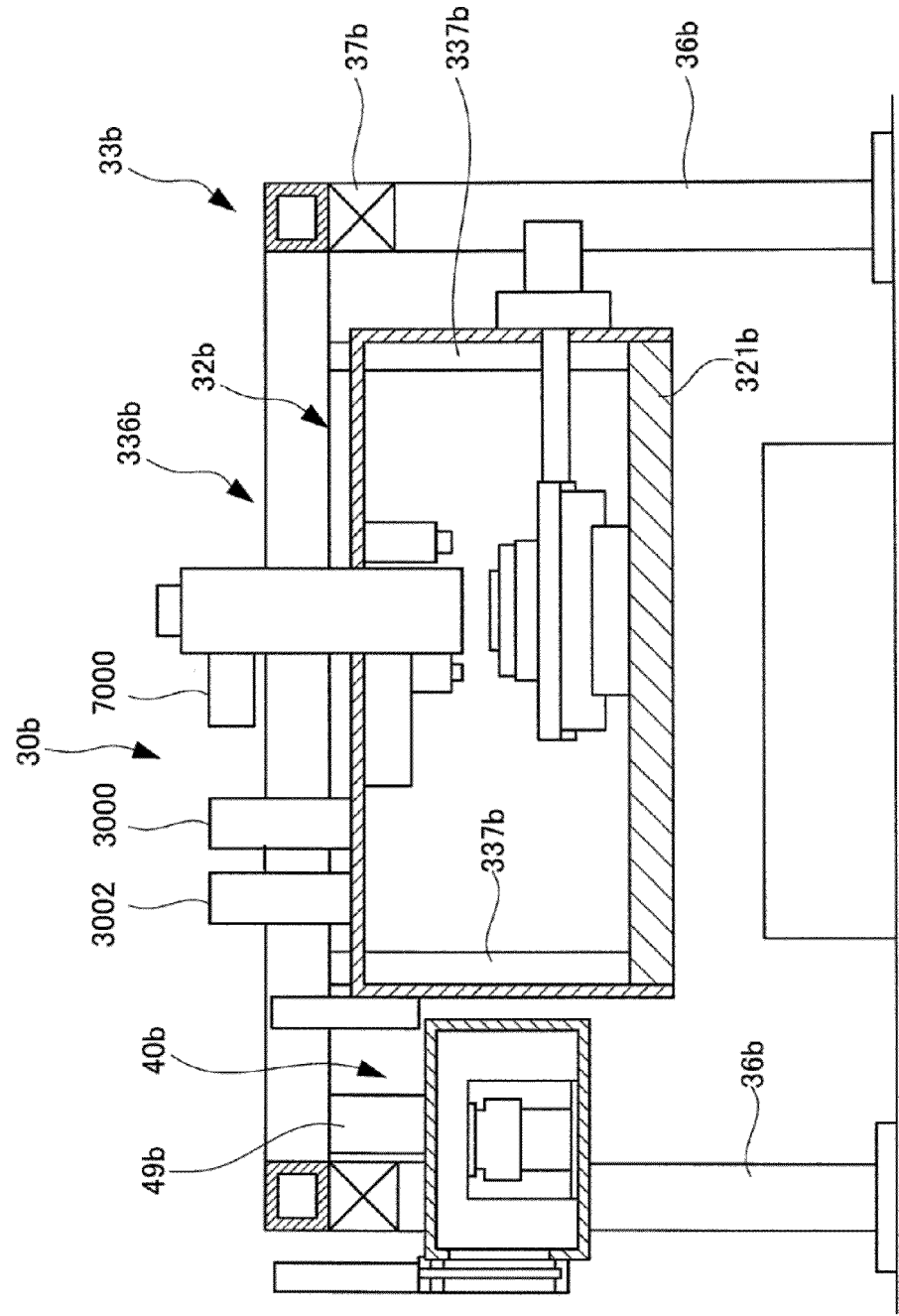
FIG. 7 is a variation of the method of supporting a main housing.
Figure 29:
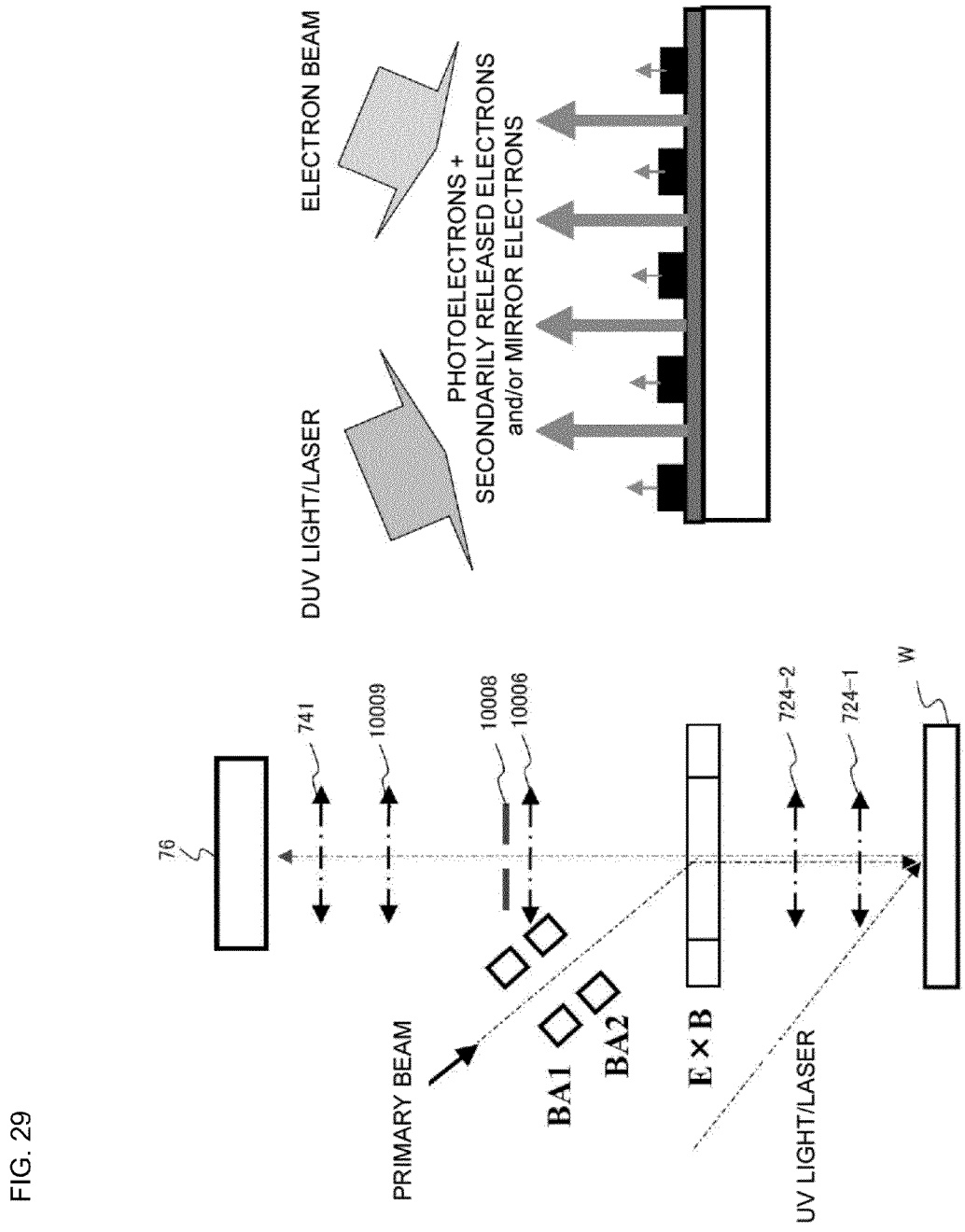
FIG. 29 is a diagram showing an example of an exemplary configuration that integrates a mode of irradiating a sample with light or laser and a mode of irradiating the sample with an electron beam in a primary system, according to an embodiment of the present invention.
Figure 30:
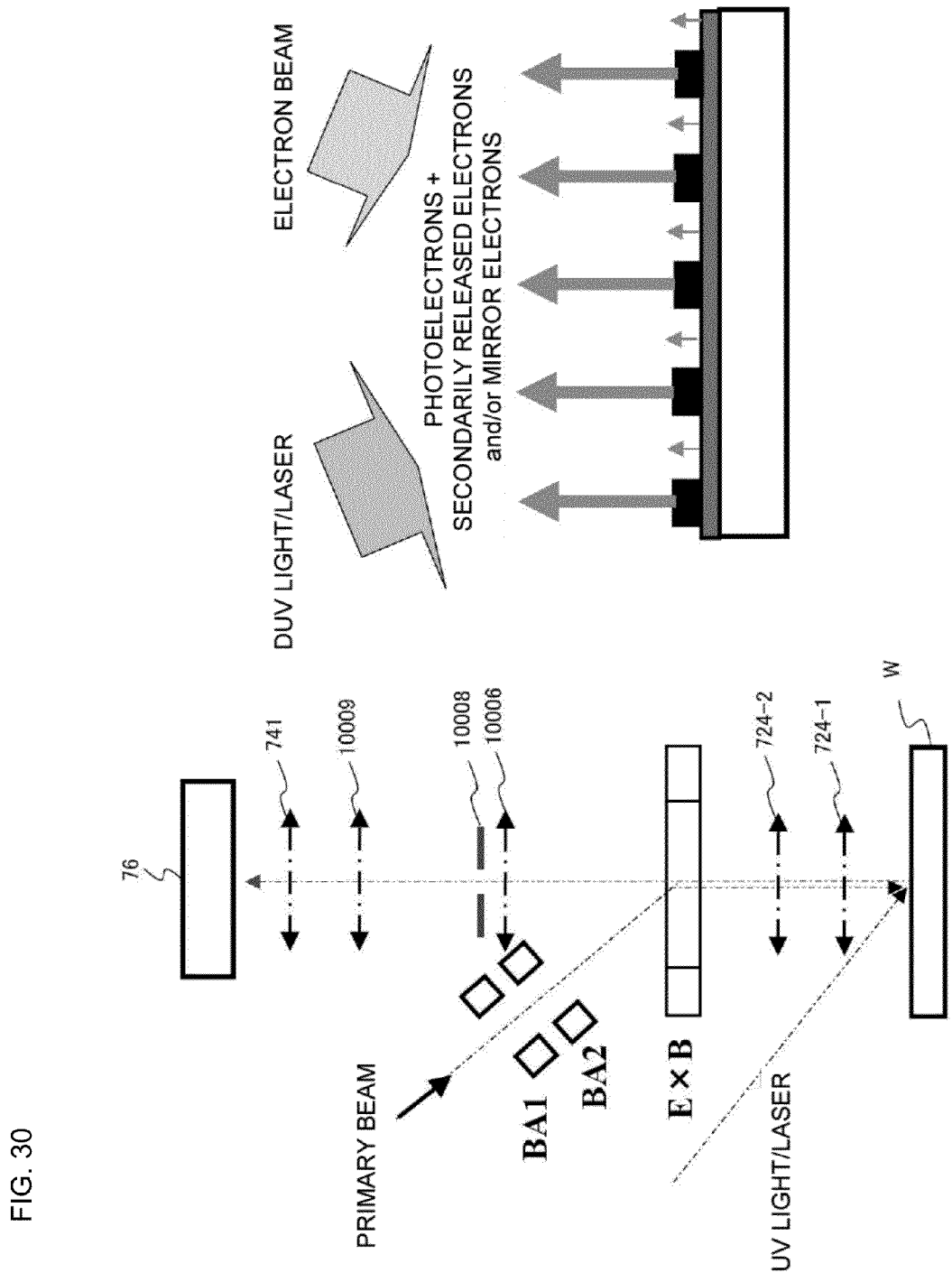
FIG. 30 is a diagram showing an example of an exemplary configuration that integrates a mode of irradiating a sample with light or laser and a mode of irradiating the sample with an electron beam in a primary system, according to an embodiment of the present invention.
Figure 31:
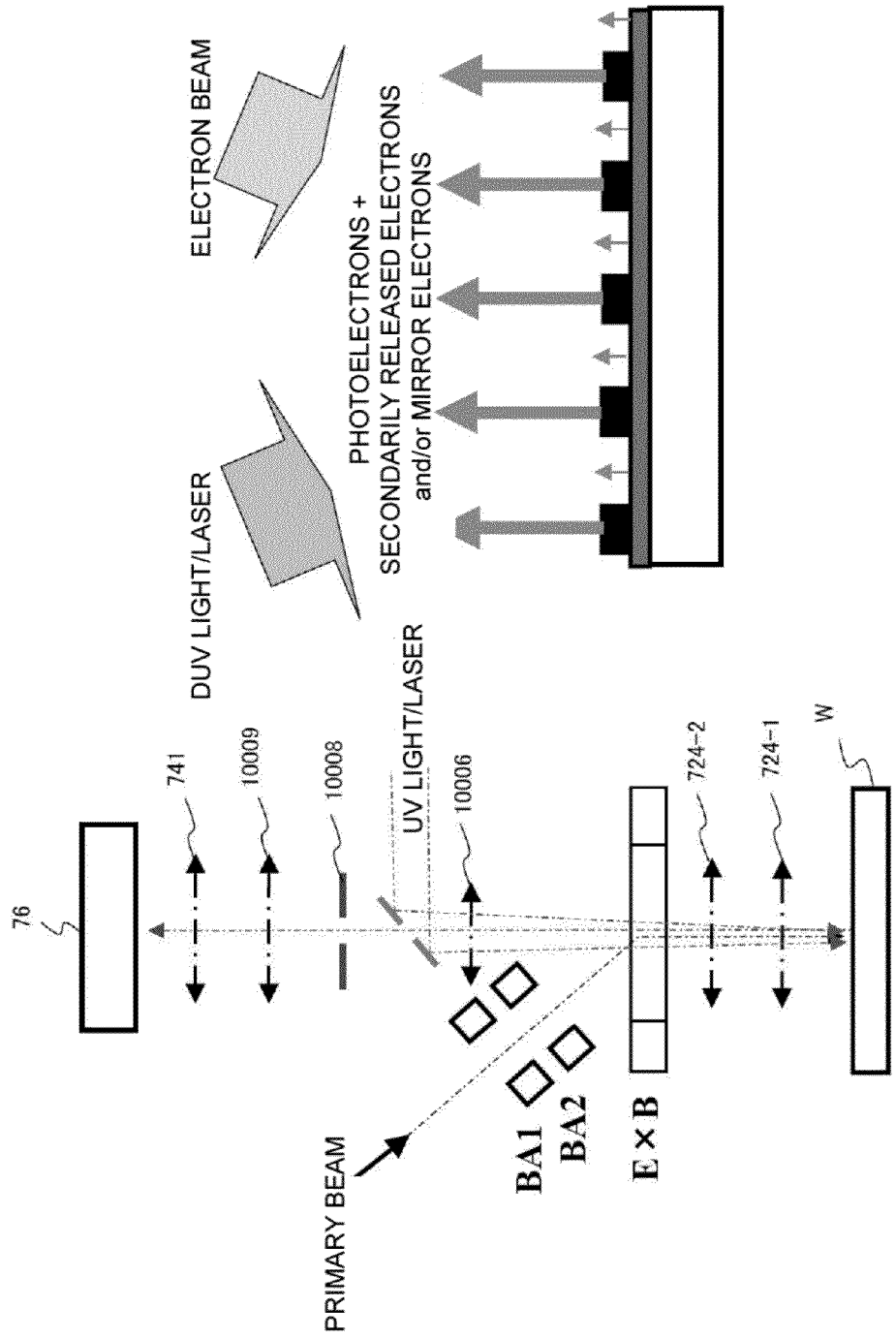
FIG. 31 is a diagram showing an example of an exemplary configuration that integrates a mode of irradiating a sample with light or laser and a mode of irradiating the sample with an electron beam in a primary system, according to an embodiment of the present invention.

An embodiment will be described where the embodiments of irradiating the sample with light or laser in FIGS. 7 to 9 and the embodiments of irradiating the sample with the electron beam in the primary system in FIGS. 10A to 19 are integrated. FIGS. 29, 30 and 31 show examples of the embodiment. An example where a sample has a asperity shape will be described.

In this example, irradiation with laser (or light) and irradiation with an electron beam are simultaneously performed as the primary beam. A method of simultaneous irradiation and a method of temporally alternate irradiation can be adopted. The characteristics of the laser irradiation and the characteristics of electron beam irradiation in this case will be described, and advantageous effects and working operations in the case of integration will be described.

In the case where irradiation with laser causes a large amount of photoelectrons on the top layer (bumps) to be represented as a white signal, and irradiation with an electron beam causes a large amount of secondarily released electrons on the top layer to be represented as a white signal, combination of a photoelectron image and a secondarily released electron image can increase the amount of electrons on the top layer (white photoelectrons+secondarily released electrons and/or white mirror electrons). That is, an image where the top layer (bumps) is white and pits are black can be formed, which can improve the contrast and the S/N ratio.

On the contrary, in the case where a large amount of photoelectrons occur at the pits to be represented as a white signal, and a large amount of secondarily released electrons occur at pits to be represented as a white signal, simultaneous irradiation with laser and irradiation with an electron beam (combination) can improve the contrast and the S/N ratio of an image formed such that the pits are white (white photoelectrons+secondarily released electrons and/or white mirror electron) and the top layer (bumps) is black. Here, the white signal represents that the number of detected electrons is larger than the number in the other portions, and the luminance is relatively high, i.e., the state is represented as white and an image can be taken as white.

As shown in FIG. 10A, in the case of using the electron beam, an electron beam separator, such as E×B, is necessary to make separation from the secondary beam (the Wien filter or the like is used that allows the secondary beam to straightly pass). Accordingly, such an electron beam separator is also required for the embodiment in which the electron beam and laser or light are integrated. FIGS. 29, 30, and 31 show the examples.

The differences between FIGS. 29, 30 and 31 are as follows. The cases in FIGS. 29 and 30 have a mechanism of introducing laser (or light) on the sample side with respect to the E×B. The case in FIG. 31 has a mechanism of introducing laser (or light) on the detector side with respect to the E×B. For instance, in FIGS. 29 and 30, a system where a hole for introducing laser is provided at a cathode lens, and a sample is irradiated with the laser in a state of being aligned by a mirror and the like outside of the chamber, and a system where a fiber and a lens are introduced to a cathode lens and irradiation with laser is performed are allowed. In FIG. 31, a mirror element is provided in the secondary column, laser is introduced from the outside of the column, and the sample can be irradiated with the laser (or light). FIG. 31 shows the case where a large amount of electrons occur at the bumps owing to irradiation with laser and irradiation with the electron beam (white signal). Also in the case where a large amount of electrons occurs at the pits (white signal), analogous operations can be performed as with FIG. 29.

It is more effective to use the electron beam in the primary system described in the embodiments as shown in FIGS. 12 to 18. Since irradiation with an electron beam with a narrow band energy is allowed at a large current, the energies of the formed secondarily released electrons and mirror electrons are in a narrow band. Accordingly, a high resolution image with small aberrations and blurring can be formed. The energy of the photoelectrons due to irradiation with laser is in a narrower band than the secondarily released electrons is. Accordingly, even with integration and combination, the energy remains in the narrow band state. Thus, an advantageous effect is exerted where, even though the amount of electrons increases, the energy width does not increase. This effect can be achieved without degrading the image quality in the case where the laser and the electron beam for irradiation are increased to improve the throughput. This feature is significantly effective and useful.

On the contrary, a combination is also allowed where the photoelectrons are represented as white and the secondarily released electrons are represented as black. In this case, a combined image is represented as gray, which is an neutral color between white and black. Accordingly, the resolution and the contrast of the pattern are degraded. Here, observation can be made where only defects are represented as a strong white signal or a strong black signal. In this case, for instance, if the defects are sensitive to light irradiation, a white or black signal can be formed by increasing or reducing the amount of photoelectrons. If the defects are sensitive to the electronic irradiation, a white or black signal can be formed by increasing or reducing the amount of secondarily released electrons.

Likewise, a combination is allowed where the photoelectrons are represented as black and the secondarily released electrons are represented as white. In the example of the EUV mask, the following combination is allowed for TaBO on the top layer and Ru at the pits.

Combination of Photoelectron Image with White Ru/Black TaBO, and Image of Secondarily Released Electrons and/or Mirror Electrons; Combination of Black Ru/White TaBO Photoelectron Image and Image of Secondarily Released Electrons and/or Mirror Electrons This combination can achieve high contrast and a high S/N ratio, and highly sensitively inspect pattern defects and foreign matters.

On a low LE image, the oxide film potential is stabilized by light irradiation. It is significantly effective in the case where the low LE with electronic irradiation energy where −5 eV<LE<10 eV, particularly in the case where the material of the top layer is of an oxide film. In the case where the top layer is an oxide film, irradiation with the low LE electron beam charges the oxide film in a negative voltage. The adverse effect degrades the image quality. Furthermore, the current density cannot be increased. Here, irradiation with light, such as UV, DUV, EUV and X-rays, or laser can control the potential of the oxide film. Irradiation with such light causes photoelectrons, which allows positive charging. Accordingly, the low LE and simultaneous or intermittent irradiation with light or laser can control the potential of the oxide film to be constant. Since the potential is kept constant, the image quality is stabilized and stable image formation can be achieved. Accordingly, the throughput can be improved.

Embodiment 5

Uniform and Stable Supply of Sample Surface Potential

Figure 33A:
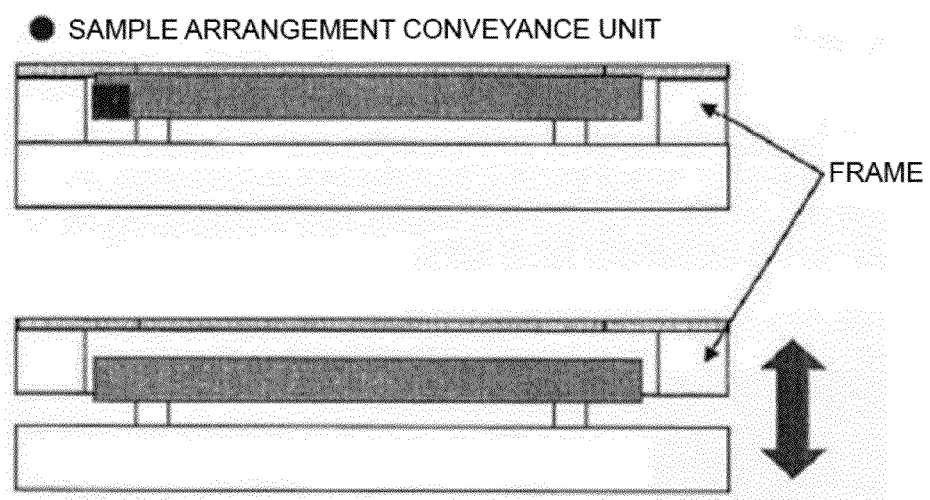
FIG. 33A is a diagram showing an example of uniform and stable supply of sample surface potential, according to an embodiment of the present invention.
Figure 33B:
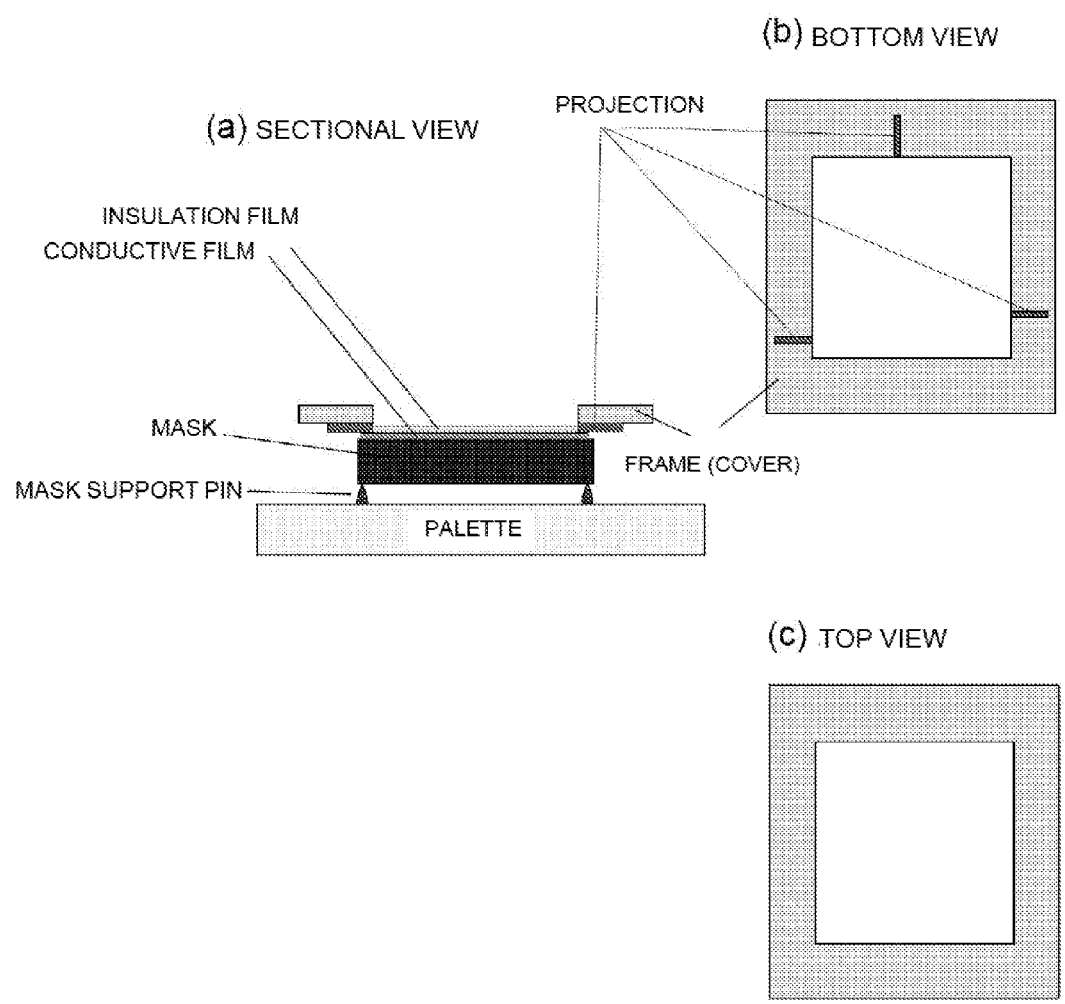
FIG. 33B is a diagram showing an example of uniform and stable supply of sample surface potential, according to an embodiment of the present invention.

Referring to FIGS. 32, 33A and 33B, an example of uniform and stable supply of a sample surface potential in the inspection apparatus and the inspection method of the present invention will be described. In the mapping projection type defect inspection apparatus, a voltage is required to be applied to the sample surface. Appearance of the surface state and appearance of defects are adjusted by changing the voltage applied to the sample surface. That is, if the voltage distribution on the sample surface is uneven, the conditions vary according to differences of voltage distributions. The variation causes a problem of affecting reproducibility and the like.

Thus, an application method is proposed such that the voltage distribution on the sample surface is uniform. In the present state, one portion in contact with the mask surface is provided, the output of the high voltage power supply is connected to increase the area in contact with the sample where a high voltage is applied to the surface of the sample. A portion to which a sample application electrode is attached is referred to as a frame, and is moved vertically to convey the sample to the inside. In the state where the frame is lowered, the sample application electrode is in contact with the sample surface, and a voltage can be uniformly supplied to the sample (see FIG. 33A).

Furthermore, use of another frame structure is effective for uniform and stable application. FIG. 33B shows the example. In consideration with the bottom view (FIG. 33B(b)) and the top view (FIG. 33B(c)) of the frame shown in FIG. 33B, the frame structure has a smooth finished top surface without projections. For instance, the frame is a plate material with 195×195 mm□ that is made of titanium or phosphor bronze, and a hole of 146×146 mm is formed at the inner part. As shown in the bottom view, three projections are provided. The projection has a height of about 10 to 200 μm. The tip of the projection may be sharp. Through use of the frame (cover), a prescribed value of voltage is applied to the surface layer of the mask. In the present invention, the mask is provided on the pallet. The pallet is provided with mask support pins. An exposure mask, such as an EUV mask, is provided on the pins. The mask support pins are made of material with a little amount of particle occurrence. The pins are metal members coated with resin, such as polyimide, Teflon (registered trademark) and fluororesin, or members made of resin. The mask arrangement position of the support pins are outside of the portion of 142×142 mm inside of the mask; contact is made at the positions. At the inside of the positions are subjected to adverse effect of inclination of the mask if foreign matters and particles adhere when the mask is arranged in the exposure apparatus. The pins prevent foreign matters and particles from adhering to the region. Instead, the mask can be fixed in contact with the support pins at the corners of the side and the bottom of the mask. In this case, the contact part has a surface structure inclined at a prescribed angle. In order to prevent the position of the mask from varying during movement of the stage, mask fixing guide pins for positional fixing may be provided to cause the mask to be in contact and fixed.

It is provided that the EUV mask is thus arranged. A typical EUV mask includes an insulation film on the uppermost surface, and a conductive film is arranged beneath the insulation film. Accordingly, in order to apply a stable and uniform voltage to the mask surface, the voltage is required to be applied to the conductive film breaking though the uppermost insulation film. At this time, the frame (cover) including the projections shown in FIG. 33B is effective. A prescribed voltage to be applied to the mask surface is applied to the frame. As shown in FIG. 33A, the frame is provided from above of the mask. At this time, the projections break through the insulation film and reach the lower conductive film, and a stable voltage can be applied. Since the projections serves as portions of application to the mask, the application positions can be identified, that is, the voltage can be applied while the positions are controlled. Furthermore, the contact is made at the three points. Accordingly, an advantageous effect of allowing the parallelity between the top surface of the mask and the frame can be achieved. According to arrangement at two points, the frame is inclined. According to arrangement at four points or more, it is difficult to identify which projection actually breaks the insulation film and applies the voltage to the conductive film. Likewise, according to the case with no projection, it is difficult to identify at which portion the mask is in contact. Another different contact state may be established every mask replacement. Here, the thickness of the insulation film in the EUV mask is typically 10 to 20 nm. Accordingly, the frame weight is selected to be suitable to the breaking.

The step between the mask surface and the frame in the case of being in contact with the frame is required to be small. This configuration is required because the step causes nonuniformity of the electric field distribution. In the case of inspection at an end of the mask, i.e., at a position near the frame, the nonuniformity of the electric field distribution may sometime cause the electronic trajectory to deviate, and the coordinates and the center position of the electronic image may deviate. Thus, the step between the frame and the mask surface is required to be minimum. In the present invention, the step is configured to have a dimension suppressed to 10 to 200 μm. It is preferred that the step has a dimension of 10 to 100 μm. A scheme may be adopted where a portion and therearound of the frame that is in contact with the mask has a thin plate thickness. This embodiment is also applicable to the aforementioned Embodiments 1 to 4.

Figure 35:
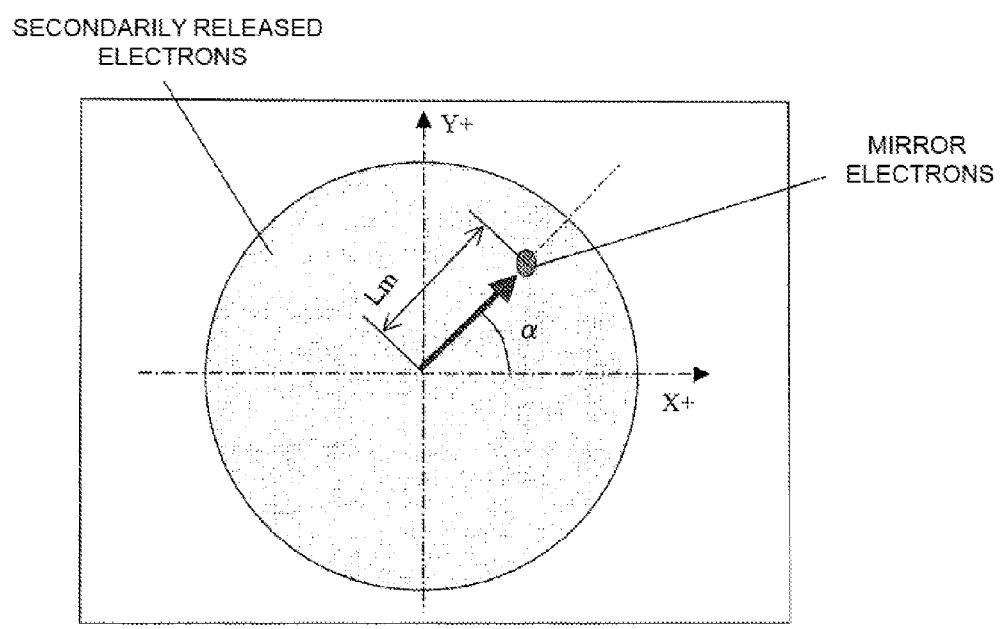
FIG. 35 is a diagram showing an example of beam observation at a CO position, according to an embodiment of the present invention.

FIGS. 34A and 34B show a diagram showing an incident angle of a primary beam for a sample in an inspection method according to one embodiment of the present invention. As shown in FIGS. 34A and 34B, it is defined that the irradiation angle $\theta$ of an incident electron beam and irradiation direction $\alpha$ to the sample (or column coordinates). That is, the angle from the direction perpendicular to the sample surface (Z direction; the same direction as the optical axis direction of the secondary optical system) is defined as $\theta$. For instance, when $\theta=0$, the incident direction is perpendicular to the sample surface. When $\theta=90$ degrees, the incident direction is parallel to the sample. When the inclined direction $\theta=45$ degrees, the incident direction is 45 degrees from the sample surface. $\theta$ may be represented in an absolute value from the Z axis. In both the cases on right and left sides from the Z axis, the same angle is regarded as the same value of $\theta$. Typically, $\theta$ ranges from 0 to 45 degrees. As to an example of $\alpha$, on the sample (or column coordinates), the X and Y directions are defined such that the E direction of the E×B is the Y direction and the B direction is the X direction. For instance, the E+ side of the E×B (the direction where the primary optical system is) is Y+, and the E− side is Y−. Here, in view of the sample from the detector side, 90 degrees in the clockwise direction from Y+ is X+, and X− is 90 degrees in the counterclockwise direction from Y+. For instance, in the case where the sample is laid in a pattern region represented by a longitudinal line/space (L/S) and a lateral line/space (L/S), arrangement of the longitudinal line in the Y direction and the lateral line in the X direction facilitates understanding. Here, as shown in FIG. 34A, the sample incident angle can be defined as a while the X+ direction is 0 degree. When $\alpha=0$, the incident direction of the primary electron beam is the X+ direction. An example of the inclined direction where $\alpha=45$ degrees is an angle of 45 degrees obliquely incident in the intermediate direction between the X+ and Y+ directions. That is, a similar irradiation direction of the primary electron beam can be formed with respect to each of the longitudinal L/S and the lateral L/S. An electronic signal can be formed on the basis of the similar line and space, and a similar contrast and S/N ratio can be acquired. After adjustment of the $\theta$ and $\alpha$ values, beam observation where the NA aperture of the secondary optical system is at a certain CO position results in what is shown in FIG. 35. FIG. 35 is a diagram showing an example of beam observation at the CO position. This example is an adjustment example in the transition region.

The beam of the secondarily released electrons has a circular shape at the CO position. This state shows electrons released from the surface due to collision of the electron beam with the sample. Accordingly, the release direction from the surface is isotropic. Thus, the circular shape is shown at the CO position. On the contrary, mirror electrons are reflected in proximity to the surface in a direction affected by the $\theta$ and $\alpha$. Accordingly, mirror electrons are formed on a position where $\theta$ and $\alpha$ are reflected, at the CO position.

For instance, in the case of the incident angle α with respect to the sample, the position is formed in the α angle direction at the CO position with respect to the circle of the secondarily released electrons. Provided that the vertical direction on the sample surface is Z and the detector direction is Z+, the incident angle from Z is θ. The magnitude of the θ affects the mirror electron position at the CO position. That is, if the θ (absolute value) is large as shown in FIG. 35, the distance Lm of the secondarily released electrons from the CO center is large. In other words, in the case of an oblique incident direction, a large incident angle θ causes the mirror electron position to be formed at a position apart from the CO center of the secondarily released electrons. If the primary electron beam is perpendicularly incident, the mirror electron position is formed at the CO center position of the secondarily released electrons.

Figure 36:
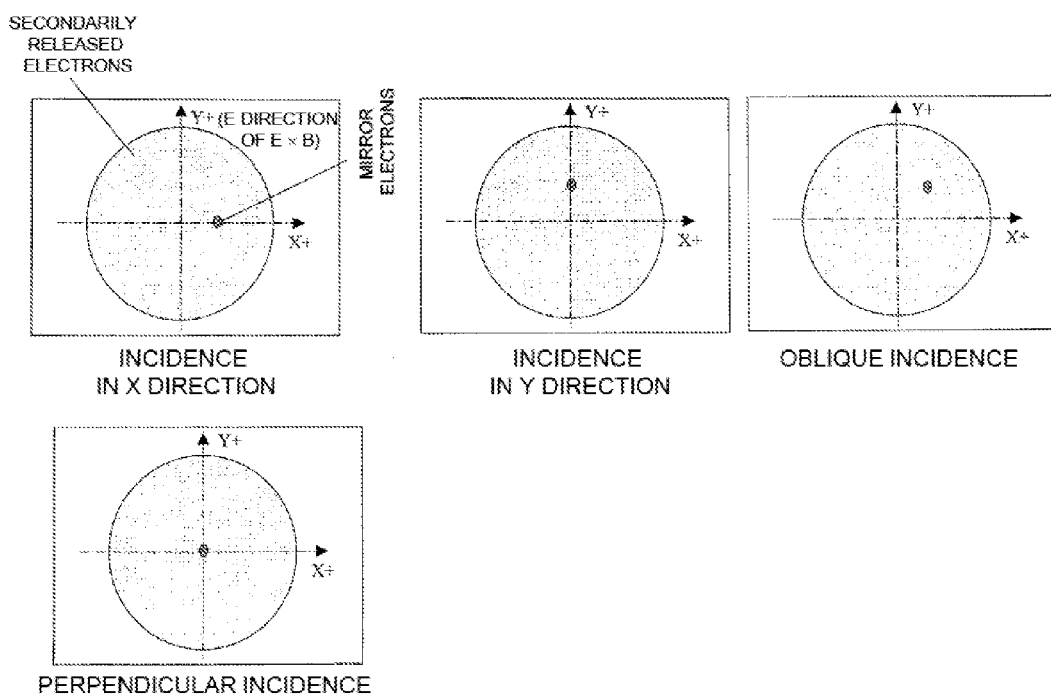
FIG. 36 is a diagram showing a mirror electron position at an incident angle of a primary electron beam, according to an embodiment of the present invention.

FIG. 36 shows the example. FIG. 36 is a diagram showing the mirror electron position at an incident angle of the primary electron beam. In the case of irradiation with the electron beam in the X direction, the mirror electron position is formed on the X axis with respect to the CO of the secondarily released electrons. In the case of the irradiation of the electron beam in the Y direction, the mirror electron position is formed on the Y axis with respect to the CO of the secondarily released electrons. In the case of irradiation in the inclined direction α, the mirror electron position is formed in the α direction with respect to the CO of the secondarily released electrons. Typically used values of α are 0, 30, 45, 60, 90, 120, 150, 180, 210, 240 and 270 degrees. The θ is often used in a range of 0 to 45 degrees. In the case of the surface with asperities capable of acquiring high contrast and a high S/N ratio, θ is often used in a range of 0 to 20 degrees on, for instance, an EUV mask, a nanoimprint mask and a semiconductor wafer.

The incident angle of the primary system can be controlled using the beam aligner of the primary system. The X direction can be adjusted by the beam aligner of the primary system, and the Y direction can be adjusted by the E×B. Instead, the Y direction may be aligned by the beam aligner instead of the E×B.

The present invention adjusts the NA position for forming the electronic image conditions with high contrast and a high S/N ratio. The adjustment is made because acquired image information is different and the image quality largely varies according to the relationship between the mirror electron position and the NA position. For instance, a. Image including many mirror electrons: NA is provided adjacent to the mirror electron position.

b. Image with white pits/black bumps where the asperity pattern includes many mirror electrons at the pits.

c. Image with black pits/white bumps where the asperity pattern includes a small number of mirror electrons at the pits.

d. Image with asymmetric contrast, longitudinal/lateral pattern, etc.

e. Image etc. where mirror electrons are formed at the edges of the asperities.

Accordingly, in order to acquire a required image, the relationship between the mirror electron position and the NA position is required to be acquired and set. Conventionally, because of insufficient understanding of an occurring phenomenon and of an adjustment method, the NA is randomly moved and images are acquired to determine conditions. The present invention improves operation efficiency, and can significantly reduce time and cost. Here, an NA movable mechanism is required in order to adjust and dispose the NA position. A two-dimensional movement mechanism is more preferable. In a one-dimensional movement, when the MC (mirror electron position) in the inclined direction or in an immovable axial direction with reference to the CO center of the secondarily released electrons (e.g., if only movable in the X direction, immovable in the Y direction), the NA cannot be arranged between the MC and the CO center position; thus, to prevent the drawback, two-dimensional movement is preferable.

Figure 37:
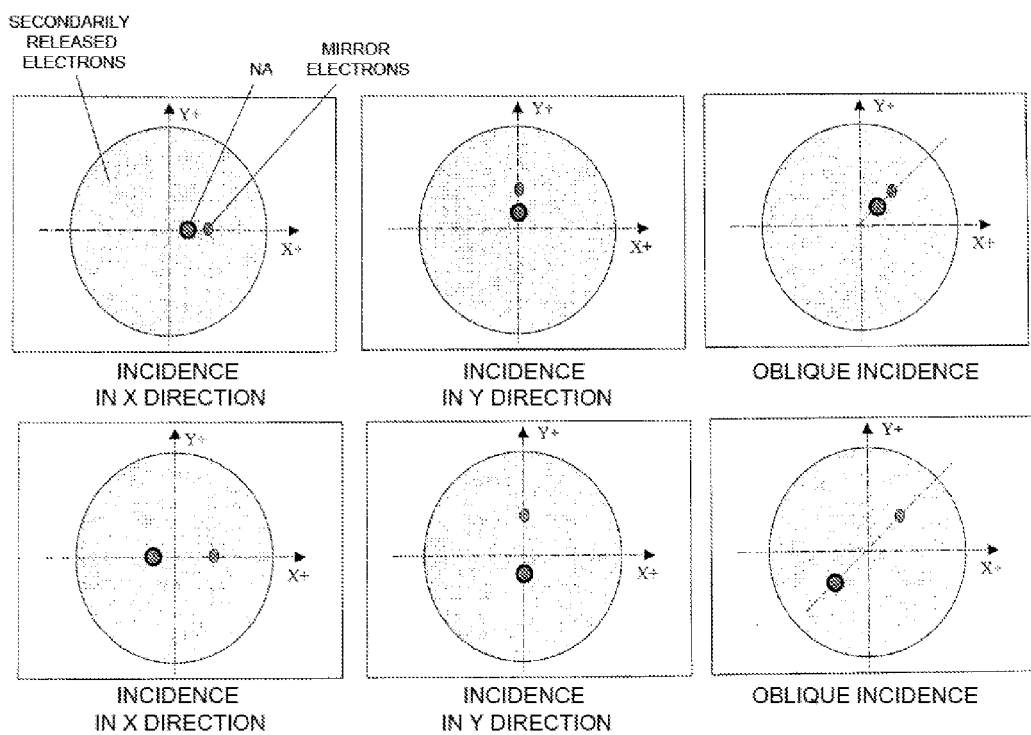
FIG. 37 is a diagram showing an example of a mirror electron position and an NA position, according to an embodiment of the present invention.
Figure 38:
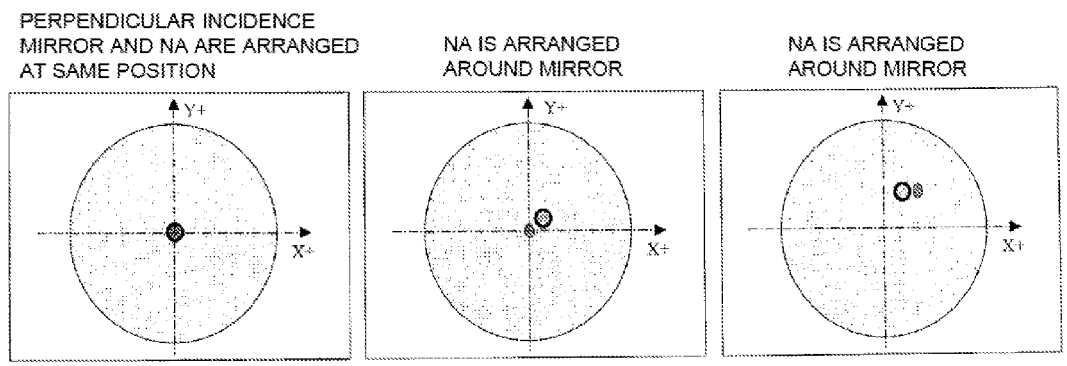
FIG. 38 is a diagram showing an example of a mirror electron position and an NA position, according to an embodiment of the present invention.

FIGS. 37 and 38 are diagrams showing examples of the mirror electron positions and the NA positions. An analogous adjustment method is applicable not only to a sample with an asperity pattern but also to a sample with a flat surface. Even in the case of the flat sample, if an image capturing variation in potential or material is required to be formed on the sample, conditions suitable to capturing variation can be acquired by the present invention and created. For instance, the present invention is applicable to detection of fine foreign matters, cleaning residues, contamination, etc. on the flat sample surface, and detection of a pattern where the conductive material and insulation material are mixed. Also in the case, as with the above description, the aforementioned condition creation method is applicable in order to acquire conditions with high contrast and a high S/N ratio of the defects and pattern. The highly sensitive detection, having not been conventionally achieved, can be achieved. Since such adjustment can be made, the case where contrast×1.2 to ×2, and S/N ratio×1.5 to ×5 can be acquired is verified in comparison with the conventional method performed while viewing an image. This case is significantly effective to adjustment time Tc and reproducibility. For instance, Tc=½ to ⅟10 can be acquired in comparison with the conventional case.

The NA setting positions are roughly classified into the case of arrangement around the mirror electron position, and the case of arrangement being apart from the position. The more apart the mirror electrons are disposed, the smaller the effects of the mirror electrons become.

Inspection of Sample with Mesa Structure

Method 1

Figure 39:
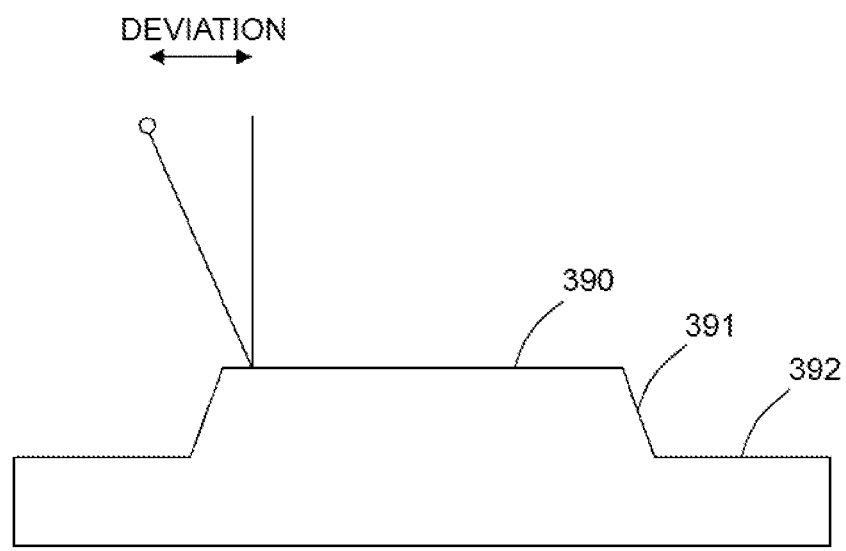
FIG. 39 is a diagram showing situations where an end of a mesa structure (portion in proximity to a step) is inspected.

In the inspection apparatus of the present invention, for inspection on a sample (inspection object) with a mesa structure, the relationships between the mirror electron positions and the NA positions on multiple positions on the edges of the mesa structure (adjacent to the step) are preliminarily acquired, mapped, and stored as mapping data in a storage (memory etc.). As shown in FIG. 39, in the case of inspecting the edges of the mesa structure (adjacent to the step 391), the incident angle of the beam in the primary system is controlled such that the mapping data is read, and the deviation of the mirror electron position is corrected (the secondary beam is always on the same position). The incident angle of the beam in the primary system is controlled, for instance, by two-dimensionally moving the NA using the two-dimensional (or one-dimensional) movement mechanism (or one-dimensional movement mechanism). Thus, even at the ends of the mesa structure (adjacent to the step 391), an image having high contrast and a high S/N ratio can be acquired. The "mesa structure" is a structure where the central flat portion (central planar portion) 390 is provided at the central portion, and a peripheral flat portion (peripheral planar portion) 392 is provided via the step 391 at the periphery of the central portion (see FIG. 39). The inspection apparatus of the present invention is also effective to inspection not only on the sample (inspection object) having the mesa structure but also on the sample (inspection object) with a pattern with asperities.

Method 2

Figure 40:
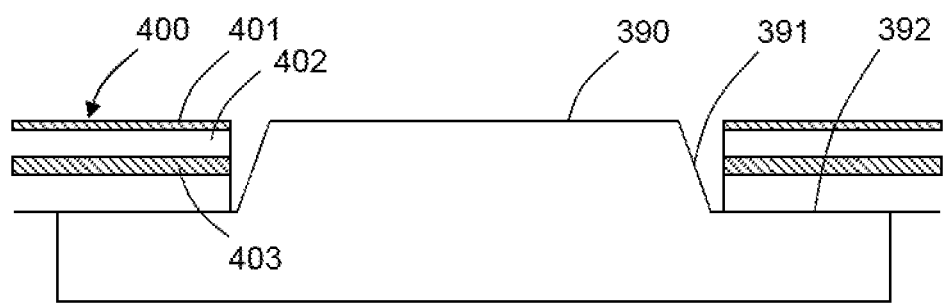
FIG. 40 is a diagram showing a configuration of an electric field correction plate, according to an embodiment of the present invention.

In the inspection apparatus of the present invention, for inspection on the sample (inspection object) having a mesa structure, as shown in FIG. 40, an electric field correction plate 400 may be provided at the outer periphery (around the step 391) of a central flat portion 390 of the mesa structure. For instance, the electric field correction plate includes: an electrode 401 on the surface; an insulating layer 402 provided below the electrode; and an electrode 403 that is for an electrostatic chuck and is provided below the insulating layer. The material of the electrode 401 is, for instance, Cr, CrN, Ru, Au, Ti, etc. The material of the insulating layer 402 is, for instance, insulation material, such as polyimide, Teflon, and ceramics. Thus, the nonmagnetic conductive material is preferable. The material of the electrode 403 for the electrostatic chuck is, for instance, Cu, Al and the like.

A surface voltage (e.g., −5 kV) equivalent to the surface voltage applied to the conductive film (not shown) on the sample surface is applied to the electrode 401. Application of the voltage to the electrode 403 for the electrostatic chuck exerts electrostatic chuck effects to allow the electric field correction plate (electrode 401) to be in close contact with the inspection object. Thus, the flatness (uniformity of the electric field) on the electrode surface can be secured, and distortion of the electric field adjacent to the step 391 of the mesa structure can be suppressed. Also through use of such an electric field correction plate 400, an image having high contrast and a high S/N ratio can be acquired at the edges (adjacent to the step 391) of the mesa structure.

Furthermore, the "Method 1" and the "Method 2" can be combined, thereby exerting advantageous effects of correcting a highly accurate electronic image. The trajectory of the electron beam is appropriately corrected by the electric field corrected by the electric field correction plate. Thus, the distortion of the electronic image is corrected. However, there is a case where correction is not completely made. In this case, combination of the systems according to the "Method 1" is significantly effective. The distortion of the image, particularly the distortion at the ends of the image, causes adverse effects in the case of a TDI image. Framing out of elements arranged in a column for accumulation in the TDI sensor causes blurring and the like. Use of the combination can suppress a distortion of about $\frac{1}{3}$-$\frac{1}{10}$ with respect to a pixel. A TDI image where image blurring at the ends are reduced can be acquired. Such highly accurate correction is effective particularly in the case of pattern inspection.

The embodiments of the present invention have been described using the examples. However, the scope of the present invention is not limited thereto, and can be changed or deformed according to objects within a scope described in claims.

As described above, the inspection apparatus according to the present invention is effective as the semiconductor inspection apparatus that inspects defects of the pattern formed on the surface of the inspection object.

As described above, the inspection apparatus according to the present invention is effective as a semiconductor inspection apparatus that can acquire an image having high contrast and a high S/N ratio at the ends of the mesa structure.

TABLE 1

|  | RTD | V0 | DV |
|---|---|---|---|
| EXAMPLE 1 | −30 kV | 0 V | −25 kV |
| EXAMPLE 2 | −5 kV | −25 kV | 0 V |
| EXAMPLE 3 | 0 V | −30 kV | +5 kV |

What is claimed is:

1. An inspection apparatus, comprising:
    beam generation means for generating any of charged particles and electromagnetic waves as a beam;
    a primary optical system that guides the beam into an inspection object held in a working chamber and irradiates the inspection object with the beam;
    a secondary optical system that detects secondary charged particles occurring from the inspection object; and
    an image processing system that forms an image on the basis of the detected secondary charged particles,
    wherein the primary optical system comprises a photoelectron generator having a photoelectronic surface, and a base material of the photoelectronic surface is made of material with a higher thermal conductivity than a thermal conductivity of quartz.

2. The inspection apparatus according to claim 1, wherein the base material of the photoelectronic surface is made of sapphire or diamond.

3. The inspection apparatus according to claim 1, wherein the photoelectronic surface has a circular shape having a diameter of 10 to 200 μm or a rectangular shape having a side of 10 to 200 μm.

4. The inspection apparatus according to claim 1, wherein photoelectronic material is coated on the photoelectronic surface, and the photoelectronic material is ruthenium or gold.

5. The inspection apparatus according to claim 4, wherein the photoelectronic material has a thickness of 5 to 100 nm.

6. An inspection apparatus, comprising:
    beam generation means for generating any of charged particles and electromagnetic waves as a beam;
    a primary optical system that guides the beam into an inspection object held in a working chamber and irradiates the inspection object with the beam;
    a secondary optical system that detects secondary charged particles occurring from the inspection object; and
    an image processing system that forms an image on the basis of the detected secondary charged particles,
    wherein a central portion of the inspection object is provided with a central flat portion, a periphery of the central flat portion is provided with a peripheral flat portion via a step, and an electric field correction plate is arranged around the step, and
    a surface voltage equivalent to a surface voltage applied to the inspection object is applied to an electrode on a surface of the electric field correction plate.

7. The inspection apparatus according to claim 6,
    wherein the electric field correction plate comprises an insulation layer provided below the electrode, and an electrode that is for an electrostatic chuck and is provided below the insulating layer, and
    the electric field correction plate is in close contact with the inspection object by applying a voltage to the electrode for the electrostatic chuck.

8. An inspection apparatus, comprising:
    beam generation means for generating any of charged particles and electromagnetic waves as a beam;
    a primary optical system that guides the beam into an inspection object held in a working chamber and irradiates the inspection object with the beam;
    control means for controlling an incident angle of the beam with which the inspection object is irradiated;
    a secondary optical system that detects secondary charged particles occurring from the inspection object; and
    an image processing system that forms an image on the basis of the detected secondary charged particles, wherein a central portion of the inspection object is provided with a central flat portion, a periphery of the central flat portion is provided with a peripheral flat portion via a step, relationship between a detection position of the secondary charged particles in proximity to the step and the incident angle of the beam is stored as mapping data in a storage, and when proximity to the step is inspected, the control means controls the incident angle of the beam so as to correct deviation of the detection position of the secondary charged particles on the basis of the mapping data.

9. The inspection apparatus according to claim 8, wherein the control means is a movable numerical aperture, and a movement mechanism for the numerical aperture, the mapping data is data that maps a relationship between a plurality of mirror electron positions in proximity to the step and a position of the numerical aperture, and when proximity to the step is inspected, the numerical aperture is moved by the movement mechanism on the basis of the mapping data, and the incident angle of the beam is controlled to correct a deviation of the mirror electron position.

\* \* \* \* \*

UNITED STATES PATENT AND TRADEMARK OFFICE
CERTIFICATE OF CORRECTION

PATENT NO.        : 8,742,344 B2
APPLICATION NO.   : 14/026385
DATED             : June 3, 2014
INVENTOR(S)       : Hatakeyama et al.

It is certified that error appears in the above-identified patent and that said Letters Patent is hereby corrected as shown below:

In the Specification
- Column 20, line 25, delete "KOhler" and insert --Köhler--
- Column 22, line 8, delete "KOhler" and insert --Köhler--
- Column 22, line 61, delete "#30" and insert --ϕ30--
- Column 22, line 62, delete "#300" and insert --ϕ300--
- Column 32, line 13, delete "#100" and insert --ϕ100--
- Column 32, line 14, delete "450" and insert --ϕ50--
- Column 39, line 56, delete "(LEA LE 5 LEB)" and insert --(LEA≤ LE ≤LEB)--
- Column 48, line 19, delete "8" and insert --θ--

Signed and Sealed this
Third Day of February, 2015

Michelle K. Lee
*Deputy Director of the United States Patent and Trademark Office*